(12) United States Patent
Fung

(10) Patent No.: US 11,951,355 B2
(45) Date of Patent: *Apr. 9, 2024

(54) HEALTH-RELATED DATA COLLECTION SYSTEM FOR HEALTHCARE DIAGNOSTICS AND TREATMENT PLATFORMS

(71) Applicant: Blue Goji LLC, Austin, TX (US)

(72) Inventor: Coleman Fung, Austin, TX (US)

(73) Assignee: BLUE GOJI LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/189,698

(22) Filed: Mar. 24, 2023

(65) Prior Publication Data

US 2023/0211205 A1 Jul. 6, 2023

Related U.S. Application Data

(63) Continuation-in-part of application No. 18/080,343, filed on Dec. 13, 2022, now Pat. No. 11,823,781, and
(Continued)

(51) Int. Cl.
*G16H 10/60* (2018.01)
*A61B 5/02* (2006.01)
(Continued)

(52) U.S. Cl.
CPC ...... *A63B 24/0003* (2013.01); *A63B 22/0046* (2013.01); *A63B 22/0285* (2013.01);
(Continued)

(58) Field of Classification Search
CPC ............ A63B 24/0003; A63B 22/0046; A63B 22/0285; A63B 22/0292; A63B 22/06;
(Continued)

(56) References Cited

U.S. PATENT DOCUMENTS 10,758,732 B1 9/2020 Heldman
10,799,667 B2 10/2020 Hanbury
(Continued)

OTHER PUBLICATIONS

Rodriquez Kari, International Search Report, dated Jun. 8, 2023, p. 2.
(Continued)

*Primary Examiner* — Maroun P Kanaan
(74) *Attorney, Agent, or Firm* — Galvin Patent Law LLC; Brian R. Galvin

(57) ABSTRACT

A method and method for a cloud-based gaming platform with integrated healthcare diagnostic and treatment capabilities. In an embodiment, the system and method comprise a cloud-based gaming platform comprising a frontend accessible from various game clients which operates a gaming environment on one or more game servers, a backend that provides the game database and analytics used by the game servers to operate the gaming environment, and a healthcare diagnostics and treatment module integrated into the platform comprising a HIPPA-compliant security gateway, an AI-assisted healthcare diagnostics module, and an alert and treatments module. Exercising on an exercise machine compatible with the cloud-based gaming platform entertains the user while simultaneously capturing data about the user's physical and mental performance which can be used to diagnose medical conditions and, depending on configuration, implement treatment regimens comprising exercise routines and mental simulation via tasks in the gaming environment.

16 Claims, 35 Drawing Sheets

Related U.S. Application Data a continuation-in-part of application No. 17/888,450, filed on Aug. 15, 2022, which is a continuation of application No. 17/592,802, filed on Feb. 4, 2022, now Pat. No. 11,465,014, said application No. 18/080,343 is a continuation-in-part of application No. 17/574,540, filed on Jan. 12, 2022, now Pat. No. 11,524,209, said application No. 17/592,802 is a continuation-in-part of application No. 17/574,540, filed on Jan. 12, 2022, now Pat. No. 11,524,209, and a continuation-in-part of application No. 16/781,663, filed on Feb. 4, 2020, now Pat. No. 11,191,996, which is a continuation-in-part of application No. 16/354,374, filed on Mar. 15, 2019, now Pat. No. 10,549,153, which is a continuation-in-part of application No. 16/176,511, filed on Oct. 31, 2018, now Pat. No. 10,960,264, which is a continuation-in-part of application No. 16/011,394, filed on Jun. 18, 2018, now Pat. No. 10,155,133, which is a continuation-in-part of application No. 15/853,746, filed on Dec. 23, 2017, now Pat. No. 10,265,578, which is a continuation of application No. 15/219,115, filed on Jul. 25, 2016, now Pat. No. 9,849,333, which is a continuation-in-part of application No. 15/193,112, filed on Jun. 27, 2016, now abandoned, which is a continuation-in-part of application No. 15/187,787, filed on Jun. 21, 2016, now Pat. No. 10,124,255, which is a continuation-in-part of application No. 15/175,043, filed on Jun. 7, 2016, now Pat. No. 9,766,696, and a continuation-in-part of application No. 14/846,966, filed on Sep. 7, 2015, now Pat. No. 10,080,958, and a continuation-in-part of application No. 14/012,879, filed on Aug. 28, 2013, now Pat. No. 10,737,175.

(60) Provisional application No. 62/330,602, filed on May 2, 2016, provisional application No. 62/330,642, filed on May 2, 2016, provisional application No. 62/310,568, filed on Mar. 18, 2016, provisional application No. 61/696,068, filed on Aug. 31, 2012.

(51) Int. Cl.

| | | |
|---|---|---|
| *A63B 21/00* | (2006.01) | |
| *A63B 22/00* | (2006.01) | |
| *A63B 22/02* | (2006.01) | |
| *A63B 22/06* | (2006.01) | |
| *A63B 23/04* | (2006.01) | |
| *A63B 24/00* | (2006.01) | |
| *A63F 13/212* | (2014.01) | |
| *A63F 13/214* | (2014.01) | |
| *A63F 13/40* | (2014.01) | |
| *A63F 13/65* | (2014.01) | |
| *G06F 1/16* | (2006.01) | |
| *G06F 3/01* | (2006.01) | |
| *G06T 19/00* | (2011.01) | |
| *H04W 84/18* | (2009.01) | |

(52) U.S. Cl.
CPC .......... *A63B 22/0292* (2015.10); *A63B 22/06* (2013.01); *A63B 23/04* (2013.01); *A63F 13/212* (2014.09); *A63F 13/214* (2014.09); *A63F 13/40* (2014.09); *A63F 13/65* (2014.09); *G06F 1/163* (2013.01); *G06F 3/011* (2013.01); *G06F 3/016* (2013.01); *G06T 19/006* (2013.01); *H04W 84/18* (2013.01)

(58) Field of Classification Search
CPC ...... A63B 23/04; A63F 13/212; A63F 13/214; A63F 13/40; A63F 13/65; A63F 13/213; A63F 13/245; A63F 13/816; G06F 1/163; G06F 3/011; G06F 3/016; G06F 1/1605; G06F 1/1626; G06F 1/1686; G06F 1/1688; G06F 3/013; G06T 19/006; H04W 84/18; G16H 10/20; G16H 15/00; G16H 20/30; G16H 20/70; G16H 40/63; G16H 40/67; G16H 50/20; A61B 5/7405; A61B 5/7455; A61B 5/4836; A61B 5/6803; A61B 5/745; A61B 5/375; A61B 5/0205; A61B 5/02438; A61B 5/11; A61M 2021/0022; A61M 2021/0027; A61M 2021/0044; A61M 2021/005; A61M 2021/0072; A61M 2205/3306; A61M 2205/332; A61M 2205/3553; A61M 2205/3561; A61M 2205/3584; A61M 2205/3592; A61M 2205/507; A61M 2210/0612; A61M 2230/06; A61M 2230/10; A61M 2230/50; A61M 2230/62; A61M 2230/63; A61M 21/02

See application file for complete search history.

(56) References Cited

U.S. PATENT DOCUMENTS

| | | |
|---|---|---|
| 11,051,730 B2 | 7/2021 | Tien et al. |
| 2009/0023554 A1* | 1/2009 | Shim ..................... A63B 22/02 482/4 |
| 2011/0143839 A1 | 6/2011 | McLaughlin |
| 2011/0269601 A1 | 11/2011 | Nelson et al. |
| 2014/0274567 A1 | 9/2014 | McCready et al. |
| 2016/0139666 A1 | 5/2016 | Rubin et al. |
| 2016/0187974 A1 | 6/2016 | Mallinson |
| 2017/0344716 A1* | 11/2017 | Abou-Sayed .......... G06Q 40/08 |
| 2019/0105509 A1* | 4/2019 | Tsai ..................... A61M 21/00 |
| 2021/0339043 A1 | 11/2021 | Malchano et al. |

OTHER PUBLICATIONS

Harry C. Kim, International Search Report, dated May 5, 2023, p. 3.

* cited by examiner

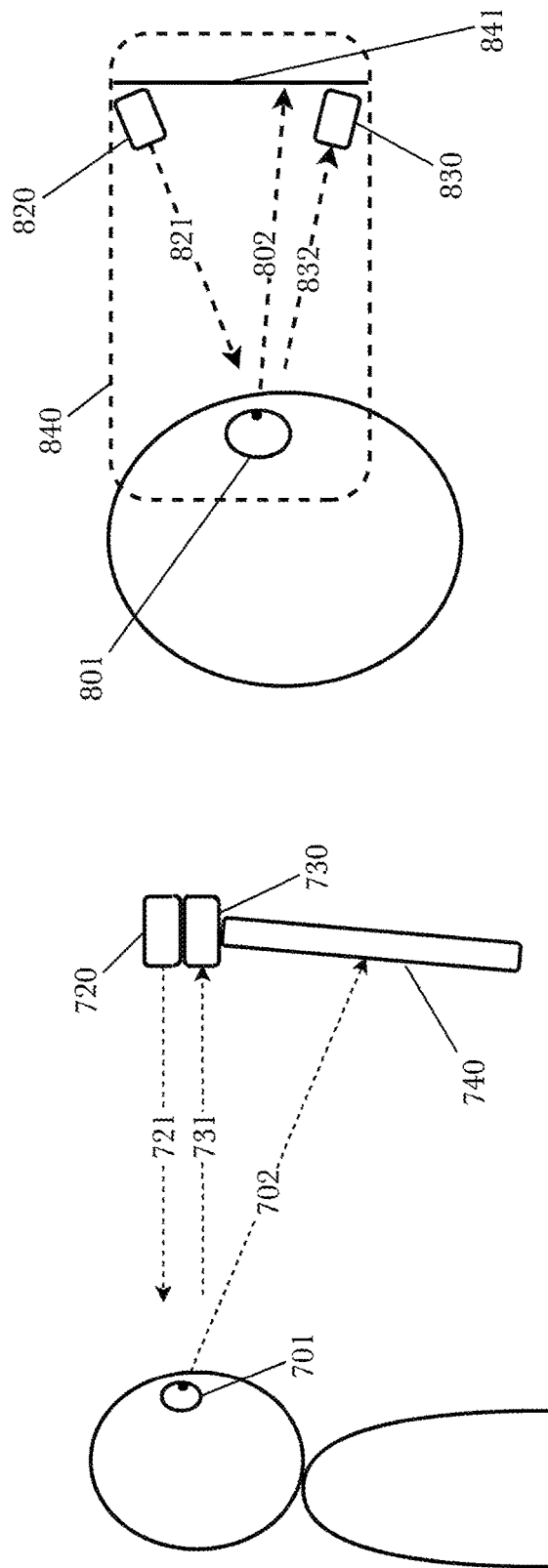
Fig. 8 (PRIOR ART)
Fig. 7 (PRIOR ART)
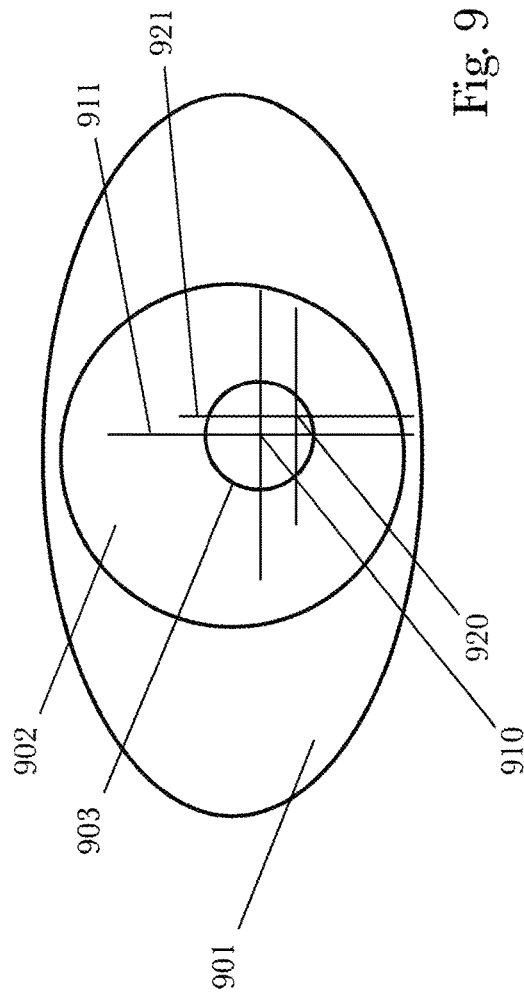
Fig. 9 (PRIOR ART)

HEALTH-RELATED DATA COLLECTION SYSTEM FOR HEALTHCARE DIAGNOSTICS AND TREATMENT PLATFORMS

CROSS-REFERENCE TO RELATED APPLICATIONS

Priority is claimed in the application data sheet to the following patents or patent applications, each of which is expressly incorporated herein by reference in its entirety:
Ser. No. 18/080,343
Ser. No. 17/888,450
Ser. No. 17/592,802
Ser. No. 17/574,540
Ser. No. 16/781,663
Ser. No. 16/354,374
Ser. No. 16/176,511
Ser. No. 16/011,394
Ser. No. 15/853,746
Ser. No. 15/193,112
Ser. No. 15/175,043
62/330,642
62/330,602
62/310,568
Ser. No. 14/846,966
Ser. No. 14/012,879
61/696,068

BACKGROUND OF THE INVENTION

Field of the Art

This disclosure relates to the field of healthcare diagnostics and treatment, and more particularly to systems and methods for data collection for rehabilitative and therapeutic neurological diagnostics and treatment platforms.

Discussion of the State of the Art

Research in medicine and psychology has improved our understanding of neurological function, but has failed to make significant progress in identifying and treating neurological conditions, especially in terms of preventing early cognitive decline and the onset of neurological disorders such as dementia. This lack of significant means to detect and improve neurological conditions has become increasingly important as lifespans in many parts of the world have increased. As the average age of populations has risen, cognitive issues such as dementia have become more common, and advances in identification and treatment have not kept pace. The lack of significant ability to identify and treat neurological conditions affects younger populations, as well, where mental issues such as depression can take a significant toll.

Research highlights the importance of continued neurological stimulation throughout all stages of life including stimulation through physical activity, social connection, and frequent cognitive challenge, but we still lack means for identifying and treating neurological disorders, especially in their early stages. Advancements in and virtual reality systems and environments have created new opportunities for immersive virtual experiences. However, this potential for immersive virtual experiences has not been used for much beyond computer gaming. Further, while virtual reality gaming platforms exist, including multi-person gaming platforms, none are capable of gathering health-related data about players during operation.

Further, medical diagnostics currently tend to involve unpleasant activities such physical exams, blood analysis, x-rays, MRIs, in the case of physical ailments, and verbal interviews and repetitive and boring on-paper or computer-based repetitive testing for neurological issues. All such current medical diagnostics are performed on a periodic basis, requiring doctors, nurses, and other medical professionals, so either cannot be performed regularly or are expensive to perform regularly. Medical treatment for physical issues tends to be prescription of diet, exercise, and medication, but implementation of these treatments is left to the patient, leading to lack of adherence with the recommendation. Medical treatment for neurological issues tends to be prescription of medication and is disconnected from treatment for physical issues. All of these diagnostic and treatment methodologies are tedious for the patient and adherence to recommendations and prescriptions can be low.

What is needed is a system and method for health-related data collection for cloud-based healthcare diagnostics and treatment platforms.

SUMMARY OF THE INVENTION

Accordingly, the inventor has conceived and reduced to practice, a system and method for health-related data collection for cloud-based healthcare diagnostic and treatment capabilities. In an embodiment, the system and method comprise a cloud-based gaming platform comprising a frontend accessible from various game clients which operates a gaming environment on one or more game servers, a backend that provides the game database and analytics used by the game servers to operate the gaming environment, and a healthcare diagnostics and treatment module integrated into the platform comprising a HIPPA-compliant security gateway, an AI-assisted healthcare diagnostics module, and an alert and treatments module. Exercising on an exercise machine compatible with the cloud-based gaming platform entertains the user while simultaneously capturing data about the user's physical and mental performance which can be used to diagnose medical conditions and, depending on configuration, implement treatment regimens comprising exercise routines and mental simulation via tasks in the gaming environment.

According to a preferred embodiment, a health-related data collection system for healthcare diagnostics and treatment platforms is disclosed, comprising: a piece of exercise equipment comprising a sensor configured to provide a first set of health-related data about a physiological aspect of a person using the exercise equipment while engaged in a virtual reality environment; a network-connected computing device comprising a memory and a processor; a frontend service comprising a first plurality of programming instructions stored in the memory which, when operating on the processor, causes the network-connected computing device to: receive a network connection from a game client, the game client operating on a remote computing device associated with the person and configured to transmit health-related information about the person to the frontend service; operate the virtual reality environment for engagement by the person while exercising on the exercise equipment, wherein the virtual reality environment is configured to capture a second set of health-related data about the person via in-game activities performed by the person while engaged in the virtual reality environment; transmit virtual reality environment data to the game client, the virtual reality environment data comprising data for rendering of the virtual reality environment on the remote computing device on which the game client is operating; and a HIPPA-compliant security gateway comprising a second plurality of programming instructions stored in the memory which, when operating on the processor, causes the network-connected computing device to: establish a HIPPA-compliant health data tunnel with the game client; direct the game client to send the first and second sets of health-related data to the HIPPA-compliant security gateway via that HIPPA-compliant health data tunnel; and store the health-related data in a patient database.

According to another preferred embodiment, a method for operating a health-related data collection system for healthcare diagnostics and treatment platforms is disclosed, comprising: collecting a first set of health-related data using a piece of exercise equipment comprising a sensor configured to provide the first set of health-related data about a physiological aspect of a person using the exercise equipment while engaged in a virtual reality environment; using a frontend service operating on a network-connected computing device comprising a memory and a processor to: receive a network connection from a game client, the game client operating on a remote computing device associated with the person and configured to transmit health-related information about the person to the frontend service; operate the virtual reality environment for engagement by the person while exercising on the exercise equipment, wherein the virtual reality environment is configured to capture a second set of health-related data about the person via in-game activities performed by the person while engaged in the virtual reality environment; transmit virtual reality environment data to the game client, the virtual reality environment data comprising data for rendering of the virtual reality environment on the remote computing device on which the game client is operating; and using a HIPPA-compliant security gateway operating on the network-connected computing device to: establish a HIPPA-compliant health data tunnel with the game client; direct the game client to send the first and second sets of health-related data to the HIPPA-compliant security gateway via that HIPPA-compliant health data tunnel; and store the health-related data in a patient database.

According to an aspect of an embodiment, the physiological aspect is selected from the list of step location, step pressure, and step timing, heart rate, blood pressure, blood-oxygen saturation, volume of oxygen maximum (VO2 Max), body temperature, and electrical activity in muscles and nerve cells that control the muscles.

According to an aspect of an embodiment, a physical function evaluator is used to calculate a physical function from the physiological aspect, wherein the physical function is selected from the list of gait symmetry, gait rhythm, balance, coordination, range of motion, fitness, reaction times, gross motor function, and fine motor function.

According to an aspect of an embodiment, in-game activities are configured to measure an aspect of mental function of the person, and the second set of health-related data about the person comprises data about the measurement of the mental function.

According to an aspect of an embodiment, the aspect of mental function is selected from the list of language, memory, cognition, attention, abstraction, and perception.

According to an aspect of an embodiment, the frontend service further receives a third set of health-related data comprising social data, the social data comprising the person's interactions with other persons relevant to the person's physical function or mental function.

According to an aspect of an embodiment, the social data is derived from in-game interactions with other players of the game.

According to an aspect of an embodiment, the social data is derived from extra-game interactions with persons not associated with the game.

According to an aspect of an embodiment, the physiological aspect is selected from the list of step location, step pressure, and step timing, heart rate, blood pressure, blood-oxygen saturation, volume of oxygen maximum (VO2 Max), body temperature, and electrical activity in muscles and nerve cells that control the muscles.

BRIEF DESCRIPTION OF THE DRAWING FIGURES

The accompanying drawings illustrate several embodiments of the invention and, together with the description, serve to explain the principles of the invention according to the embodiments. It will be appreciated by one skilled in the art that the particular embodiments illustrated in the drawings are merely exemplary, and are not to be considered as limiting of the scope of the invention or the claims herein in any way.

FIGS. 7-9 (PRIOR ART) explain the application of eye tracking technology as a means of determining where a user is looking.

Figure 10:
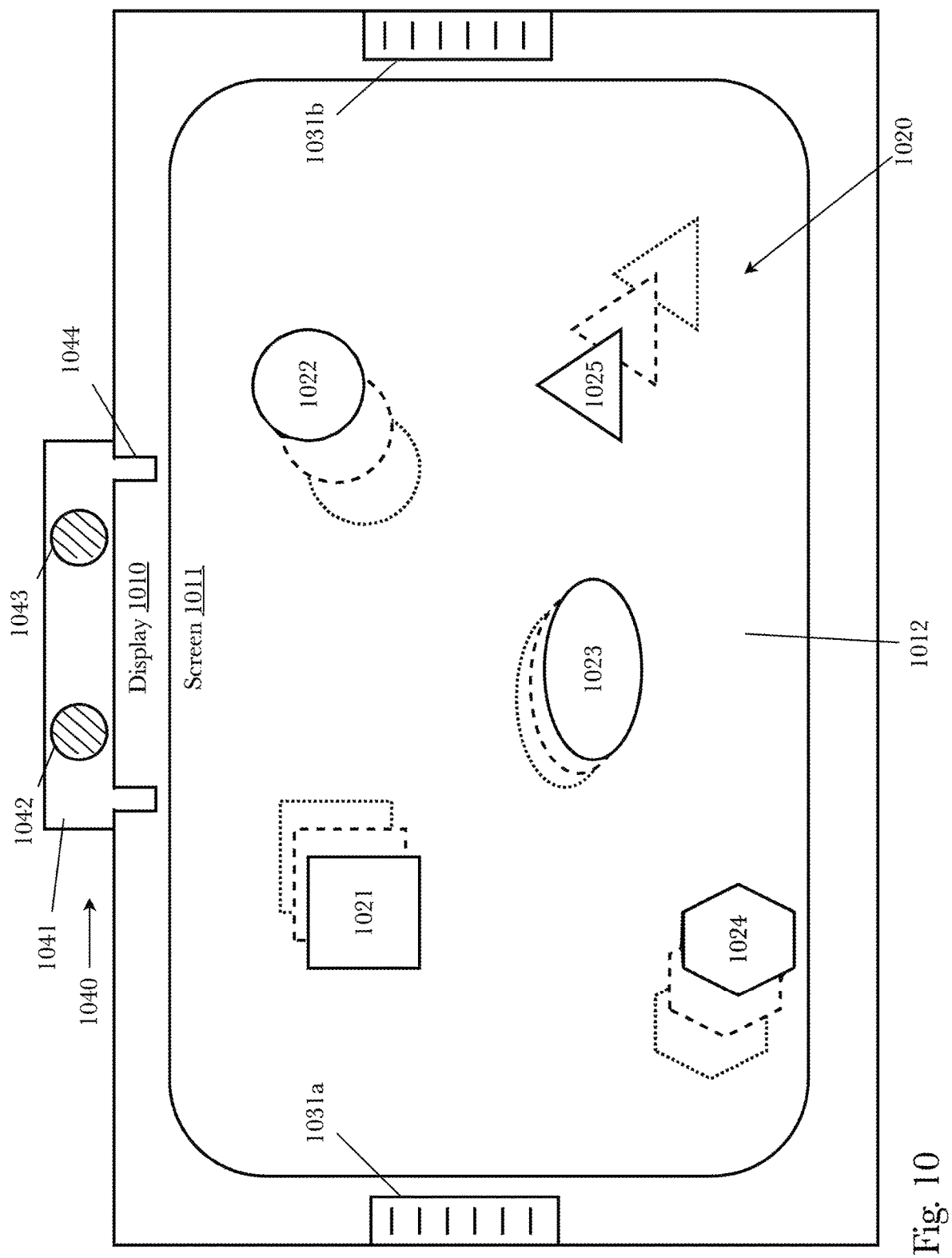

FIG. 10 is a diagram showing an embodiment in which on-screen elements of a display are used to apply brainwave entrainment in conjunction with eye tracking.

Figure 11:
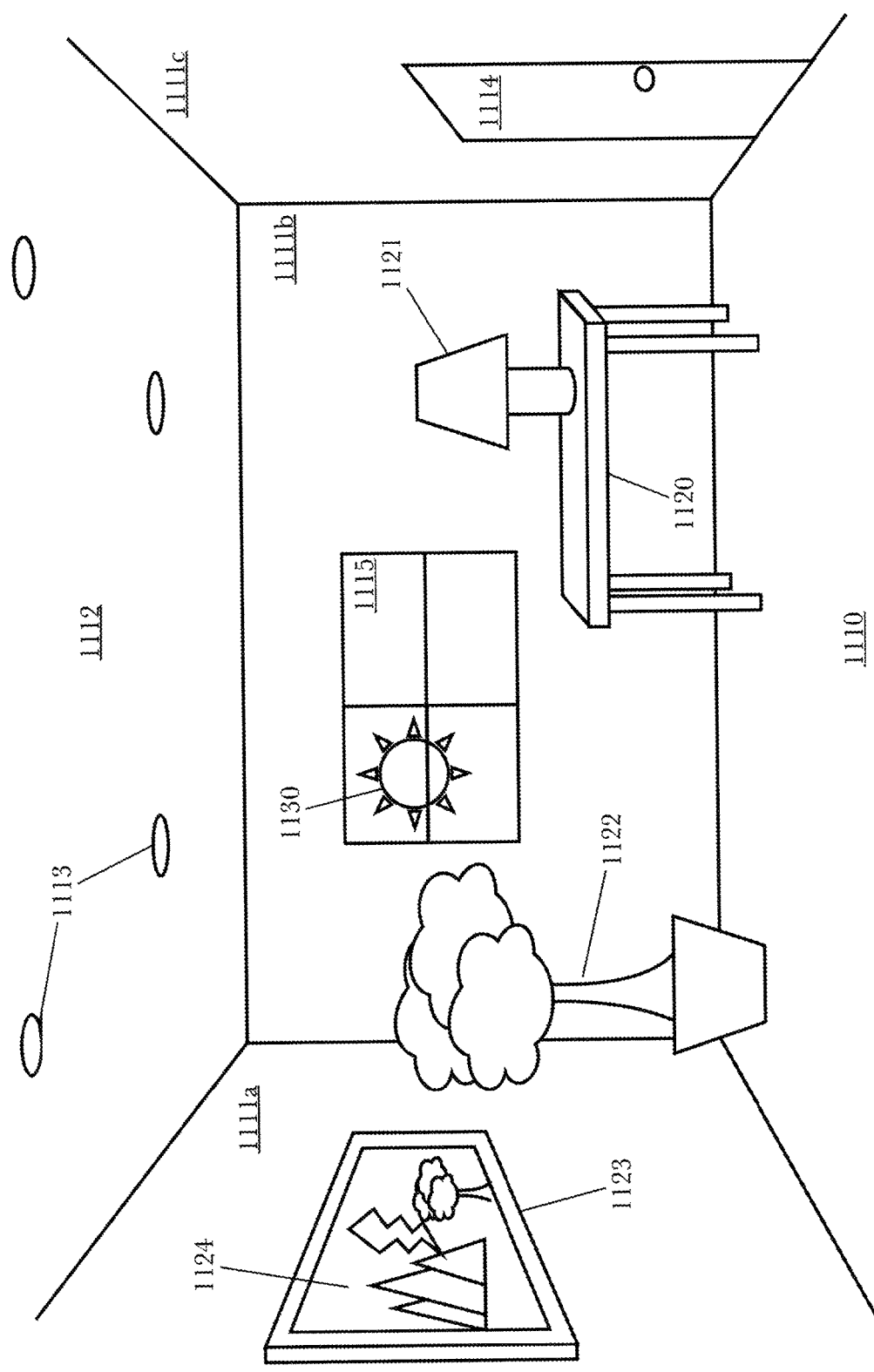

FIG. 11 is a diagram showing an exemplary virtual reality environment in which virtual objects may be used as visual stimulation transducers.

Figure 12:
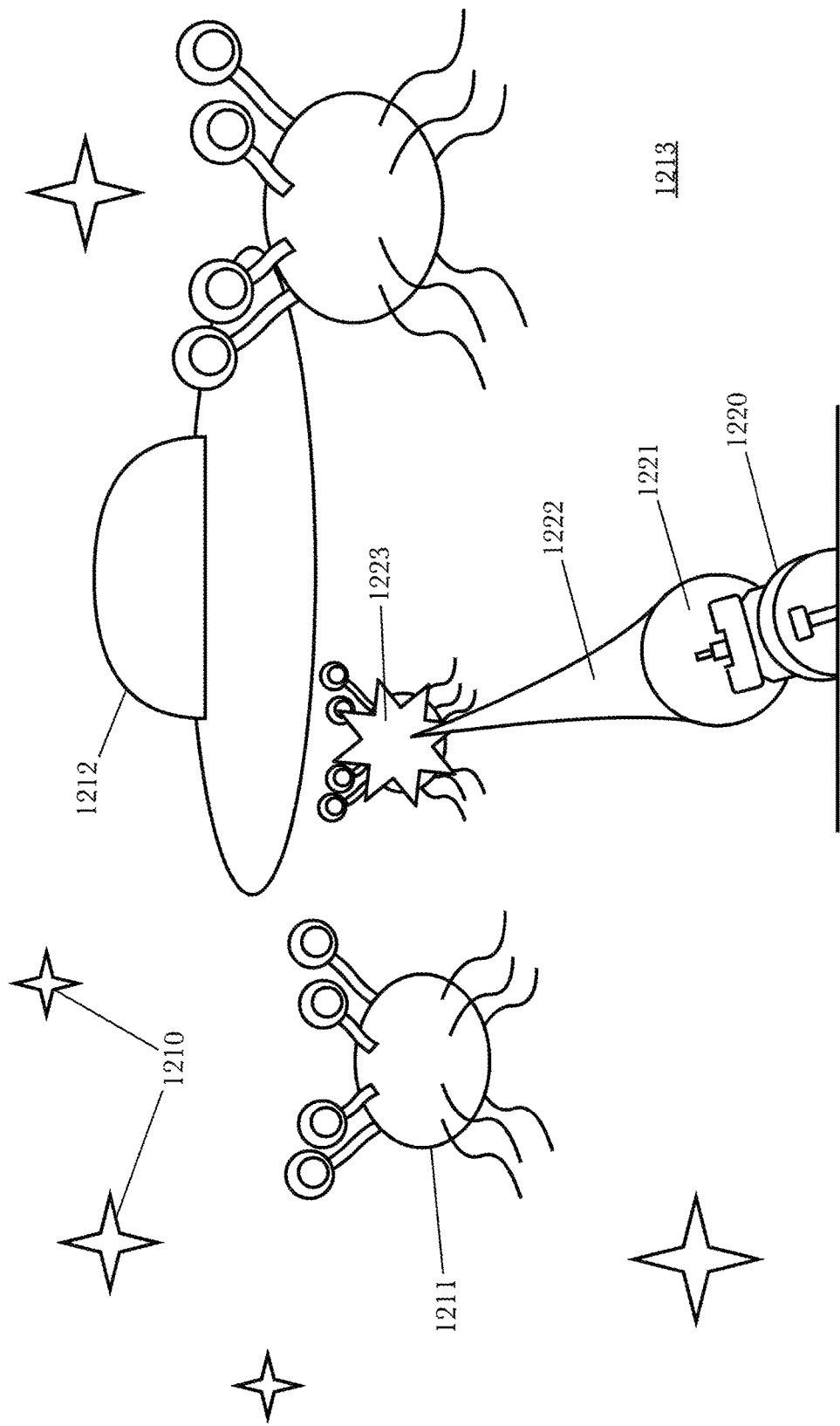

FIG. 12 is a diagram showing exemplary gamification of brainwave entrainment in which in-game objects and elements are used as visual stimulation transducers in conjunction with gameplay activities.

Figure 13:
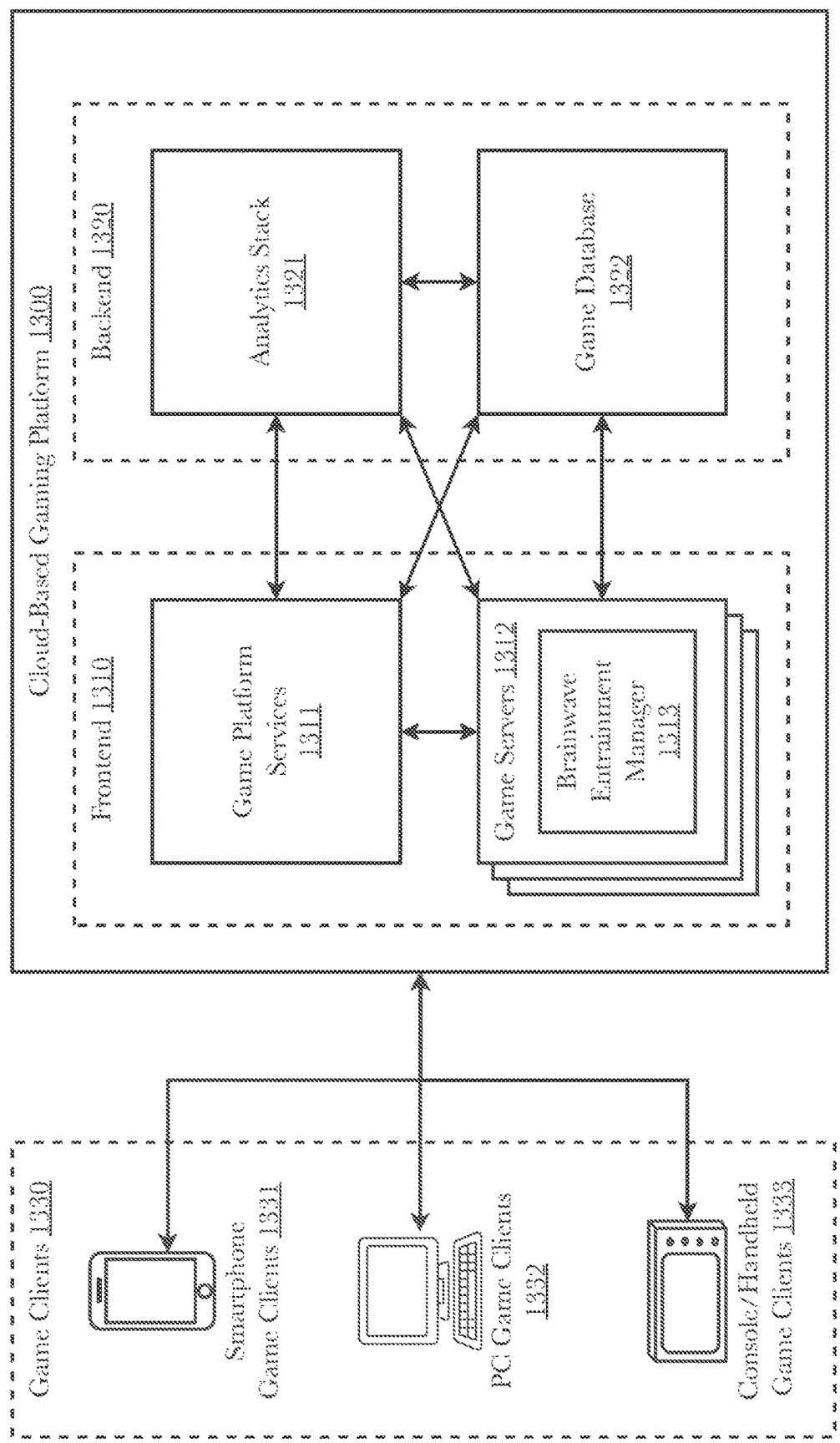

FIG. 13 is a block diagram showing an exemplary system architecture for a multi-person brainwave entrainment platform.

Figure 14:
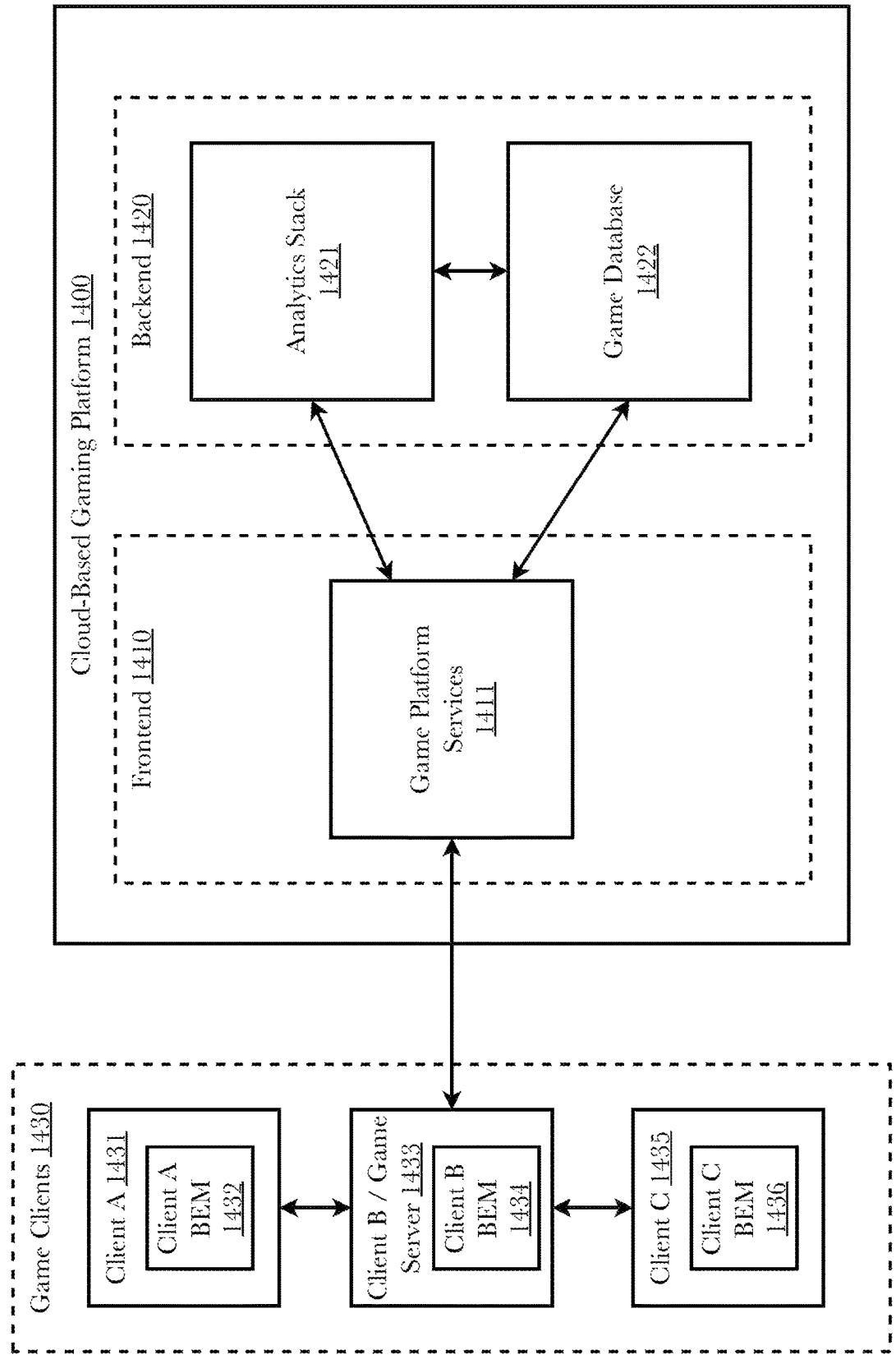

FIG. 14 is a block diagram showing an alternative exemplary system architecture for a multi-person brainwave entrainment platform.

Figure 15:
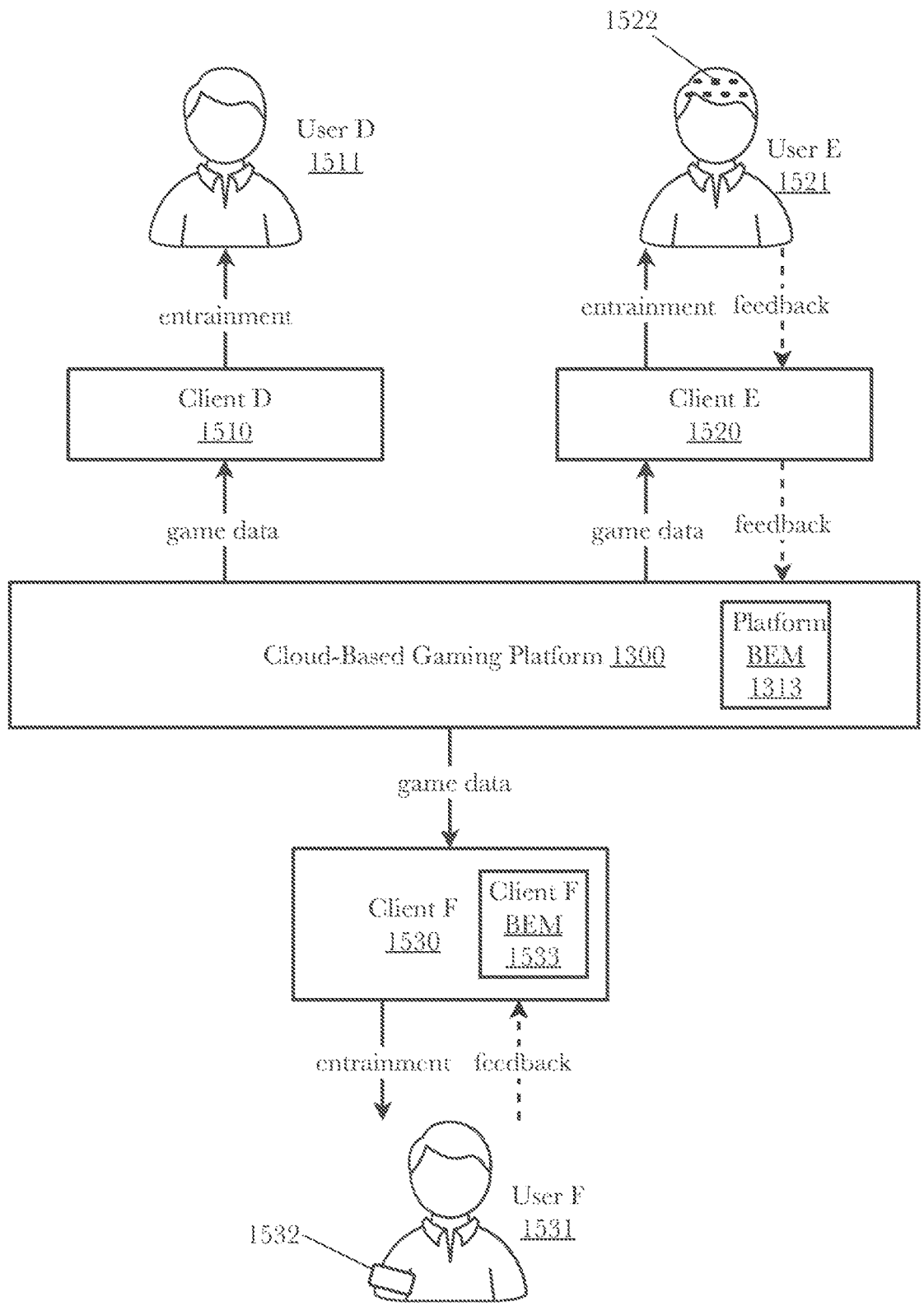

FIG. 15 is a block diagram showing an exemplary modes of connectivity with for different users of a brainwave entrainment platform.

Figure 16:
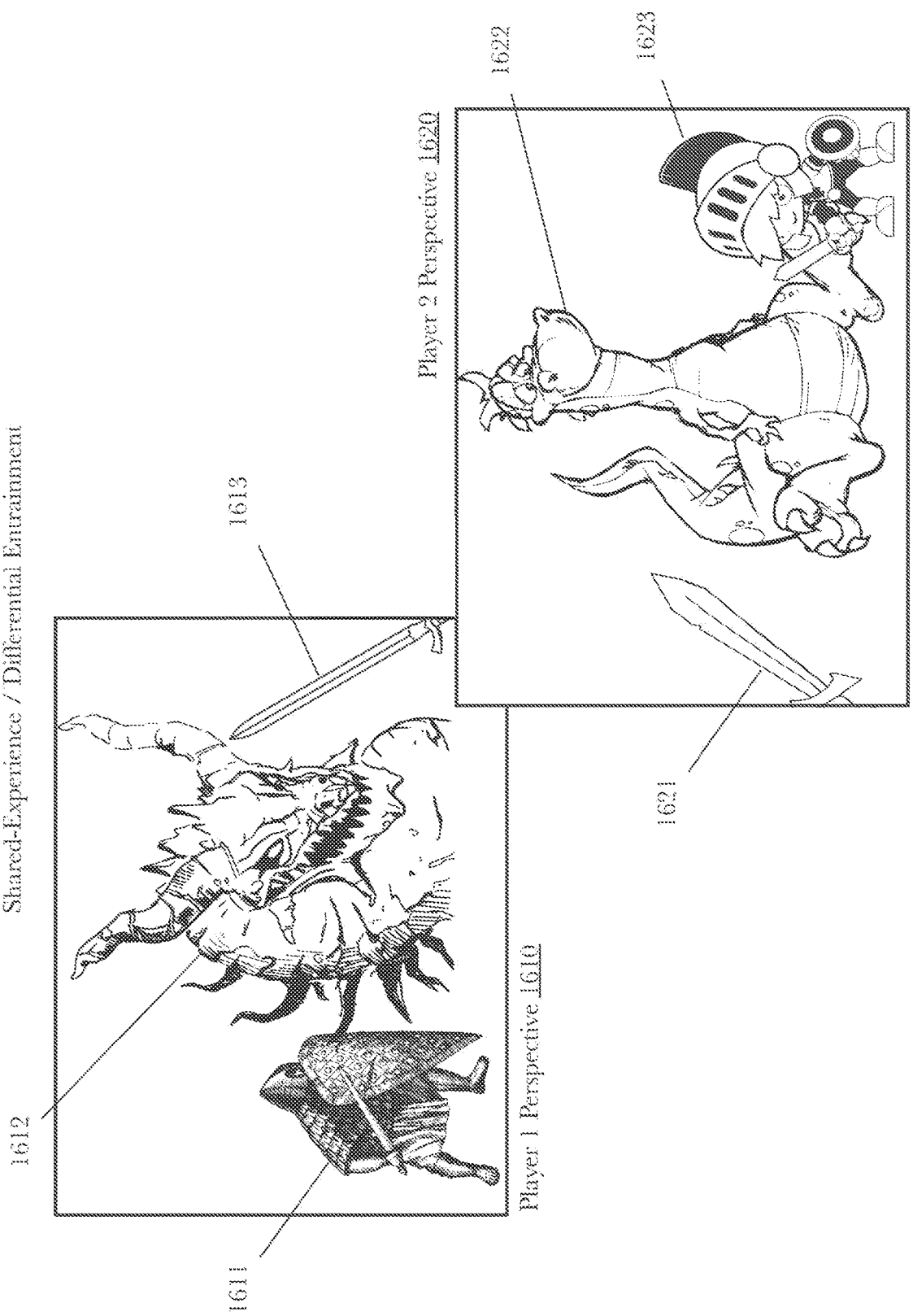

FIG. 16 is are exemplary perspective diagrams showing shared experience gameplay with differential realities and brainwave entrainments.

Figure 17:
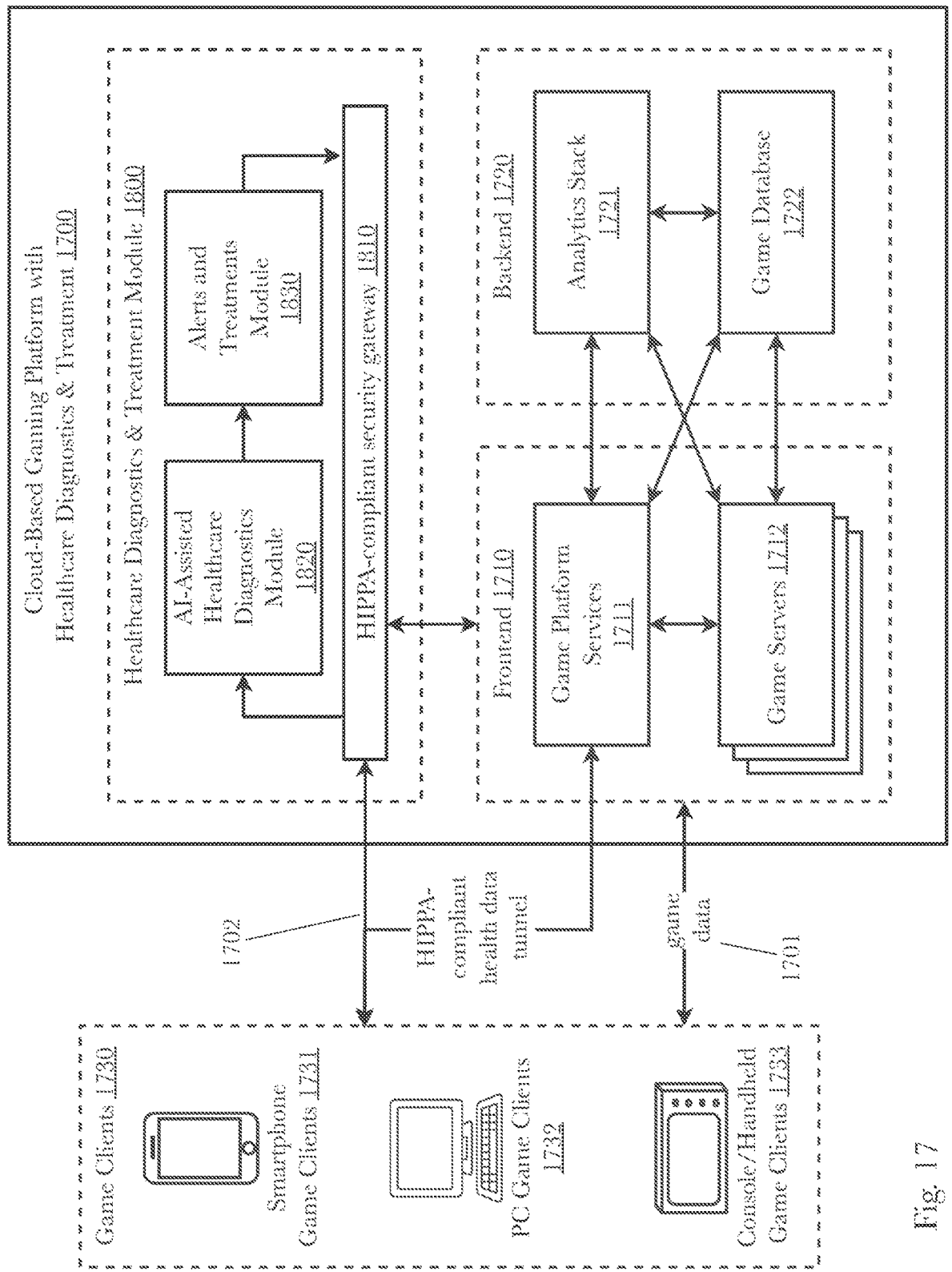

FIG. 17 is a block diagram showing an exemplary architecture for a cloud-based gaming platform with integrated healthcare diagnostics and treatment.

Figure 18:
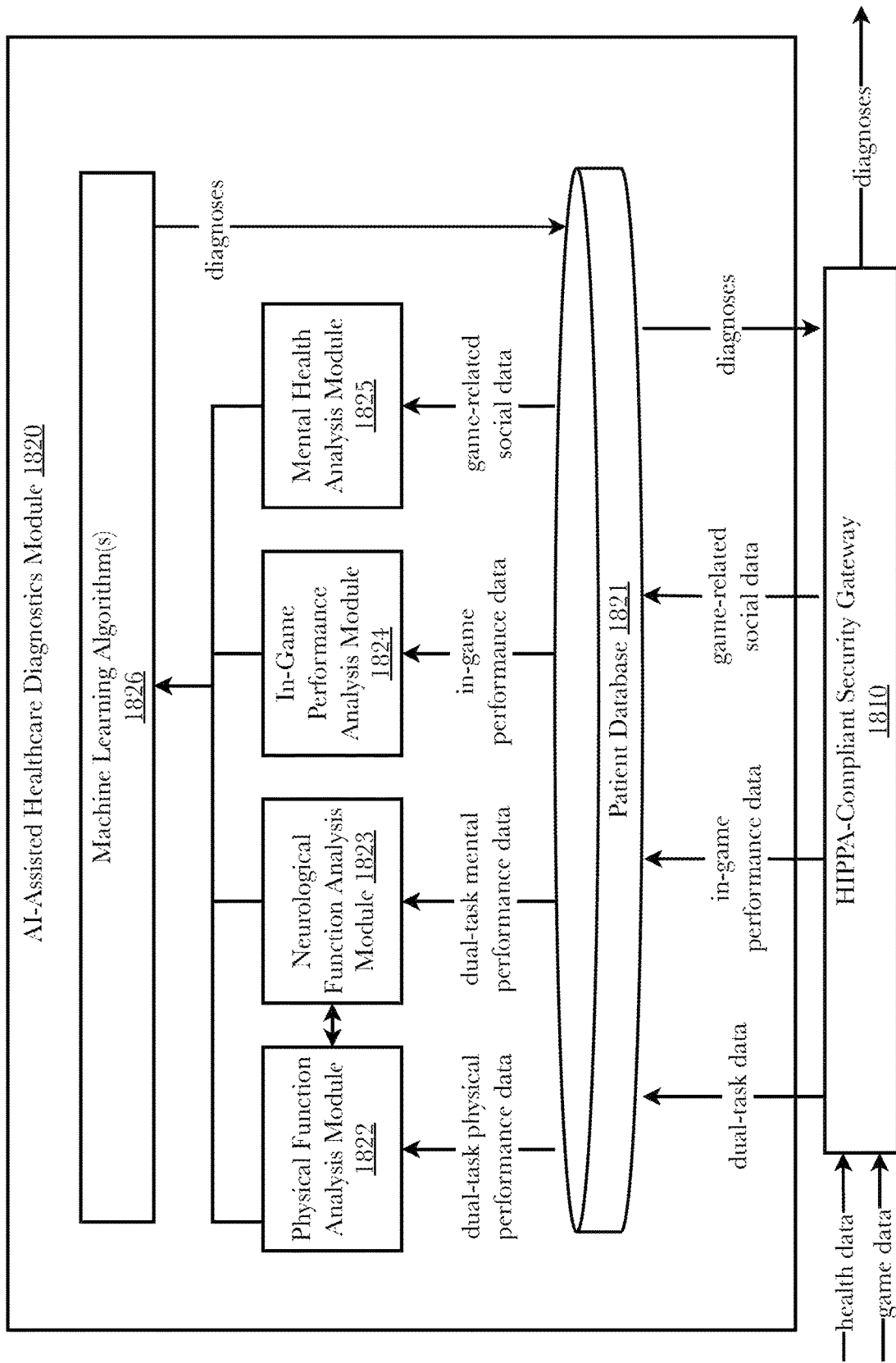

FIG. 18 is a block diagram showing an exemplary architecture for an AI-assisted healthcare diagnostics module aspect of a cloud-based gaming platform with integrated healthcare diagnostics and treatment.

Figure 19:
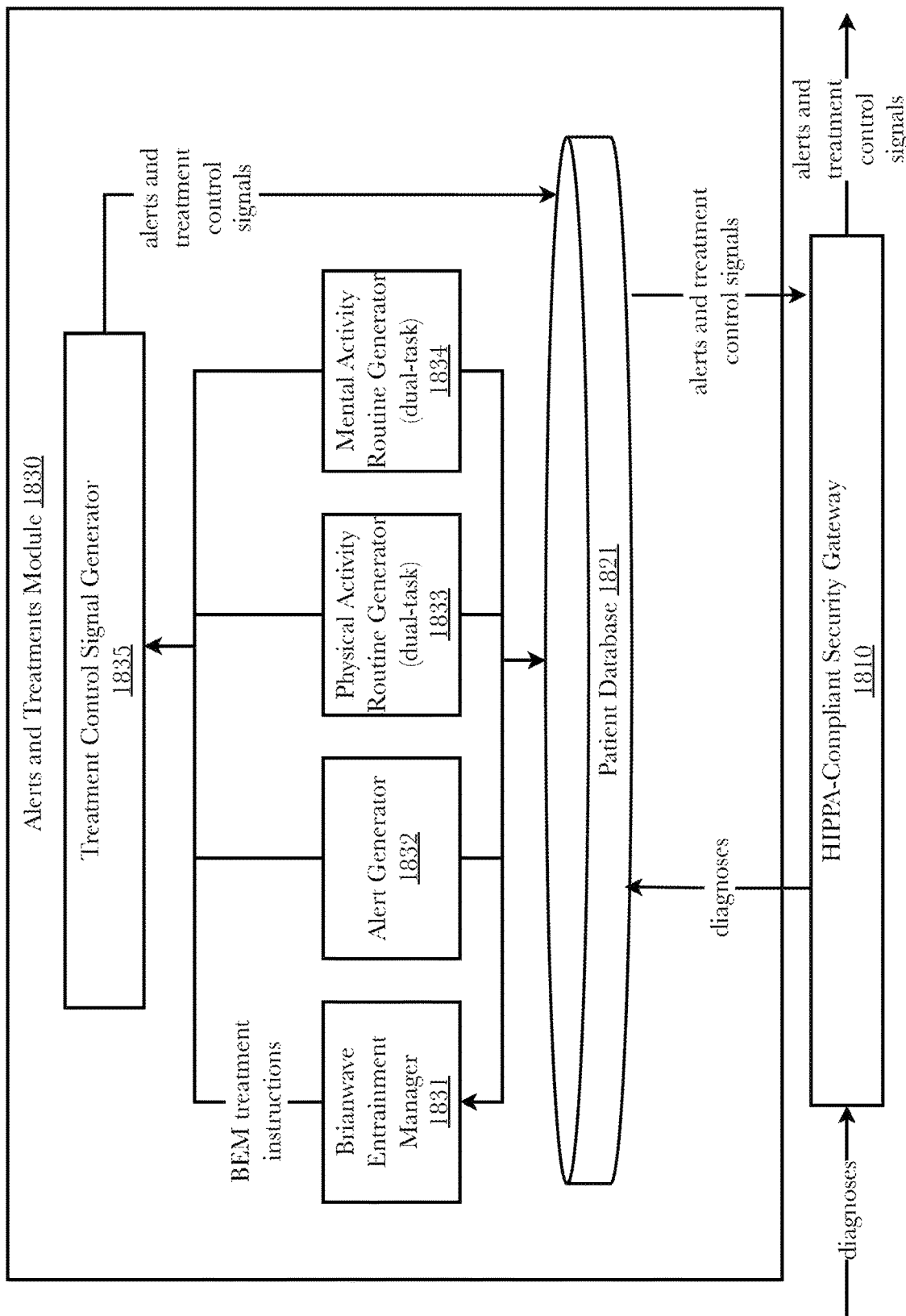

FIG. 19 is a block diagram showing an exemplary architecture for an alerts and treatments module aspect of a cloud-based gaming platform with integrated healthcare diagnostics and treatment.

Figure 20:
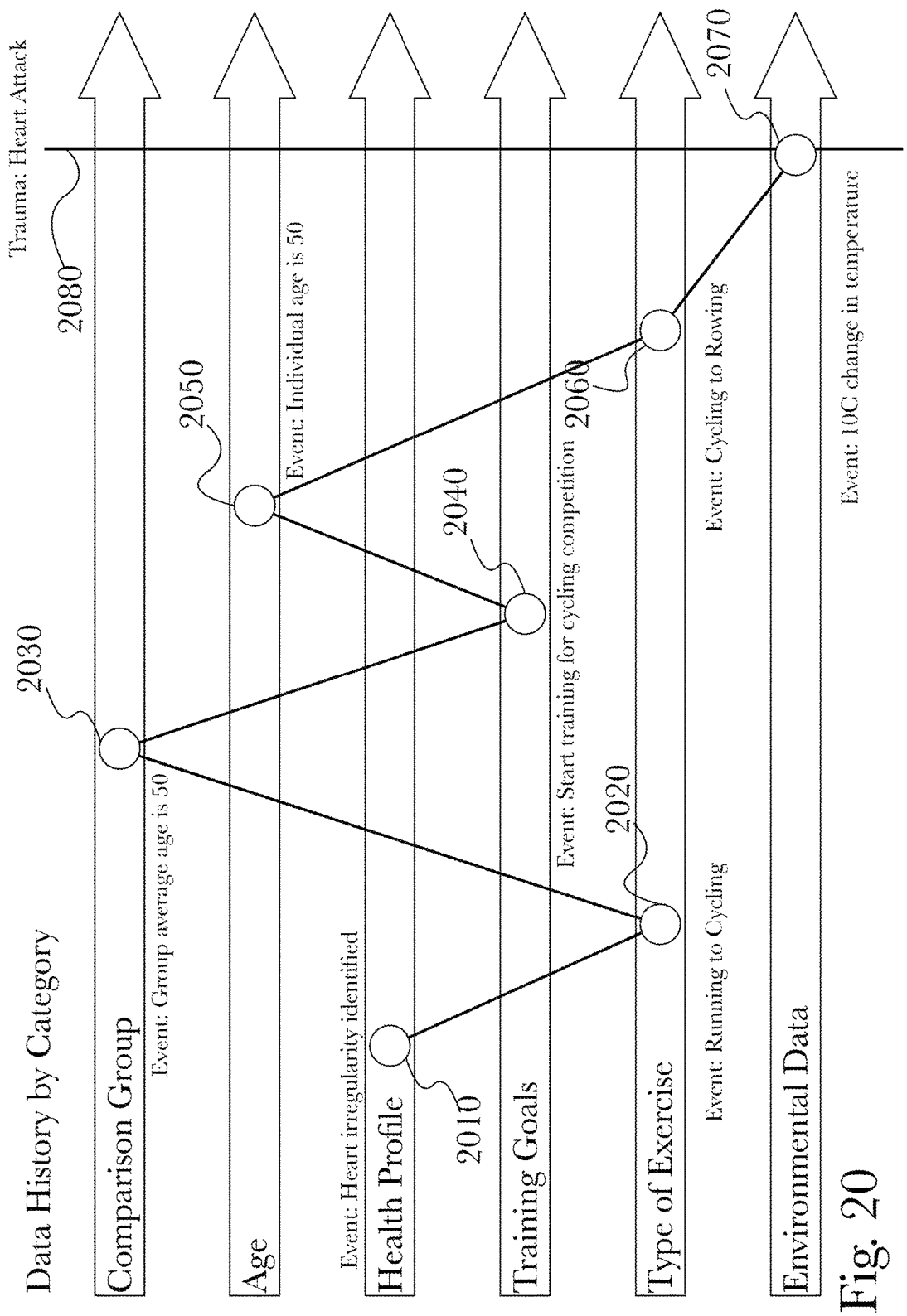

FIG. 20 is an exemplary diagram illustrating an exemplary application of machine learning to diagnose healthcare issues.

Figure 21:
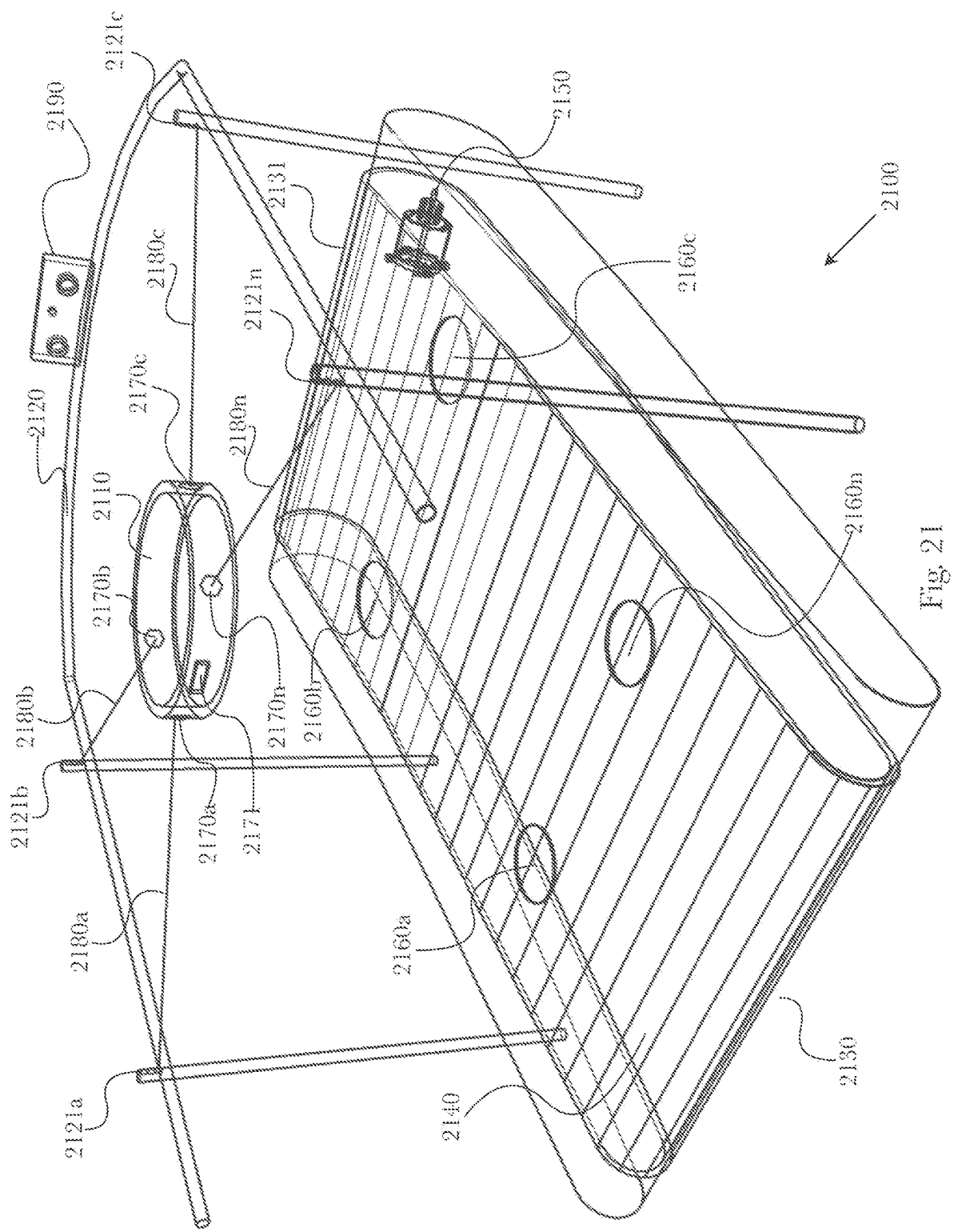

FIG. 21 is a diagram of an additional exemplary exercise machine configured to capture physical and mental performance data for a cloud-based gaming platform with integrated healthcare diagnostics and treatment.

Figure 22:
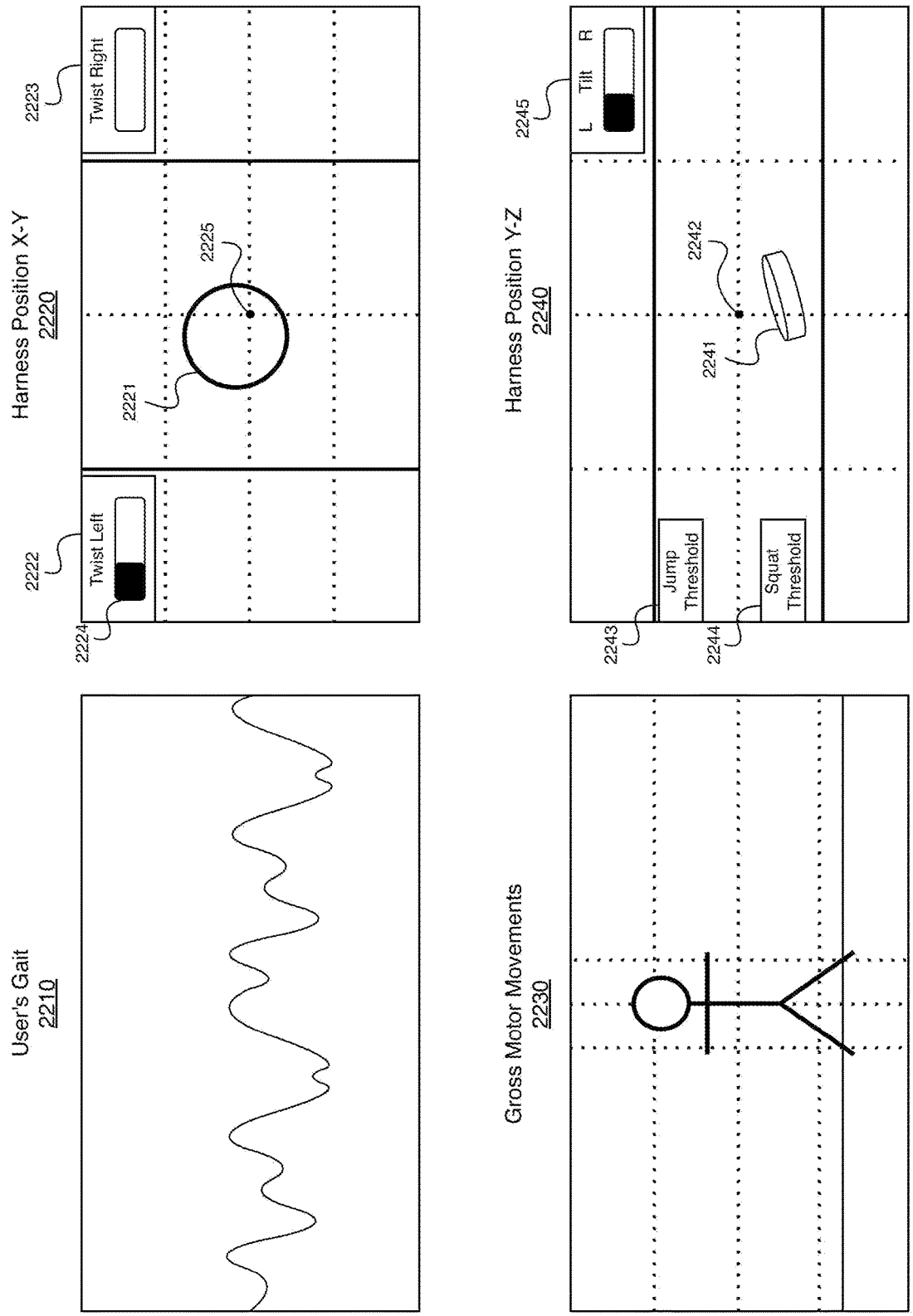

FIG. 22 is a diagram illustrating exemplary physical data that can be captured by an exercise machine compatible with a cloud-based gaming platform with integrated healthcare diagnostics and treatment.

Figure 23:
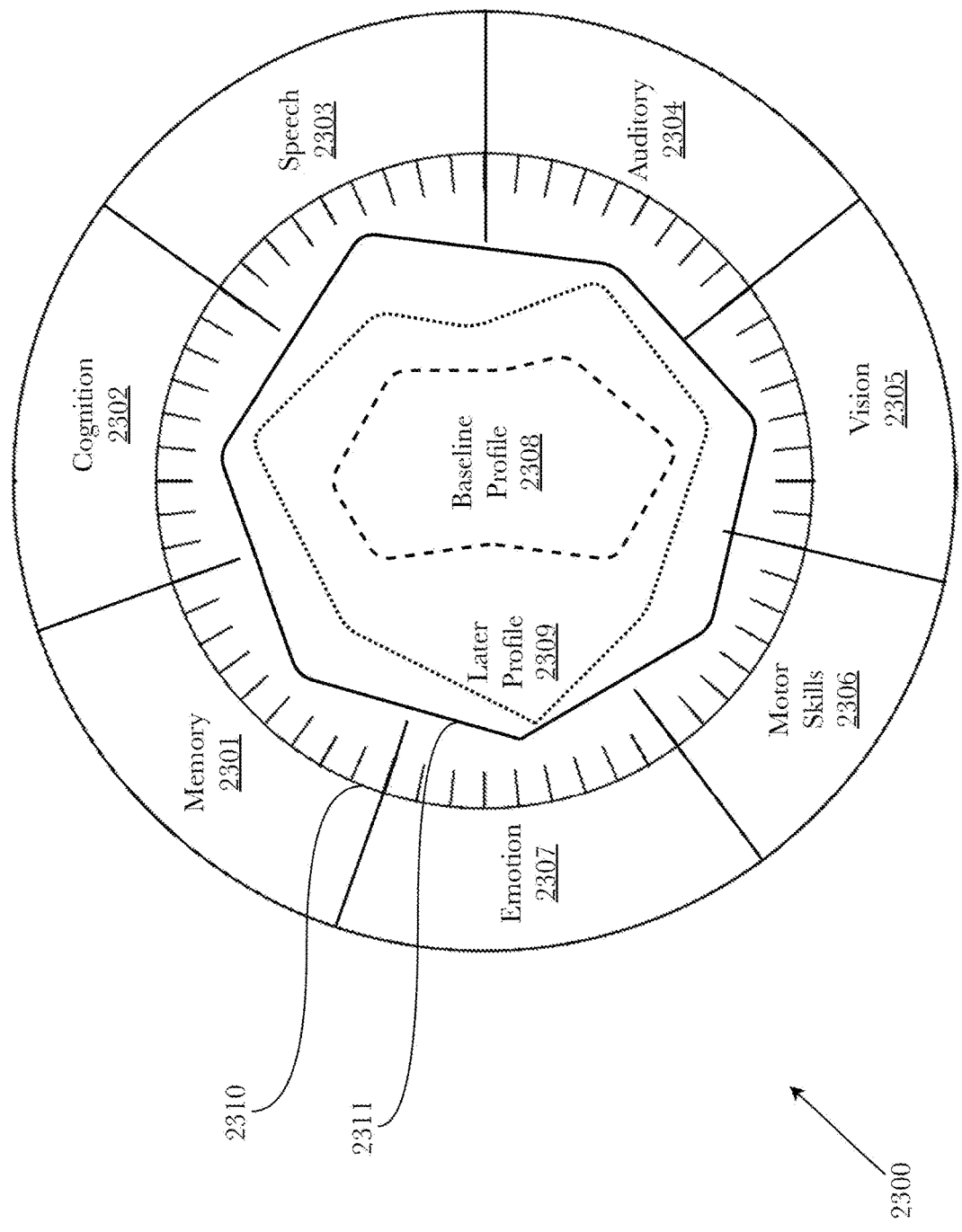

FIG. 23 is an exemplary composite functioning score spatial map showing diagnostics of ability in several physical and mental functional measurement areas.

Figure 24:
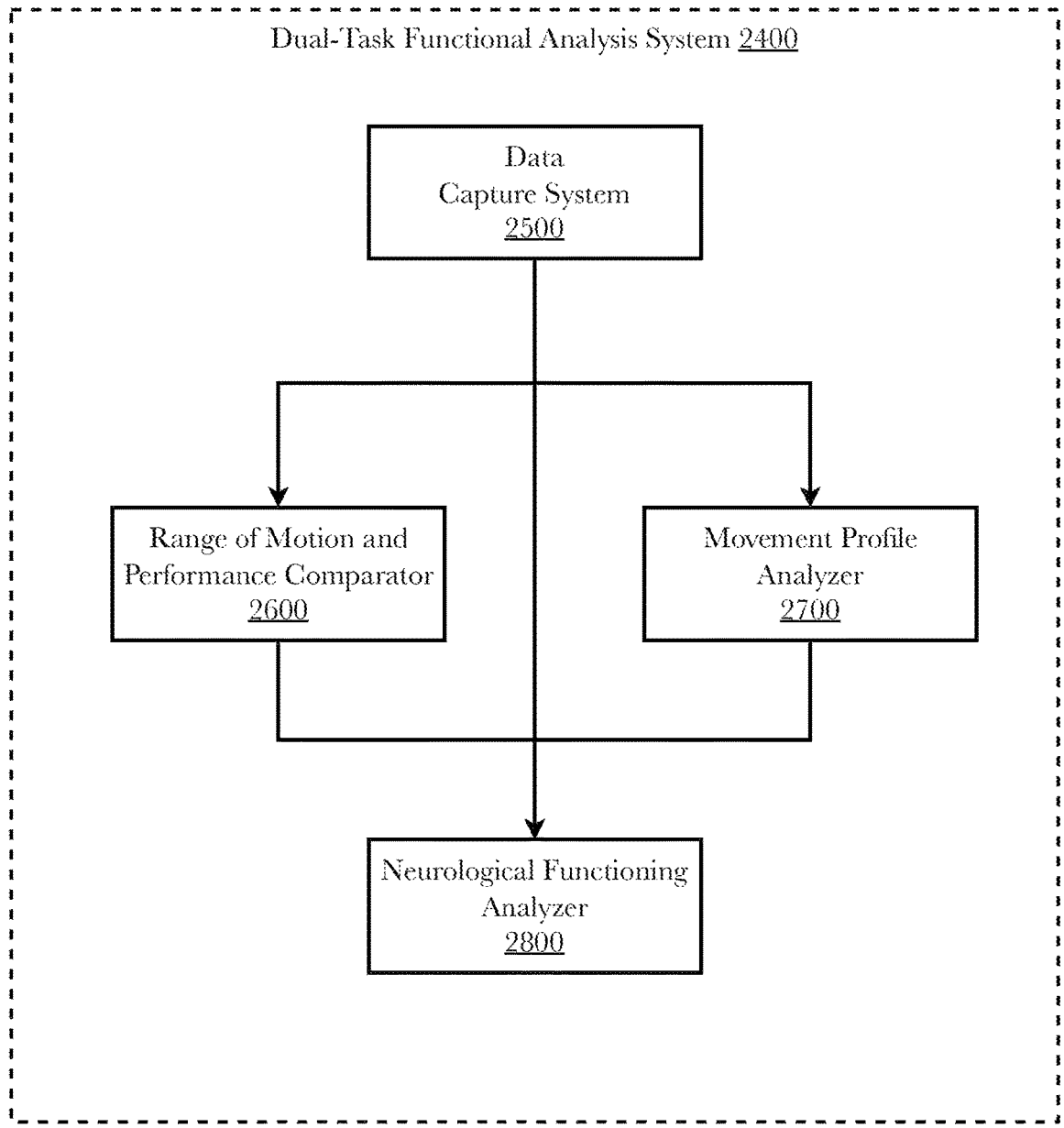

FIG. 24 is an exemplary system architecture diagram for a dual-task functional analysis system which may be used to capture and analyze physical and mental performance data for a cloud-based gaming platform with integrated healthcare diagnostics and treatment.

Figure 25:
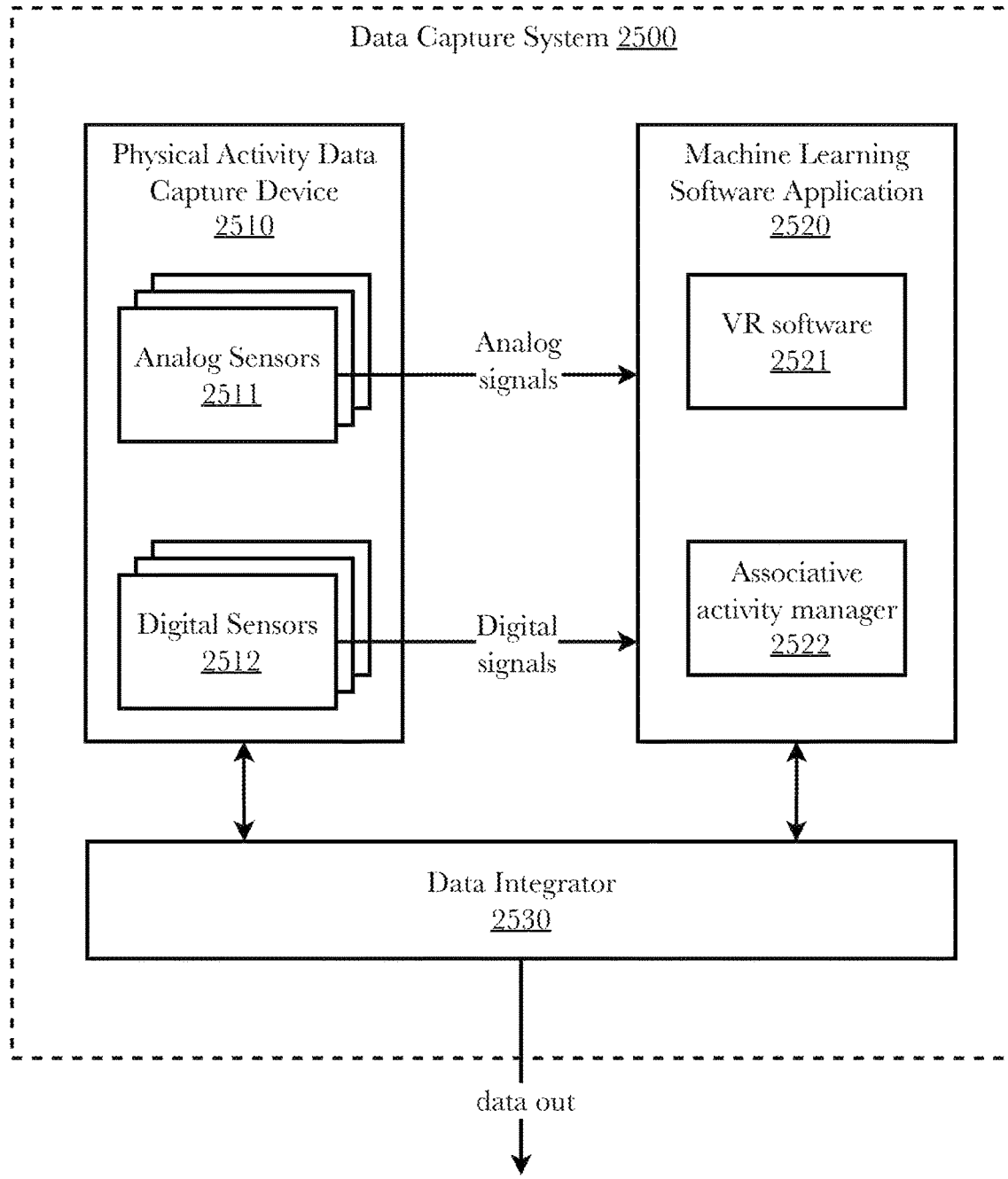

FIG. 25 is a system architecture diagram for a data capture system that may be used to capture data for a dual-task functional analyzer.

Figure 26:
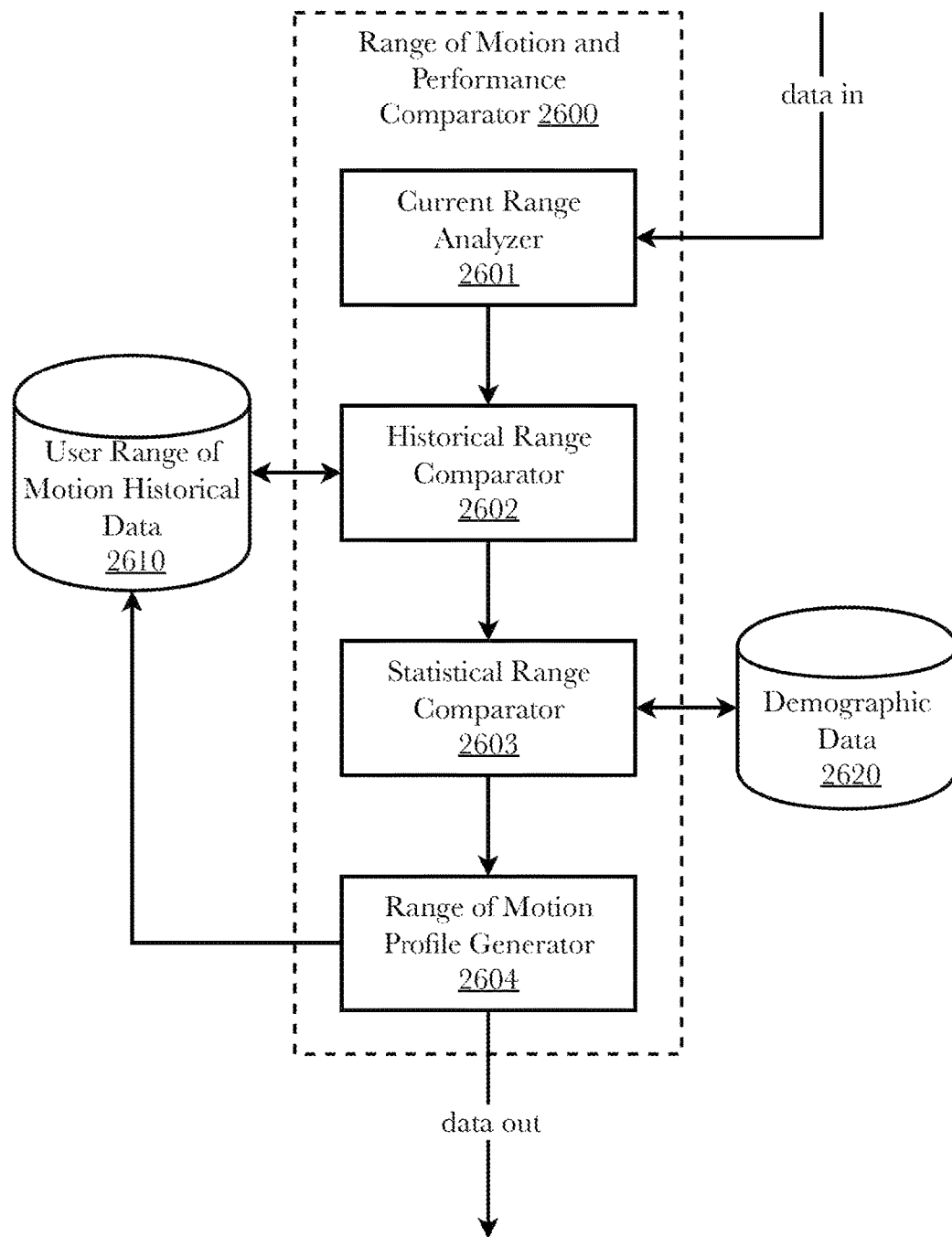

FIG. 26 is a system architecture diagram for a range of motion analyzer aspect of a dual-task functional analysis system.

Figure 27:
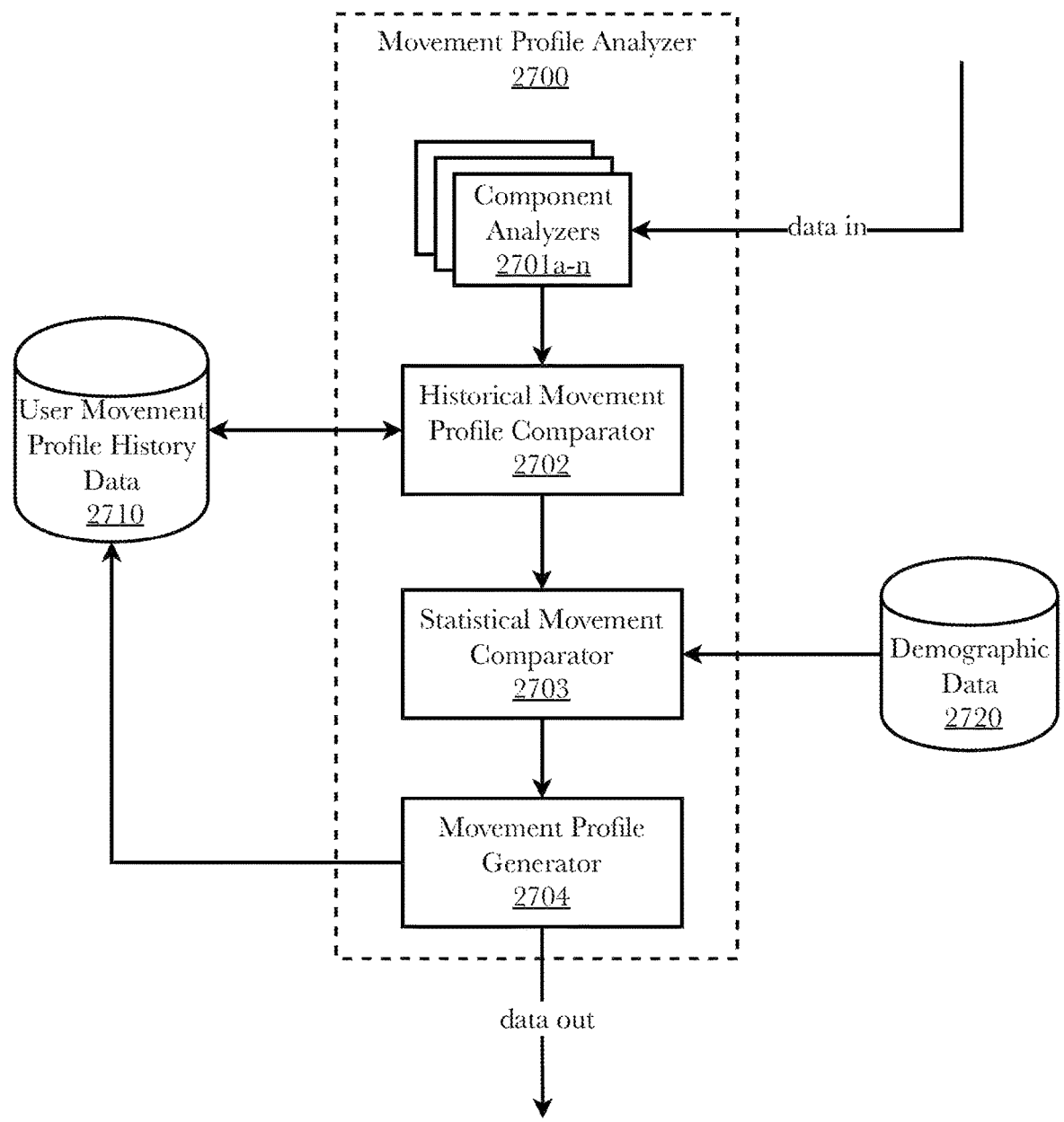

FIG. 27 is a system architecture diagram for the movement profile analyzer aspect of a dual-task functional analysis system.

Figure 28:
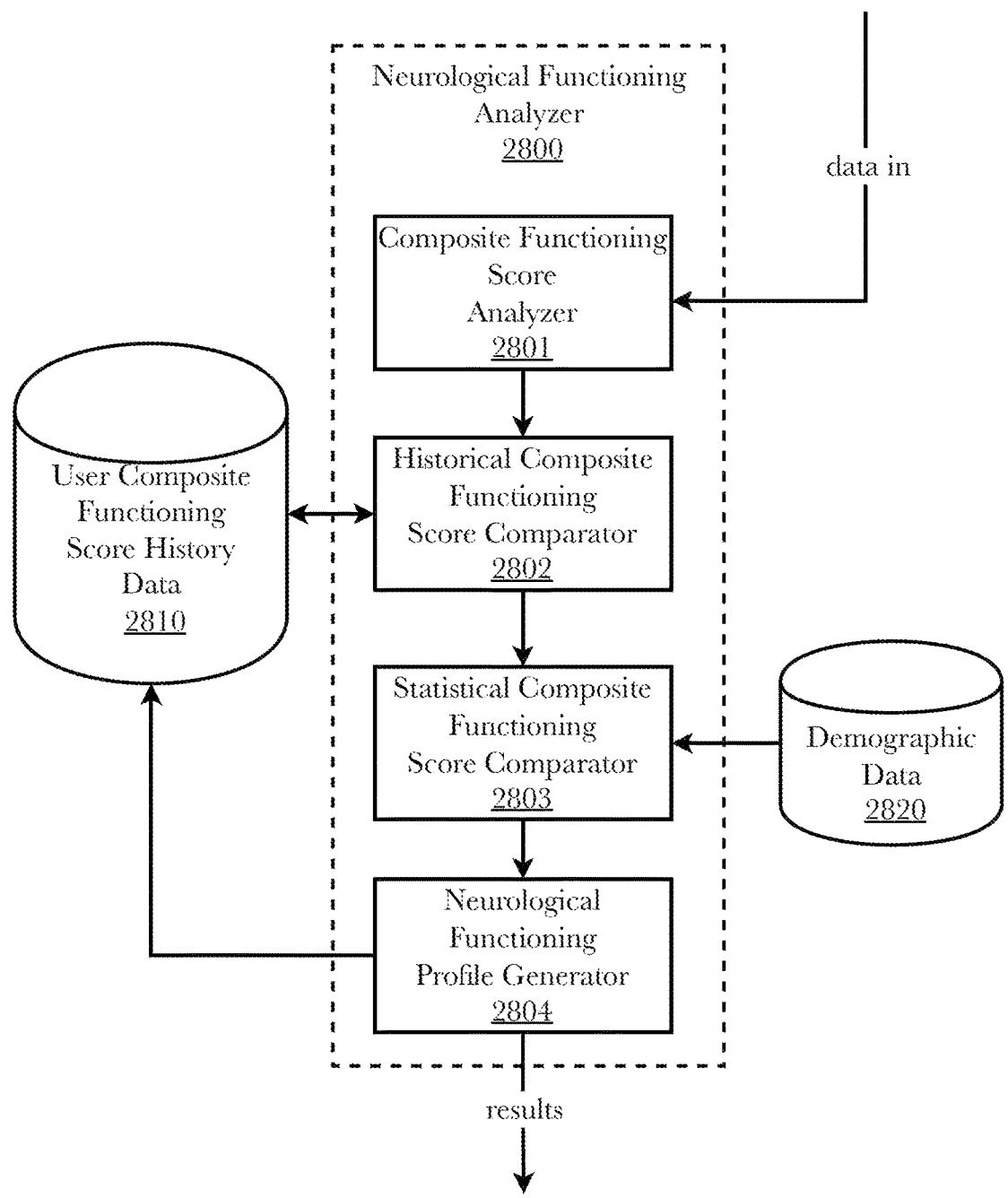

FIG. 28 is a system architecture diagram for a neurological function analyzer aspect of a dual-task functional analysis system.

Figure 29:
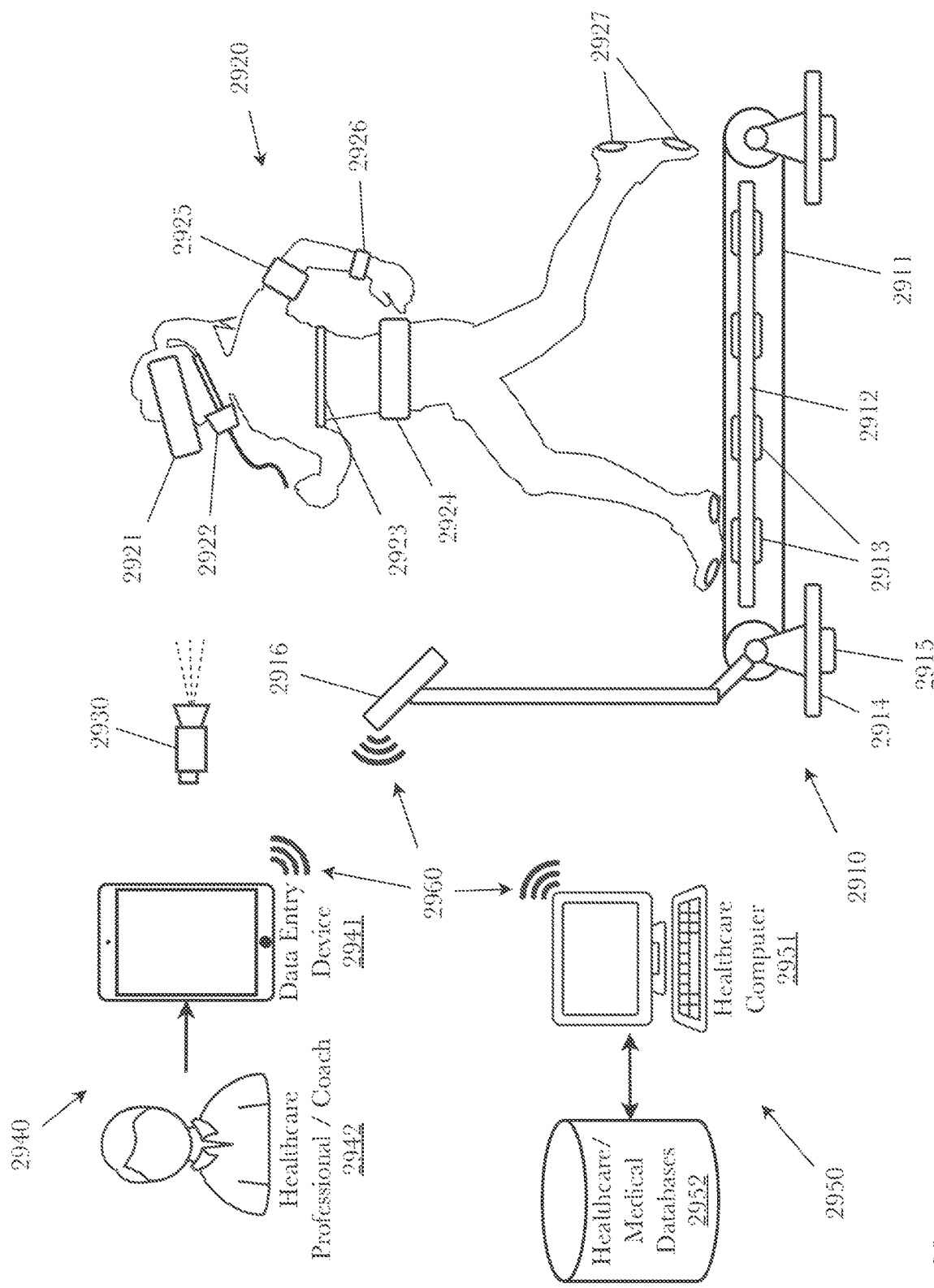

FIG. 29 is a diagram showing exemplary health data collection devices usable for collection of health data.

Figure 30:
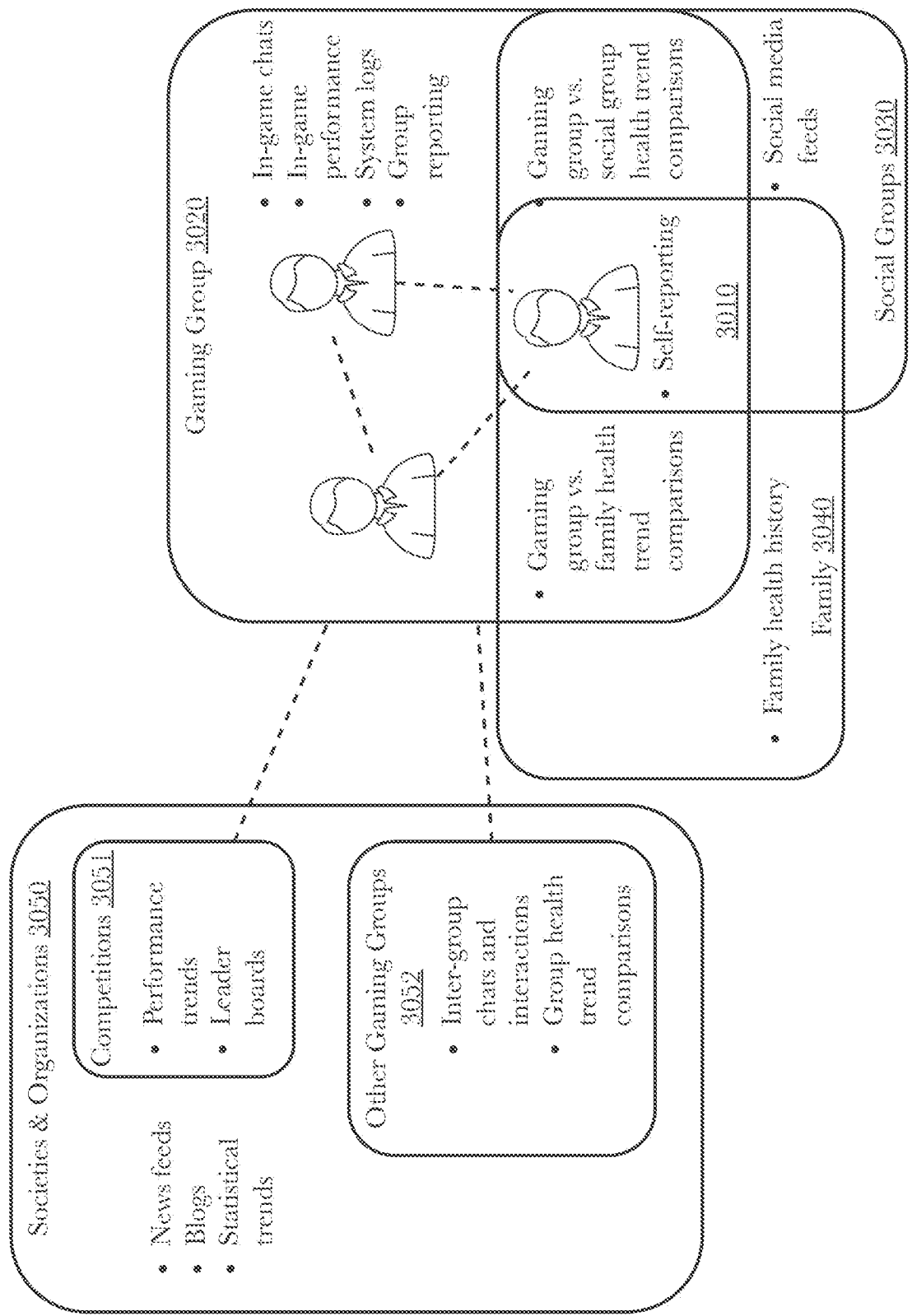

FIG. 30 is a diagram showing exemplary health-related social data collection.

Figure 31:
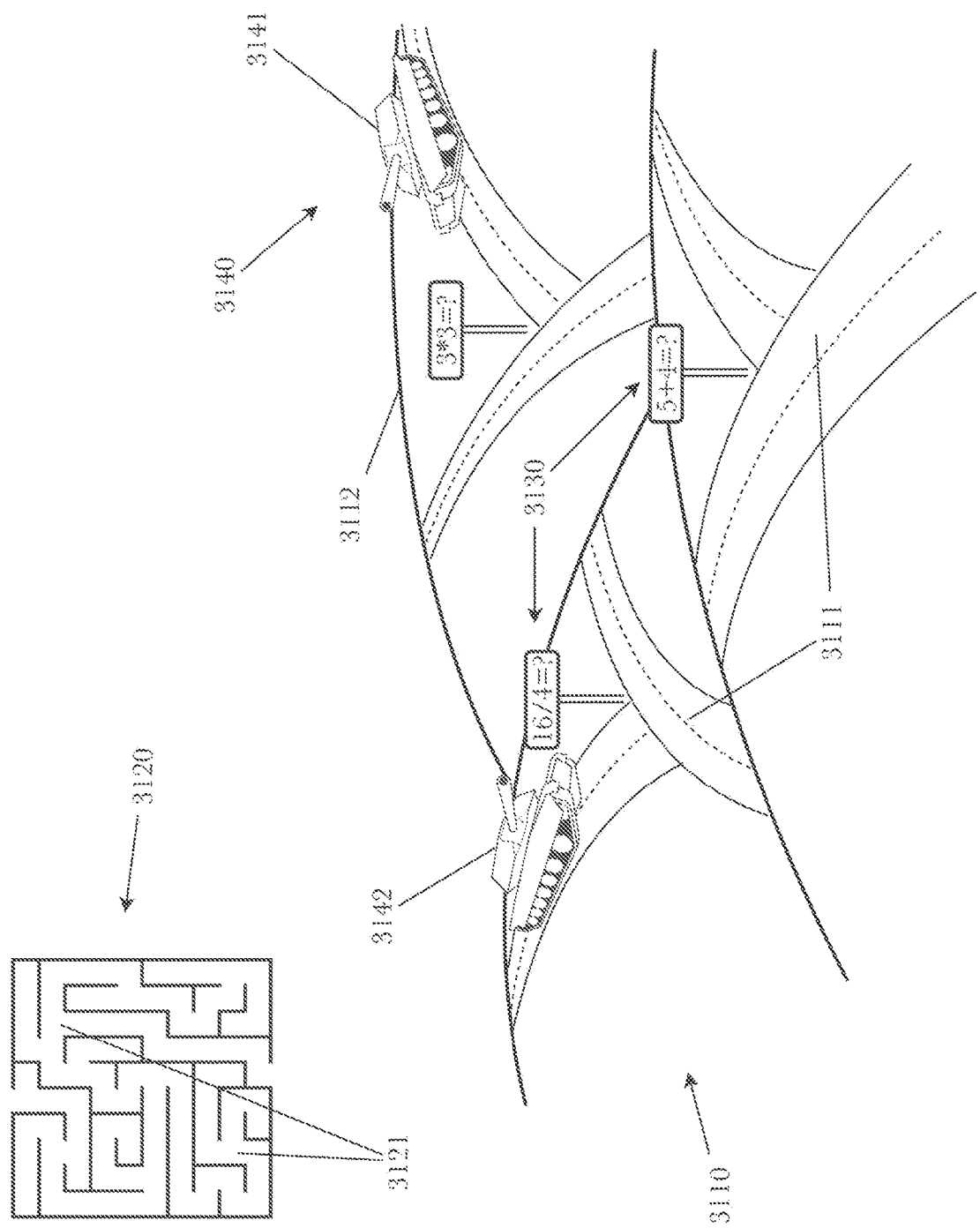

FIG. 31 is diagram showing exemplary methods for in-game data collection.

Figure 32:
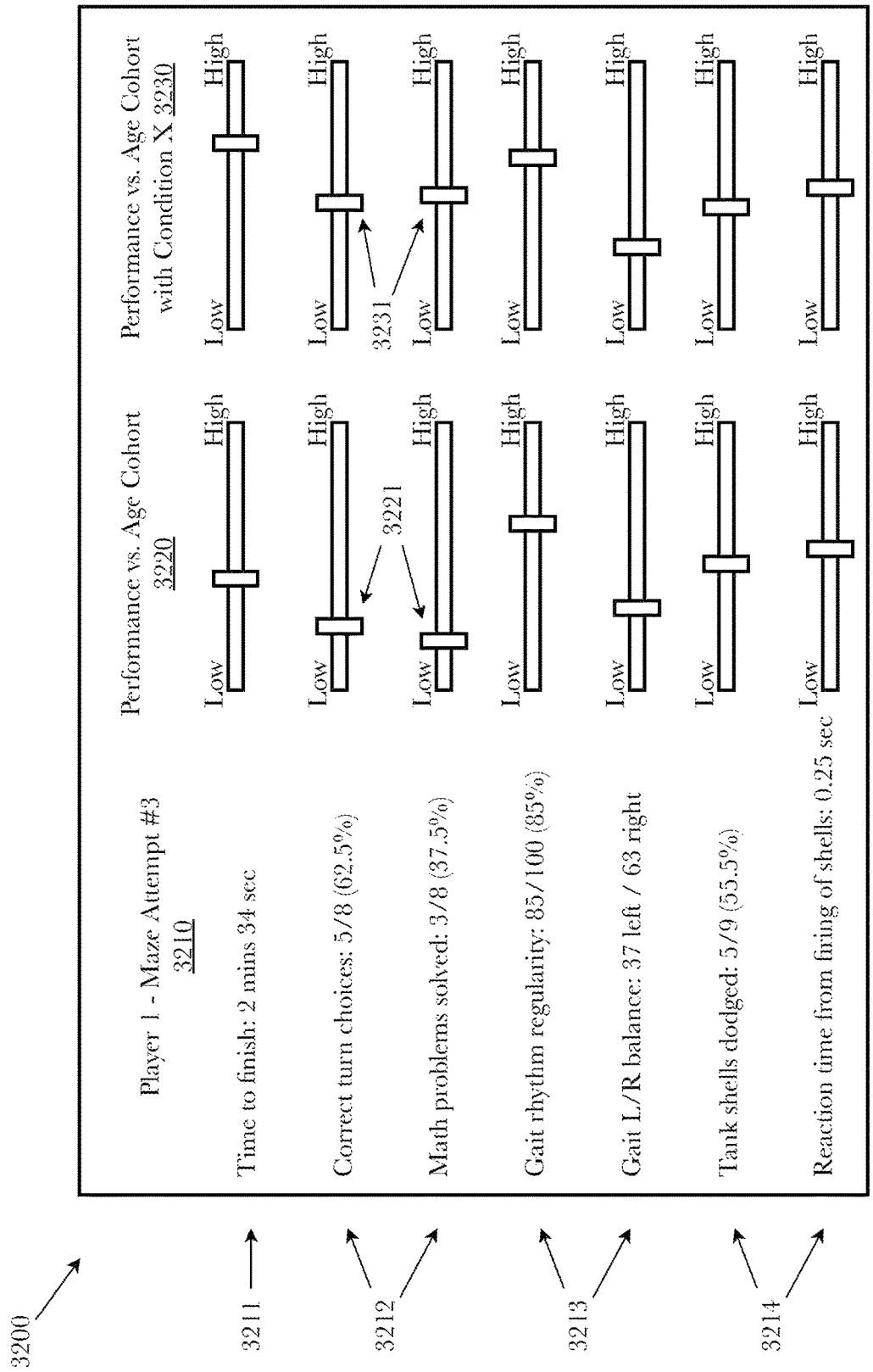

FIG. 32 is diagram showing exemplary data from in-game data collection.

Figure 33:
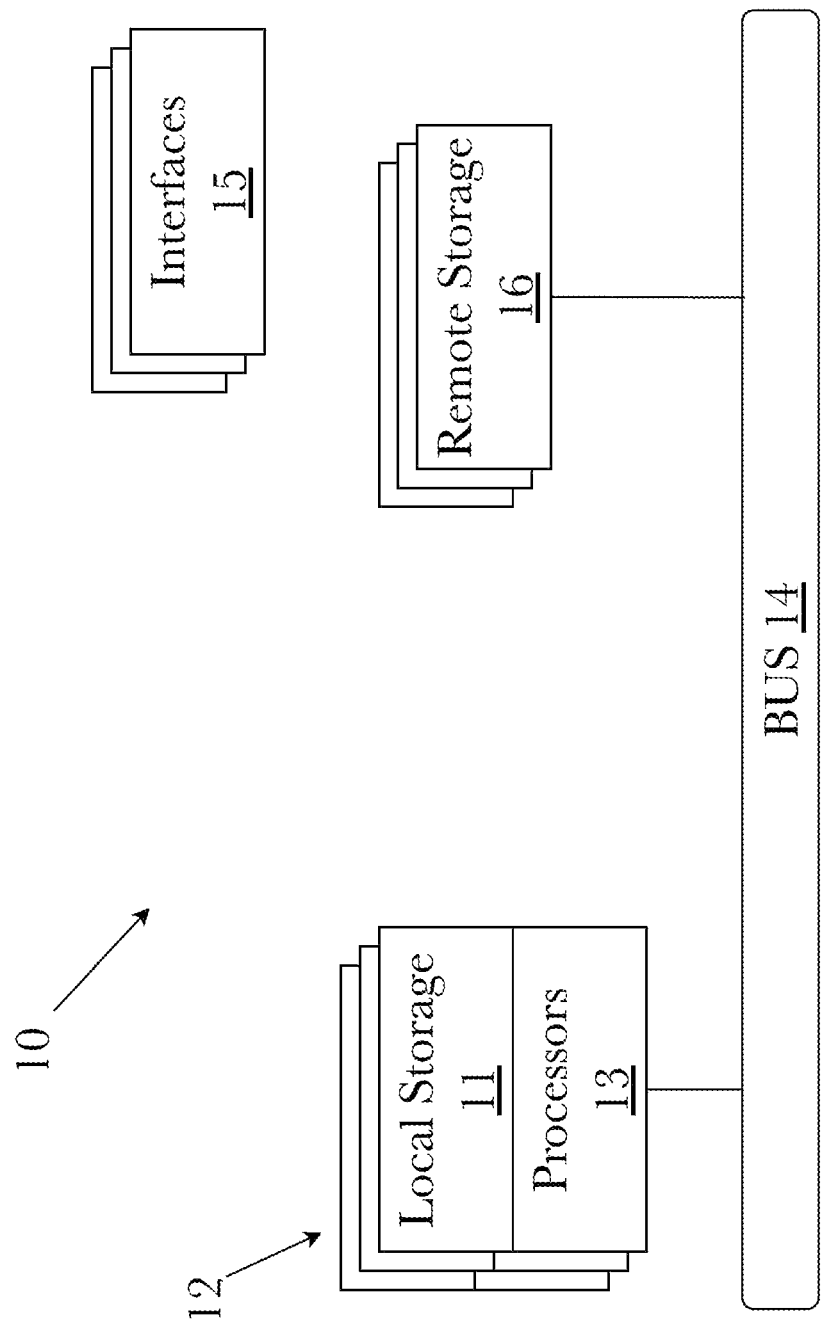

FIG. 33 is a block diagram illustrating an exemplary hardware architecture of a computing device.

Figure 34:
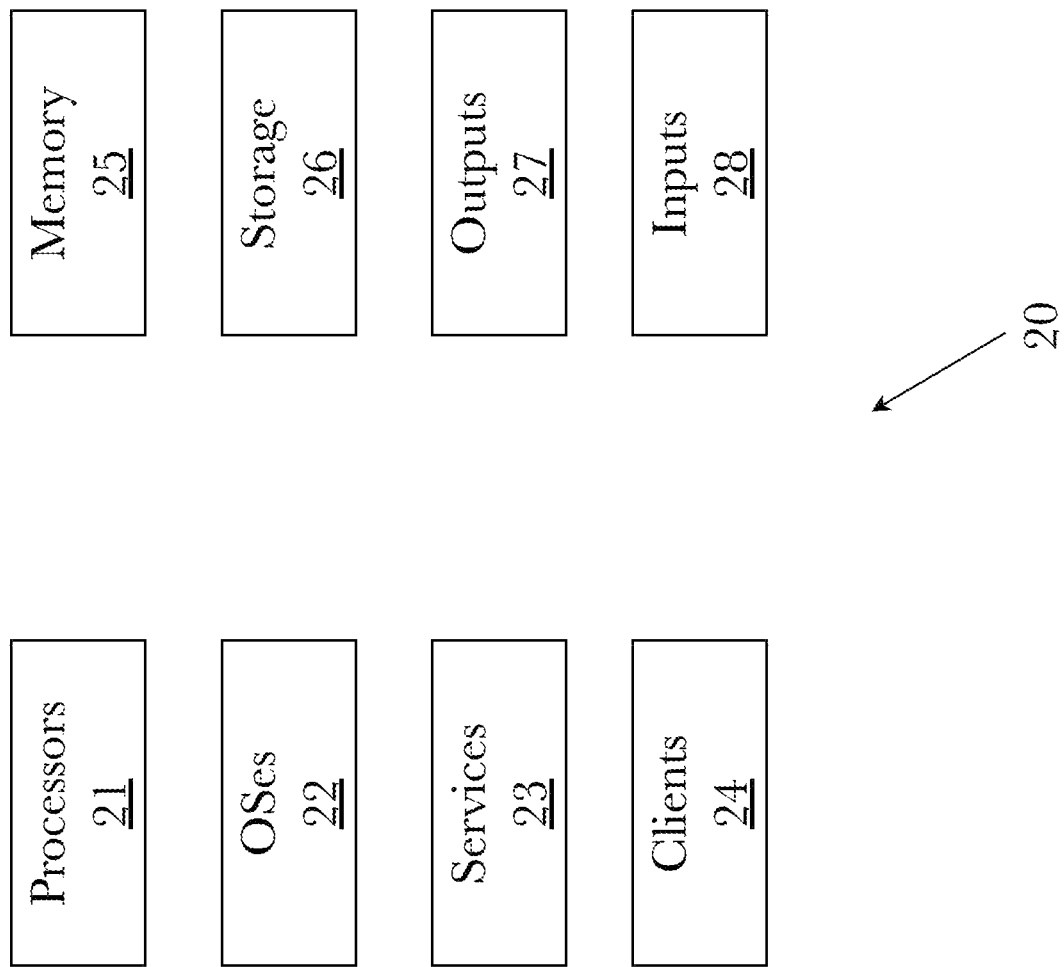

FIG. 34 is a block diagram illustrating an exemplary logical architecture for a client device.

Figure 35:
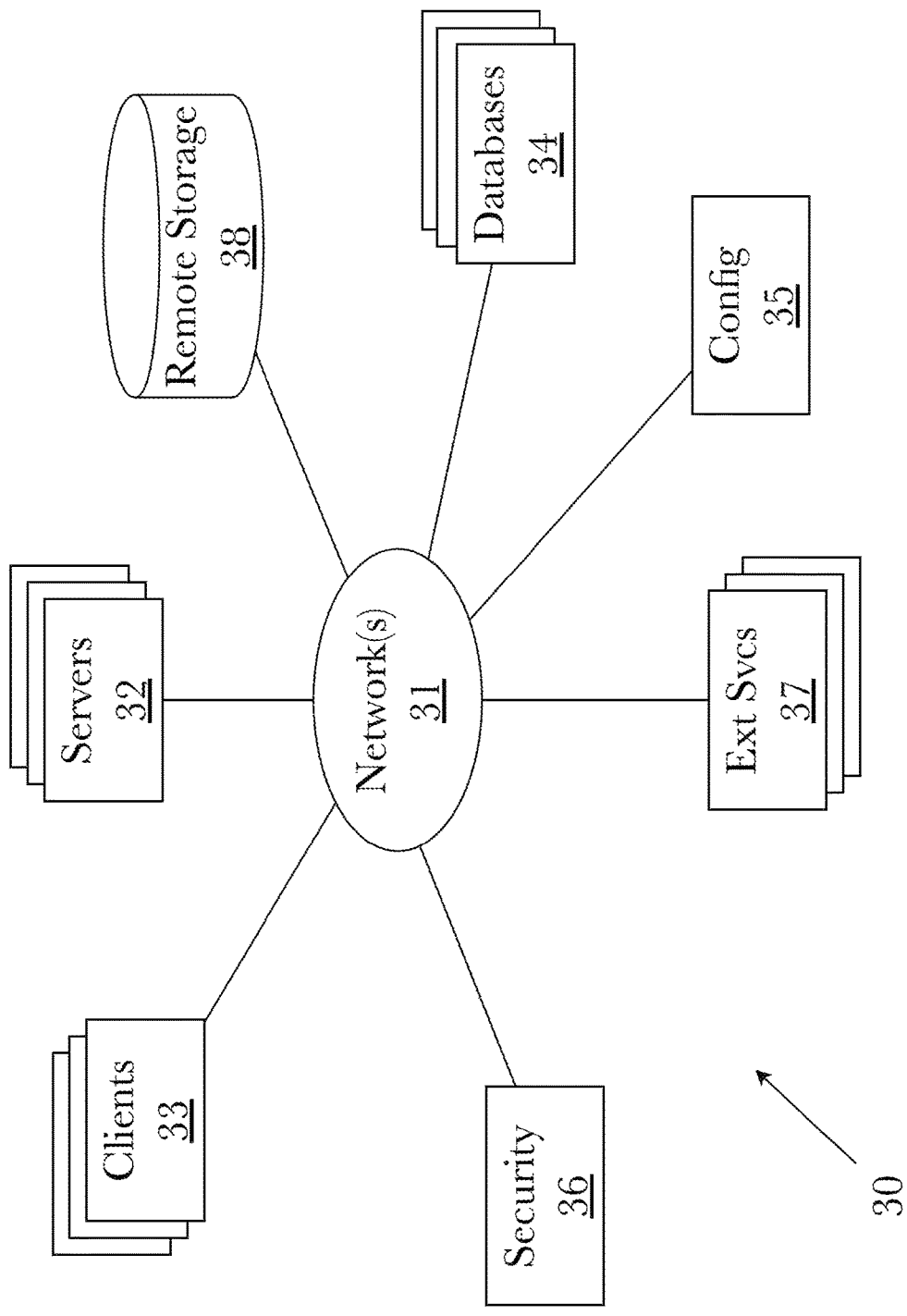

FIG. 35 is a block diagram showing an exemplary architectural arrangement of clients, servers, and external services.

Figure 36:
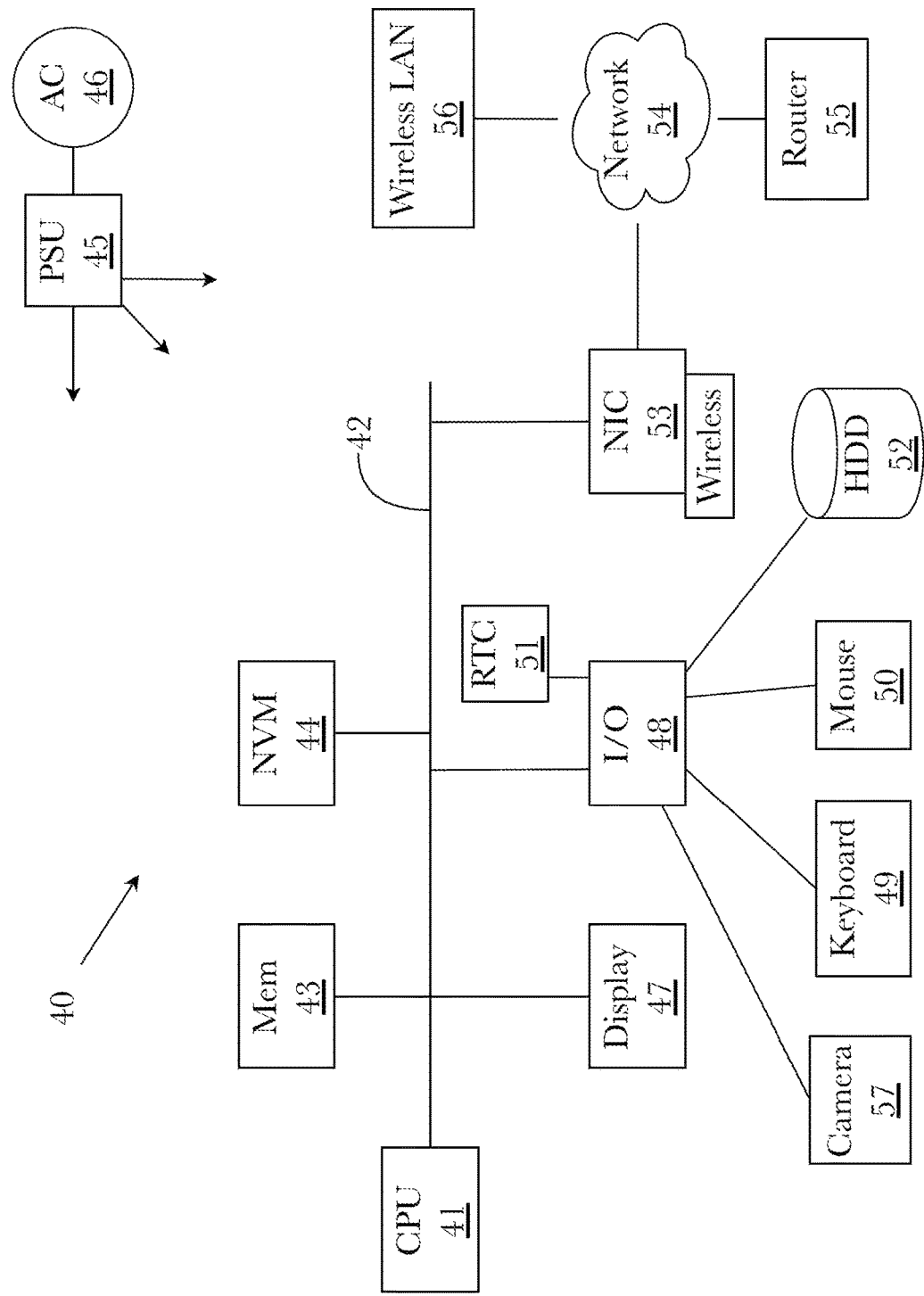

FIG. 36 is another block diagram illustrating an exemplary hardware architecture of a computing device.

DETAILED DESCRIPTION OF THE DRAWING FIGURES

The inventor has conceived, and reduced to practice, a system and method for a cloud-based gaming platform with integrated healthcare diagnostic and treatment capabilities. In an embodiment, the system and method comprise a cloud-based gaming platform comprising a frontend accessible from various game clients which operates a gaming environment on one or more game servers, a backend that provides the game database and analytics used by the game servers to operate the gaming environment, and a healthcare diagnostics and treatment module integrated into the platform comprising a HIPPA-compliant security gateway, an AI-assisted healthcare diagnostics module, and an alert and treatments module. Exercising on an exercise machine compatible with the cloud-based gaming platform entertains the user while simultaneously capturing data about the user's physical and mental performance which can be used to diagnose medical conditions and, depending on configuration, implement treatment regimens comprising exercise routines and mental simulation via tasks in the gaming environment.

Advancements in and virtual reality systems and environments have created new opportunities for immersive virtual experiences. However, this potential for immersive virtual experiences has not been used for much beyond computer gaming. Further, while virtual reality gaming platforms exist, including multi-person gaming platforms, none are capable of gathering health-related data about players during operation. There is a great deal of health-related data that could be gathered from computer gaming systems, but which is not captured because systems are not configured to capture that data as health-related data. Further, specialized equipment can be utilized to expand and enhance the health-related data captured as an invisible and seamless integration with computer gaming systems. Multi-player gaming expands the types of health-related data that can be collected to include social interactions such as in-game chats and messaging between team players through the online gaming system. Systems and methods for capturing this health-related data during game play are described herein.

As lifespans have improved in the past few decades, particularly in more developed countries, the mean and median age of populations have increased. The greatest risk factor for neurodegenerative diseases is aging, so older persons are more likely to suffer from degenerative diseases and conditions affecting the nervous system such as amyotrophic lateral sclerosis, Parkinson's disease, Alzheimer's disease, fatal familial insomnia, Huntington's disease, Friedreich's ataxia, Lewy body disease, and spinal muscular atrophy. It has been estimated that some 20-40% of healthy people between 60 and 78 years old experience discernable decrements in cognitive performance in one or more areas including working, spatial, and episodic memory, and cognitive speed. Early stages of neurodegenerative diseases are difficult to detect, the causes of such diseases are not well understood, and treatments for such diseases are non-existent.

Without using one of the costly brain scan technologies, it remains difficult to detect, assess, and treat poor functioning of the nervous system, whether such poor functioning is due to injury to the brain, neurodegenerative disease, psychological or physical trauma, or changes in brain chemistry, diet, stress, substance abuse, or other factors. For certain neurological conditions, such as Chronic Traumatic Encephalopathy (CTE), none of the current brain scan technologies are able to reliably capture diagnostic data. Other neurological deficits and conditions can be evaluated or diagnosed using assessments using readily available equipment and observational analysis, such as the Cognitive Performance Test (CPT) and Timed Up and Go Test (TUG) but lack the sensitivity suitable for nuanced or early deficit detection. Each of these types of poor nervous system function can impact different parts of the brain and/or nervous system in different ways. Due to the complexity of interactions in the nervous system and the brain's ability to adapt its function in many areas, it remains difficult to detect poor functioning and to identify which neurological functions and anatomical aspects and regions are impacted early enough to implement an effective treatment protocol.

However, recent research studies have demonstrated that physical activity, especially aerobic exercise, can improve neurogenesis and other neurological functions, whether related to physical brain and nervous system impairments or mental health/emotional issues. In addition, evolutionary biologists have hypothesized that early humans began their cognitive revolution when they ventured into the African savannah and started walking upright. In fact, more recent research studies on the cerebellum, an ancient part of the brain that coordinates the motor control, have discovered unexpected connections between the cerebellum and other parts of the brain. Specifically, according to a team of researchers from the University of Washington, only 20 percent of the cerebellum connections was dedicated to areas involved in physical motion, while 80 percent was connected to areas involved in functions such as abstract thinking, planning, emotion, memory and language. The cerebellum doesn't actually execute tasks like thinking, just as it doesn't directly control movement. Instead, it monitors and coordinates the brain areas that are doing the work and makes them perform better.

Therefore, simultaneous testing of primary physical tasks such as walking or running and the associative activities that include various mental, other physical activities as well as emotional experiences (commonly known as a dual task assessment), and the correlation of results therefrom can be used to evaluate specific neurological functional areas to create a profile of relative neurological functioning and see where deficiencies may be present. Therefore, changes in a person's walking gait while the person is engaged in other associative activities like solving a logic puzzle could be analyzed and compared against the normal or average dual-tasking costs of the same population group for relative functioning as well as anomalies. Such anomalies for the given brain functions or regions could be indicative of abnormal central nervous system functions. Further, the combination of the dual-tasked physical and associative activities can help identify the abnormally-performing neurological functions or even help isolate affected neurological regions. For example, a walking gait/logic puzzle dual-task activity may indicate normal functioning in a given individual, indicating that autonomous physical activity and cognition are not affected. However, in the same individual another dual task of walking and listening within a virtual reality (VR) environment may result in gait changes or a complete stop of the walk as the neurological functions required for these tasks are different from walking and logic. In this case, it may indicate that there may be injury to or degeneration of the auditory cortex of the temporal lobe, potentially informing further diagnostic procedures. As a result, a system combining numerous combinations of various dual-tasking activities, covering all neurological functions or regions, may be able to evaluate, detect, and treat neurological deficits and conditions even before they become noticeably symptomatic. For individuals for whom symptoms are already present, such a system can evaluate and track changes over time, and potentially slow down or reverse the progression of such deficits and conditions.

Using this same dual-tasking analysis, it is also possible to evaluate, detect, and treat neurological conditions and changes involving mental health and emotional issues. For example, elevated heart rate, elevated blood pressure, or chest pain during exercise that are higher than an individual's normal history for these indicators can indicate emotional stress. The addition of story-telling or emotional experiences through computer games and/or simulations (and especially when such experiences are virtual-reality experiences) can help to elicit emotional and physiological responses or lack thereof. For example, a veteran suffering from PTSD (Post-Traumatic Stress Disorder) could be trained inside such a dual-tasking VR environment so that s/he can gradually regain her/his agency by overcoming progressively challenging physical and emotional scenarios—reactivating her/his dorsolateral prefrontal cortex and lateral nucleus of thalamus with the help of these combined physical and emotional activities (likely using parallel but not war-based scenarios). As a result, the veteran could potentially extricate herself or himself from such traumatic experiences by developing her/his closure stories.

The integration of a primary task with an associative activity is also especially well-suited for the evaluation and conditioning of specific aspects of neurological functioning in individuals training for physical, mental, or combined forms of competition. After an initial array of primary physical challenges and associated tasks designed to evaluate specific neurological functioning areas to create a profile of relative functioning a more thorough understanding of the competitor's strengths and weaknesses in their specific mode of competition can be achieved. With the help of a conditioning recommendation algorithm, expert input, and competitor input a regimen of primary and associative tasks specifically suited to improve performance of that competitor and mode of competition can be administered at prescribed or chosen frequency. Digital challenges can further be customized for competition and competitor specificity as the conditioning recommendation algorithm analyzes the efficacy of conditioning regimens for users aiming to improve in similar neurological functions, the specific user's response to conditioning inputs over time, and expert recommendations for users with similar neurological functioning profiles and objectives.

One form of treatment that may be used to treat neurological conditions is brainwave entrainment, which is readily integrated into many aspects of gaming. Depending on configuration, the system and method may comprise a display comprising virtual objects, a light-producing device (other than the display), an audio-producing device such as speakers or headphones, a haptic feedback device such as a vibratory motor, a means for monitoring the user's attention, and a software application which applies brainwave entrainment using some combination of the display, the light-producing device, the audio-producing device, and the haptic feedback device. In some embodiments, the brainwave entrainment may be based in part on the monitoring of the user's attention. In some embodiments, virtual objects on the display may be used to provide brainwave entrainment. Some embodiments may comprise additional components such as an entrainment routine selector which adjusts the brainwave entrainment based on certain inputs, biometric sensors such as an electroencephalograph which may be used to provide inputs to the software application or entrainment routine selector. In some embodiments, brainwave entrainment may be applied using combinations of brainwave entrainment from virtual objects on the display and physical stimulation transducers such as the light-producing device, the audio-producing device, and the haptic feedback device. In some embodiments, the software application is a virtual reality environment, and the display may be a virtual reality headset or other virtual reality display hardware.

Brainwave entrainment may be further enhanced by shared experiences such as online, multiplayer gameplay. A multi-person platform not only allows brainwave enhancement of multiple users simultaneously, the shared experience can enhance brainwave enhancement by participation in a common activity with like-minded persons. Some exemplary embodiments and descriptions herein describe use of the platform for gaming purposes. Some common types of multi-person virtual experiences that could be enhanced with brainwave entrainment using the platform include first person shooters, role-playing games, adventure games, real-time simulations, and collectible card games. However, the platform's usage is not limited to gaming. The platform can be configured to apply brainwave entrainment in any type of multi-person virtual experience, some examples of which include virtual group meditation sessions, virtual group kaleidoscope visualizations, simulations of real activities such as hiking and rock climbing, and simulations of non-real activities such as flying or using magic. Brainwave entrainment can either be similar or the same for all users, or can be applied differently to each user. Further, the virtual nature of the experiences can allow for shared overall experiences or engagement in a common activity while customizing the visual, auditory, and brainwave entrainment experience for each user.

Implementations of visual brainwave entrainment to date have been limited to passive visual stimulation using physical lights (typically light emitting diodes, or LEDs). There is no interactivity or active engagement with the visual stimulation transducers, which makes the process less effective and uninteresting. Further, the visual stimulation transducers, being physical objects, cannot be changed in terms of size or shape, cannot be modified in reaction to user feedback, and are limited in terms of colors available, are generally fixed in place, and additional lights cannot be added to the system without physically connecting (and likely programming) additional lights.

Virtual objects, on the other hand, have none of these limitations, and can be used as visual stimulation transducers while users are engaged with an on-screen display. Brainwave entrainment using virtual objects provides essentially unlimited variability in terms of stimulator sizes, shapes, colors, movements, rotations, etc., and allows for the use of multiple stimulators simultaneously, each with different characteristics. Any change to a virtual object that is perceptible to a user and can be applied at a repeating frequency may be used to apply brainwave entrainment.

Further, gamification changes the brainwave stimulation from passive receipt of light therapy to active engagement with the visual stimulation objects, wherein the user's brain is actively stimulated during the activity, enhancing the effectiveness of the stimulation. Further, as the user is actively engaged with the game, stimulation can be applied based on where the user's attention is focused. Attention-based stimulation provides opportunities for both direct stimulation (e.g., flashing an object at which the user is looking, playing sounds or providing haptic feedback associated with a game object or activity that is the object of the user's attention, etc.) and indirect stimulation (e.g., flashing an object in the user's periphery of vision, playing sounds or providing haptic feedback associated with the game, but not the object of the user's attention such as a background element, background music or sounds, etc.). For example, eye tracking technology can be used to determine where the user is looking on the screen at any given time, and objects at which the user is looking can be used to provide visual stimulation even if the user changes his or her attention to a different object on the screen. The user's attention to objects on the screen can be monitored over time to determine whether the user is remaining focused on the activity, or is getting tired and losing focus, and the determined level of user attention can be used to change the type, intensity, directness, and other characteristics of the stimulation. Other means of determining the user's attention may be used such as assuming that the user's attention is focused on an object with which the user has just interacted.

Brainwave entrainment using virtual objects may be further enhanced by using multiple objects, each capable of providing complementary types of stimulation, and/or by intentionally directing the user's attention to objects providing certain types of stimulation. For example, if the user is playing a first person shooter (FPS) game that involves shooting attacking aliens, the user's attention will naturally be focused on finding attacking aliens, aiming at them, and shooting them. As each alien will be the focus of the user's attention sequentially, the alien at which the user is currently looking may be flashed at appropriate frequencies and in appropriate colors to provide appropriate brainwave stimulation. Simultaneously, other objects on the screen (or even the background) may be selected to provide a complementary visual stimulation in the periphery of the user's vision. Further, brainwave entrainment using virtual objects may be enhanced by selecting multiple treatment modalities (e.g., light, sound, vibration, electrical stimulation) applied either simultaneously or sequentially, by varying the frequency or frequencies of brainwave entrainment (e.g., from about 0.5 Hz to about 100 Hz), and by varying the intensity and/or scale of the treatment (e.g., from subtle, localized vibrational or electrical stimulation to area-wide, intense stimulation such as high-intensity room lighting and sound).

Brainwaves are frequencies at which electrical impulses in the brain occur. Brainwave frequencies change based on the state of consciousness of the user (e.g., sleeping, awake, dreaming, concentrating, relaxed, contemplative, meditative, irritated, etc.). Generally speaking, brainwaves are divided into five categories with frequencies roughly in the following ranges.

Delta waves are brainwaves in the general frequency range of 0.1 Hz to 4 Hz. Delta waves occur during deep sleep, and indicate a low level of arousal. Theta waves are brainwaves in the general frequency range of 4 Hz to 8 Hz. Theta waves occur in a state between wakefulness and sleep, such as during daydreaming and meditation, and can indicate drowsiness, creativity, or imagination. Alpha waves are brainwaves in the general frequency range of 8 Hz to 12 Hz. Alpha waves occur during a waking state, but are associated with relaxation, problem solving, analysis, and decision-making. Beta waves are brainwaves in the general frequency range of 12 Hz to 30 Hz. Beta waves occur during alertness, concentration, and strenuous mental activities such as solving mathematical problems and planning for the future. Gamma waves are brainwaves in the general frequency range of 30 Hz to 44 Hz. Gamma waves are associated with high-level information processing. There is evidence of Lambda brainwaves in a range around 47 Hz to 70 Hz, and other brainwave entrainment frequencies may be useful up to around 100 Hz. These ranges are approximate, and there is some overlap between them.

There are many promising uses of brainwave entrainment. One promising use of brainwave entrainment is to treat and/or prevent epilepsy. There is some evidence that epileptic seizures occur when the brain falls into theta wave activity (approximately 4 Hz to 8 Hz) during normal waking consciousness. Normal waking consciousness is typically associated with beta wave brain activity (12 Hz to 38 Hz). Performing brainwave entrainment at beta wave frequencies on persons with epilepsy may help prevent them from falling into theta wave brain activity, thus preventing seizures.

Another possible use for brainwave entrainment is to reduce agitation by performing brainwave entrainment at alpha wave frequencies (approximately 8 Hz to 12 Hz). Alpha wave frequencies are those brain wave frequencies between theta wave activity (typically associated with dreaming) and beat wave activity (typically associated with concentration and learning). Alpha wave frequencies are associated with relaxation and calmness. Therefore, brainwave entrainment at alpha wave frequencies may help induce relaxation and calmness.

Many different wave forms and/or pulse widths may be used in delivering entrainment at the selected frequency or frequencies, regardless of the modality (light, sound, etc.) of the stimulation. Wave forms may include, but are not limited to, rectangular wave forms, sine wave forms, triangular wave forms, and sawtooth wave forms. Pulse widths or duty cycles at any given frequency may be varied across the entire range of the frequency period. For example, at a given frequency, the duty cycle of each period of the frequency can be varied from nearly 0% on-time/100% off-time to nearly 100% on-time/0% off-time. Thus, for a given frequency, the stimulator (e.g., light) can be on and off for an equal amount of time in each period (a 50% duty cycle), mostly on during each period (e.g., a 75% duty cycle), or mostly off during each period (e.g., a 25% duty cycle). In these cases, the frequency of the stimulation is the same, but the amount of on-time of the stimulation in each period of the frequency is different.

Different pulse widths or duty cycles may be useful, depending on the circumstances. For example, when engaged in a mental task that requires visual acuity, a very low or very high duty cycle may be used to flash a light stimulator at a pulse width that can be captured by the human eye, but is not consciously recognizable. The human eye can capture flashes of light as short as $1/200^{th}$ of a second (equivalent to a frequency of 200 Hz), possibly shorter, but because of persistence of vision, cannot distinguish between repeated flashes of light at that frequency. Television and computer monitor frame refresh rates are typically 60 Hz or above, as this is a frequency at which persistence of vision makes it difficult to distinguish between frames. Thus, for example, the flicker of light stimulation at a frequency of 40 Hz and a 50% duty cycle would be easily perceivable by most human beings as each "on" pulse is $1/80^{th}$ of a second long and separated by another "off" time of another $1/80^{th}$ of a second. However, the flicker of light stimulation at the same frequency, but at a 80% duty cycle would likely not be consciously perceptible, as the "on" time of each period would last about $1/50^{th}$ of a second and the "off" time of each period would last about $1/200^{th}$ of a second. Thus, the "off" time of each period is within the limits of capture by the human eye (200 Hz), but would likely not be consciously perceptible because it is above the average frequency resolution (60 Hz) of the human eye, and the light would appear to the conscious mind to be on all the time.

In a similar manner, pulse widths or duty cycles may be adjusted to be perceptible to certain cells in the eye but not others. The human eye has two different types of light receptors: cones and rods. Cones are the dominant light receptors used under daylight conditions, and reception of light by cones is called photopic vision. Cones are able to distinguish colors, but are less sensitive to lower light intensity and the persistence of vision of cones is greater (meaning that the frequency of pulses that can be distinguished by cones is less than for rods). Rods are the dominant light receptors used at night and under low-light conditions, and reception of light by rods is called scotopic vision. Rods are not able to distinguish colors, but are more sensitive to lower light intensity and the persistence of vision of rods is less (meaning that the frequency of pulses that can be distinguished by rods is greater than for cones). Cones are greatly concentrated in the center of vision (where the person is directly looking) while rods are considerably more dominant in the periphery of vision. This difference in the type of light receptors in the eye can be used to advantage when selecting either a frequency of stimulation or a pulse width/duty cycle of that frequency. Again using the example above where visual acuity is required for a mental task, the pulse width or duty cycle of each period of a brainwave entrainment frequency of light can be selected to be perceptible to rods but not to cones, thus allowing the brainwave entrainment frequency of light to be perceived by the brain (through the rods in the periphery of vision which have a greater frequency resolution), but not consciously perceptible to the person (who is primarily focused on the light received by the cones (in the center of vision and with a lesser frequency resolution).

One or more different inventions may be described in the present application. Further, for one or more of the inventions described herein, numerous alternative embodiments may be described; it should be appreciated that these are presented for illustrative purposes only and are not limiting of the inventions contained herein or the claims presented herein in any way. One or more of the inventions may be widely applicable to numerous embodiments, as may be readily apparent from the disclosure. In general, embodiments are described in sufficient detail to enable those skilled in the art to practice one or more of the inventions, and it should be appreciated that other embodiments may be utilized and that structural, logical, software, electrical and other changes may be made without departing from the scope of the particular inventions. Accordingly, one skilled in the art will recognize that one or more of the inventions may be practiced with various modifications and alterations. Particular features of one or more of the inventions described herein may be described with reference to one or more particular embodiments or figures that form a part of the present disclosure, and in which are shown, by way of illustration, specific embodiments of one or more of the inventions. It should be appreciated, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an embodiment with several components in communication with each other does not imply that all such components are required. To the contrary, a variety of optional components may be described to illustrate a wide variety of possible embodiments of one or more of the inventions and in order to more fully illustrate one or more aspects of the inventions. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the invention(s), and does not imply that the illustrated process is preferred. Also, steps are generally described once per embodiment, but this does not mean they must occur once, or that they may only occur once each time a process, method, or algorithm is carried out or executed. Some steps may be omitted in some embodiments or some occurrences, or some steps may be executed more than once in a given embodiment or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments of one or more of the inventions need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of embodiments of the present invention in which, for example, functions may be executed out of order from that shown or discussed, including substantially concurrently or in reverse order, depending on the functionality involved, as would be understood by those having ordinary skill in the art.

Definitions

The term "amplitude" means the difference between the high or low state of a signal or wave form and the base state of that signal or wave form in a full period (high/low or on/off cycle) of the frequency of the signal or wave form.

The phrase "associative activity" as used herein means a second task or activity to be engaged in by an individual under assessment. The associative activity will often, but not always, be a mental or cognitive task such as performing arithmetic or identifying objects on a display.

The term "biometrics" as used herein mean data that can be input, directly measured, or computed using directly measured data from a user. This data includes but is not limited to physical and virtual movement, physiological, biological, behavioral, navigational, cognitive, alertness and attention, emotional, and brainwave measurements and patterns.

The phrase "brainwave entrainment" means application of a stimulus with a frequency from about 0.5 Hz to about 100 Hz as a means of neurological therapy. The stimulus may be of any perceptible form such as, but not limited to, light, sound, vibration, or electrical stimulation. The stimulus need not be from the same source (e.g., two light sources each at 20 Hz could be synchronized to produce a 40 Hz stimulus) or from the same modality (e.g., a sound source at 15 Hz and a light source at 15 Hz could be synchronized to produce a 30 Hz stimulus).

The phrase "composite function score" as used herein means a indicative of a relative level of neurological functioning comprised of weighted input of combined movement, biometric, and performance data sources collected by a given embodiment of the system, input by the user or an expert, historical performance and life history data from various sources, etc.

The term "conditioning" as used herein means all aspects of the system that can be used for the improvement, training, treatment of or exposure to aspects of neurological functioning. This could be in the form of a prescribed regimen from an expert, recommendation algorithm, self-selected experiences, or combination thereof.

The term "display" means any type of device capable of producing an output visible to a user of the system. A non-limiting list of displays includes televisions, computer monitors, tablet and mobile phone screens, VR headsets, and projectors.

The phrase "dual task assessment" as used herein means measurement of baseline performance on a set of tasks and/or activities performed individually, as well as performance of the same set of tasks and/or activities simultaneously. While this is typically a single primary task (usually motor) combined with a single associative activity (typically a neurological activity such as cognitive task), it should be taken herein to include other combinations of multiplexed tasks in combinations including, but not limited to, combinations in excess of two tasks and combinations that target a single or multiple aspects of neurological functioning.

The phrase "dual task cost" as used herein means any method for quantifying the difference in performance of a dual task assessment between the set of tasks performed individually and the same set of tasks performed simultaneously. Typically includes a comparison of each task performed in isolation to the performance on each of those tasks when performed simultaneously, either for a pair or larger combination of tasks.

The phrase "duty cycle" means the amount of time that a frequency signal is in the "high" or "on" state, expressed as a percentage, wherein each full period (complete high/low cycle) of the frequency signal represents 100%. Note that "duty cycle" and "pulse width" are two different means of expressing the same concept.

The term "expert" as used herein means an individual with specialization in an area via formal training, credentials, or advanced proficiency in a modality of interest to the user or with regard to neurological functioning. This includes but is not limited to physicians, psychiatrists, physical therapists, coaches, fitness trainers, high level athletes or competitors, and teachers.

The term "frequency" means a signal or wave form having a periodic repetition of high/low or on/off states. Examples of signals and wave forms that exhibit the characteristic of frequency include, but are not limited to, rectangular wave forms, sine wave forms, triangular wave forms, and sawtooth wave forms.

The terms "game" or "game application" mean any computer game, puzzle, display, animation, or simulation comprising virtual objects that can be interacted with in some manner by a person. These phrases include, but are not limited to, traditional two-dimensional games and puzzles, three-dimensional virtual reality (VR) applications and environments, enhanced reality and augmented reality applications and environments (comprising both real-world elements and virtual elements, such as virtual objects superimposed on a video feed of the real environment surrounding the user), and interactive applications that allow one to sense virtual objects through haptic feedback (whether or not associated with a visual display of the objects).

The phrase "game environment data" means any and all data associated with storage, generation, display, tracking, and management of the game for purposes of game play by users. Non-limiting examples of game environment data include virtual game boards and game pieces for board games; virtual puzzle backgrounds and game pieces for puzzle games; three-dimensional game worlds for virtual reality games including landscapes, buildings, objects, non-player characters and other players; tracking and storage of changes to any of the above during game play.

The phrase "game play data" means any and all data associated with a user's interaction with a game such as, but not limited to, the location and movement of the user's cursor, pointer, avatar, or other representation in a game; the user's interaction with, or manipulation of, objects or environmental elements in a game; the inventory or items held by a user; game progress or story progress data; and statistics or scoring data such as game scores, hit rates and success rates, game progress indicators; and trophy or award accumulations.

The term "gamification" as used herein means the application of brainwave entrainment using a game or a game application.

The phrases "neurological functioning" and "neurological function" as used herein mean any and all aspects of neuroscience and neurology where input, output, processing, or combination thereof involve aspects of the nervous system. These include but are not limited to functional as well as anatomical aspects of cognitive, sensory, motor, emotional, and behavioral functions and experiences.

The phrase "primary task" as used herein means a first task or activity to be engaged in by an individual under assessment. The primary task will often, but not always, be a physical task or exercise such as walking on a treadmill.

The phrase "pulse width" means the amount of time that a frequency signal is in the "high" or "on" state, expressed as a time period that is a portion of each full period (complete high/low cycle) of the frequency signal. Note that "duty cycle" and "pulse width" are two different means of expressing the same concept. The phrase "pulse width modulation" is often used to denote changing of the pulse width of a frequency signal.

The term "transducer" as used herein means a device that converts an electrical signal into variations in a physical quantity, such as sound, light, pressure, or electrical stimulation. A display is included in the definition of "transducer."

The phrase "stimulation transducer" as used herein means a transducer used to stimulate one of the senses of a person or animal. Any portion of a display may be used as a stimulation transducer, non-limiting examples of which include virtual objects or backgrounds on the display.

The phrase "virtual object" means a computer-generated simulation of an object perceivable to a human being. Virtual objects include, but are not limited to, visible virtual objects such as two-dimensional and three-dimensional shapes shown on a display, non-visible virtual objects such as those that might be "felt" through haptic feedback (e.g., gloves equipped with haptic feedback equipment that provide resistance to the user's fingers around the contours of a virtual object in space), and any combination of the two (e.g., a visible virtual object displayed in a virtual reality environment through a VR headset which can also be "felt" by the user via haptic feedback). A virtual object does not have to be gamified and may be, for example, a virtual object displayed on a screen.

The phrase "virtual reality" means a computer-generated environment in which a person may participate as an actor in the environment via an avatar representing the person in the computer-generated environment. The phrase "virtual reality" includes all forms of such environments including where the entire environment is computer-generated and where the computer generated environment includes real-world elements, often referred to as "extended reality," or "augmented reality." The phrase "virtual reality" does not require the use of a virtual reality headset.

Conceptual Architecture

Figure 1:
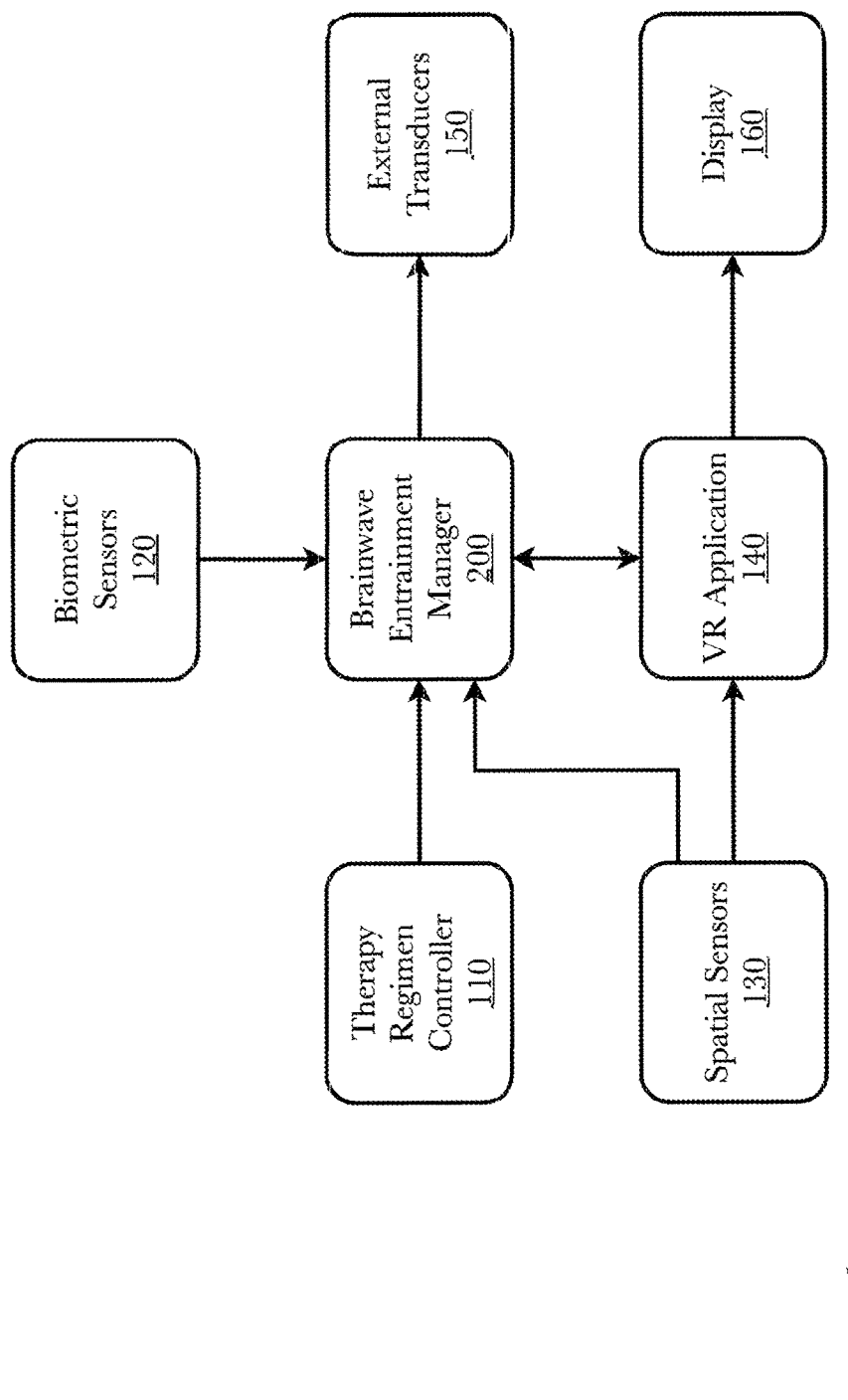
FIG. 1 is a diagram showing an exemplary overall system architecture for a brainwave entrainment system using virtual objects and environments as visual, stimulation transducers.

FIG. 1 is a diagram showing an exemplary overall system architecture 100 for a brainwave entrainment system using virtual objects and environments as visual stimulation transducers. In this embodiment, the system comprises a brainwave entrainment manager 200, a virtual reality (VR) application 140, a therapy regimen controller 110, one or more spatial sensors 130, one or more biometric sensors 120, and one or more external transducers, and a display 160.

The brainwave entrainment manager 200 is the core of the system, and manages inputs from, and outputs to, other components of the system. It is responsible for selection of entrainment routines, evaluation of the user's attention, and activation of both virtual and physical stimulation transducers.

The therapy regimen controller 110 is an administrative interface that allows an administrator (e.g., a physician, therapist, masseuse, or other service provider) to select therapy regimens for application to the user (who may be a patient, client, etc., of the administrator). The therapy regimen controller 110 may be used, for example, to select a regimen for brainwave entrainment that emphasizes alpha wave stimulation to induce relaxation in an overstimulated user.

The biometric sensors 120 are sensors that measure a physical or physiological characteristic of the user, such as heart rate, temperature, sweat production, brain activity (using an electroencephalograph, or EEG), etc. Biometric sensors 120 are used to provide feedback to the brainwave entrainment manager 200 as to the physical or physiological state of the user, which may be used to infer the user's mental state. For example, a biometric sensor 120 that measures the user's heart rate may be used to infer the user's level of relaxation (or lack thereof), thus providing feedback as to the effectiveness of alpha brainwave entrainment intended to induce relaxation.

Spatial sensors 130 are sensors that measure a user's physical location in space or a location at which the user is focusing his or her attention. For two dimensional screens, eye movement may be tracked and the location of the user's gaze may be calculated. In the case of virtual reality (VR), the user's body may be tracked, or if the user is wearing a VR headset, the orientation of the headset can be used to detect the user's head movements. Spatial sensors 130 are used to detect the user's engagement with virtual objects and virtual environments, such that brainwave entrainment using those objects and environments can be adjusted, accordingly.

The VR application 140 is used for gamification of brainwave entrainment. While a VR application 140 is shown here, in principle any computer game, puzzle, display, or animation can be used, whether interactive or not, and whether three-dimensional or two-dimensional. The VR application 140 can be a specially-designed program intended for use with the system, or can be an off-the-shelf game or application adapted for use with the system. In either case, the VR application 140 will either have an interface with the brainwave entrainment manager 200, or will have a brainwave entrainment manager 200 integrated into it, whereby the brainwave entrainment manager 200 is used to control brainwave entrainment using the virtual objects in the VR application 140.

The external transducers 150 are physical stimulation transducers that may be used to complement brainwave entrainment using virtual objects. A non-limiting list of external transducers 150 includes lights or LEDs, speakers or other audio-producing devices, vibratory or other pressure-producing devices, and electrical stimulators. As an example, while brainwave entrainment is being applied visually using virtual objects on a screen, the brainwave entrainment may be supplemented or complemented by audible brainwave entrainment using speakers.

The display 160 may be any type of display producing an output visible to a user of the system. A non-limiting list of displays 160 includes computer and tablet screens, VR headsets, and projectors. The display 160 is the means by which visual brainwave entrainment may be applied using virtual objects.

Figure 2:
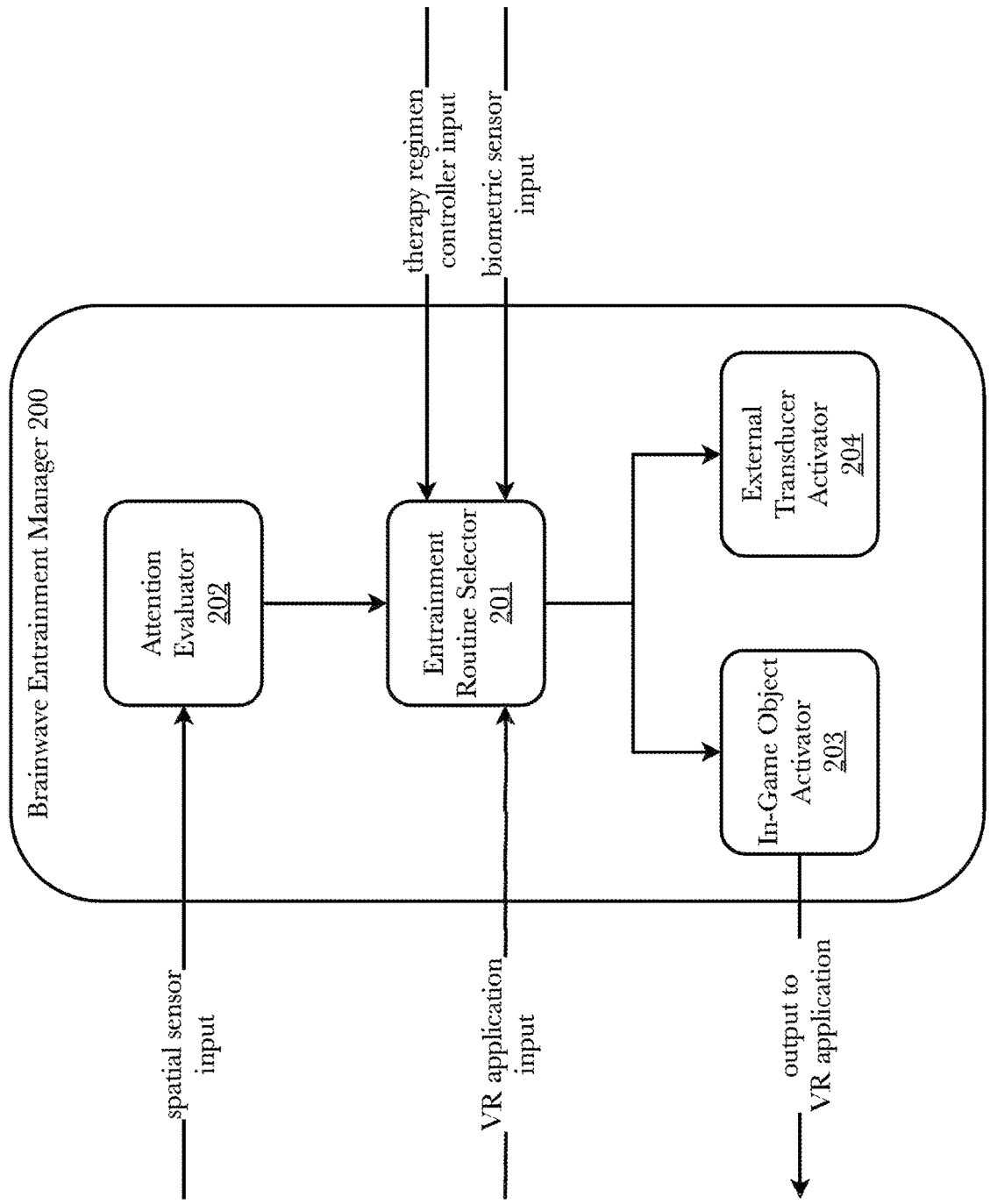
FIG. 2 is a diagram showing an exemplary architecture for the brainwave entrainment manager aspect of the brainwave entrainment using virtual objects and environments as visual, stimulation transducers.

FIG. 2 is a diagram showing an exemplary architecture for the brainwave entrainment manager aspect of the brainwave entrainment using virtual objects and environments as visual stimulation transducers. In this embodiment, the brainwave entrainment manager 200 comprises an entrainment routine selector 201, an attention evaluator 202, an in-game object activator 203, and an external transducer activator 204. The entrainment routine selector 201 receives input VR application input, therapy regimen controller input, and biometric sensor input, and input from the attention evaluator 202. Based on those inputs, the entrainment routine selector chooses and/or modifies a brainwave routine appropriate for the circumstances. For example, if the therapy regimen controller input specifies that the overall brainwave entrainment goal is relaxation, the entrainment routine selector 201 may select alpha wave entrainment as the primary entrainment therapy, and may choose to apply alpha wave entrainment to a background virtual object, as flashing of background objects will be less intrusive (and possibly more relaxing) to the user than flashing of objects to which the user's attention is directed. To determine which objects are not the subject of the user's attention, the attention evaluator 202 receives input from a spatial sensor (e.g., a camera used to track eye movements) to determine where the user is looking on the screen at a given moment. The entrainment routine selector 201 then modifies the entrainment routine to flash an object or objects at which the user is not looking using an in-game object activator 203 which interfaces with the VR application to identify which objects should be flashed.

The user's attention need not be tracked via a camera, and may be tracked through other means. For example, the user's attention may be tracked by monitoring the user's interaction with the virtual objects or virtual environment in the form of mouse clicks, keyboard activity, orientation of the user's head or body (e.g., when a virtual reality headset is being used), orientation and/or movement of hand-held trackable devices such as game controllers with integrated accelerometers, gyroscopes, etc. In some embodiments, the user's attention may be tracked not in terms of visual direction or attention, but in the more general sense of focus, consistency, ability to concentrate, level of interest, response times, or other factors not necessarily associated with the direction of the user's vision. All of these things may be incorporated into decisions by the entrainment routine selector 201 as to changes to be made to the entrainment routine.

Simultaneously, the entrainment routine selector 201 may activate one or more external transducers 204 using an external transducer activator 204, where the entrainment routine selector 201 determines that external transducers may supplement or complement the brainwave entrainment using virtual objects. The entrainment routine selector 201 may further use feedback to determine whether the selected entrainment routine is having the desired effect. As an example, the entrainment routine selector 201 may use biometric feedback such as a user's heart rate (e.g., a lowering heart rate may be used to infer relaxation) to change the entrainment routine. For example, a lowering heart rate during alpha wave entrainment would likely indicate relaxation, in which case the entrainment routine would remain unmodified, but a rising heart rate would likely indicate irritation, in which case the entrainment routine might be modified by reducing the entrainment to theta wave entrainment to further induce relaxation.

Many other types and implementations of feedback are possible including, but not limited to, changing of entrainment routines based on user reactions to, or interactions with, virtual objects and virtual environments; user attention attributes such as the location, intensity, focus, and consistency of user attention to virtual objects and virtual environments; game scores and other gaming metrics; physical biofeedback such as monitoring heart rate, perspiration, respiration; cognitive biofeedback such as monitoring changes in an EEG; exercise equipment feedback such as treadmill speed, cycling cadence and/or power, rowing strokes per minute and/or power. Further, entrainment routines can be changed to use different types of stimulation (e.g., if the feedback indicates that visual stimulation is less effective at certain points in a game, it can be supplemented with auditory or haptic feedback). Multiple stimulation devices can be used to augment or supplement the visual stimulation including, but not limited to, haptic headbands or vest, speakers or headphones, and other stimulation devices. In this way, the system can be programmed to automatically adapt to users based on a variety of feedback sources.

FIG. 13 is a block diagram showing an exemplary system architecture for a multi-person brainwave entrainment platform. The exemplary architecture shown in this diagram is a client-server architecture shown in the context of a computer gaming platform, although the architecture shown can be applied to any multi-person virtual experience. The multi-person brainwave entrainment platform of this embodiment comprises a cloud-based gaming platform 1300 which may be accessed by any number of game clients 1330 each operating on a particular computing device and through which the user of the computing device accesses the virtual experience (in this example, a multi-player computer game).

Cloud-based gaming platform 1300 comprises frontend services 1310 and backend services 1320. Frontend services 1310 are accessible via a network connection (e.g., via the Internet) by game clients 1330, and comprise game platform services 1311 and game servers 1312. Game platform services 1311 provide services outside of game play such as leaderboards, group formation, lobbies, chat rooms, inventory management, and account management. Game servers 1312 are the hardware (real or virtual) on which the games are run. Game servers 1312 may be real or virtual, and dedicated or not, and distributed or not. The exemplary architecture of this diagram shows dedicated, non-distributed game servers (which may still be either real machines or virtual machines). Each game server 1312 of this embodiment further comprises a brainwave entrainment manager 1313 with functionality similar to brainwave entrainment manager 200 of earlier-described embodiments. In this embodiment, however, brainwave entrainment manager 1313 manages brainwave entrainment routines for a plurality of users engaging in a shared virtual experience. Backend services 1320 interface only with frontend services 1310 and are not directly accessible by game clients 1330. Backend services 1320 provide the storage and administrative functionality for the game and comprise an analytics stack 1321 and a game database 1322. Analytics stack 1321 allows for queries about game operations and statistics by gameplay programmers and designers, business managers, and customer service representatives. Game database 1322 stores all information about the game necessary for its operation including, but not limited to, locations, maps, activities of player characters and non-player characters, game states, and game events.

Game clients 1330 are software applications or web browsers operating on end-user computing devices which access cloud-based gaming platform 1300 to send and retrieve game-related data. Game clients 1300 may operate on any end-user device, three examples of which are smartphones 1331, personal computers (PCs) 1332, and gaming consoles or handheld devices 1333. Game clients 1330 access cloud-based gaming platform 1300 via a network connection (e.g., via the Internet or a local area network) exchange game-related data with frontend 1310 of cloud-based gaming platform 1300 and display the user's perspective of the game to the user of the device on which the game client is operating. Thus, each user sees a different perspective of the game from each other user. As will be further described below, in certain configurations this allows for a shared virtual experience or common activity along with a different gameplay feel or intensity and/or different brainwave entrainments for each user.

FIG. 14 is a block diagram showing an alternative exemplary system architecture for a multi-person brainwave entrainment platform. In this alternate architecture, the dedicated game servers have been removed from cloud-based computing platform and replaced with a peer-to-peer architecture wherein an end-user computing device on which one of the game clients 1430 is operating acts as the game server for one or more other game clients 1430. Again, while the exemplary architecture shown in this diagram is shown in the context of a computer gaming platform, the architecture shown can be applied to any multi-person virtual experience. The multi-person brainwave entrainment platform of this embodiment comprises a cloud-based gaming platform 1400 which may be accessed by any number of game clients 1430 each operating on a particular computing device and through which the user of the computing device accesses the virtual experience (in this example, a multi-player computer game).

Cloud-based gaming platform 1400 comprises frontend services 1410 and backend services 1420. Frontend services 1410 are accessible via a network connection (e.g., via the Internet) by game clients 1430, and comprise game platform services 1411. Game platform services 1411 provide services outside of game play such as leaderboards, group formation, lobbies, chat rooms, inventory management, and account management. Backend services 1420 interface only with frontend services 1410 and are not directly accessible by game clients 1430. Backend services 1420 provide the storage and administrative functionality for the game and comprise an analytics stack 1421 and a game database 1422. Analytics stack 1421 allows for queries about game operations and statistics by gameplay programmers and designers, business managers, and customer service representatives. Game database 1422 stores all information about the game necessary for its operation including, but not limited to, locations, maps, activities of player characters and non-player characters, game states, and game events.

Game clients 1430 are software applications or web browsers operating on end-user computing devices which access cloud-based gaming platform 1400 to send and retrieve game-related data. Game clients 1400 may operate on any end-user device, three examples of which are smartphones 1431, personal computers (PCs) 1432, and gaming consoles or handheld devices 1433. Game clients 1430 access cloud-based gaming platform 1400 via a network connection (e.g., via the Internet or a local area network) exchange game-related data with frontend 1410 of cloud-based gaming platform 1400 and display the user's perspective of the game to the user of the device on which the game client is operating. Thus, each user sees a different perspective of the game from each other user. As will be further described below, in certain configurations this allows for a shared virtual experience or common activity along with a different gameplay feel or intensity and/or different brainwave entrainments for each user.

In this embodiment, an end-user device acts as the game server 1433 for one or more other game clients 1430. Game servers are the hardware (real or virtual) on which the games are run, in this case the physical hardware of the end-user device or a virtual machine operating on the end-user device. In this peer-to-peer gaming architecture, each game client 1431, 1433, 1435 further comprises its own on-device brainwave entrainment manager 1432, 1434, 1436 each with functionality similar to brainwave entrainment manager 200 of earlier-described embodiments. In this embodiment, however, each brainwave entrainment manager manages brainwave entrainment routines for the user of the device on which its associated game client is operating. Here, client B/game server 1433 accesses cloud-based gaming platform 1300 via a network connection (e.g., via the Internet or a local area network), exchanges game-related data with frontend 1410 of cloud-based gaming platform 1400, displays the user's perspective of the game to the user of client B/game server 1433, and shares the exchanged game-related data with other game clients 1431, 1435 for them to do the same for their users. Thus, each user sees a different perspective of the game from each other user, notwithstanding the fact that client B/game server 1433 is the only game server in connection with cloud-based gaming platform 1400. As will be further described below, in certain configurations this allows for a shared virtual experience or common activity along with a different gameplay feel or intensity and/or different brainwave entrainments for each user.

FIG. 17 is a block diagram showing an exemplary architecture for a cloud-based gaming platform with integrated healthcare diagnostics and treatment. The exemplary architecture shown in this diagram is a client-server architecture shown in the context of a computer gaming platform, although the architecture shown can be applied to any multi-person virtual experience. Cloud-based gaming platform with integrated healthcare diagnostics and treatment 1700 comprises frontend services 1710, backend services 1720, and a healthcare diagnostics and treatment module 1800. The cloud-based gaming platform with integrated healthcare diagnostics and treatment 1700 of this embodiment may be accessed by any number of game clients 1730 each operating on a particular computing device and through which the user of the computing device accesses the virtual experience (in this example, a multi-player computer game).

Frontend services 1710 are accessible via a network connection (e.g., via the Internet) by game clients 1730, and comprise game platform services 1711 and game servers 1712. Game platform services 1711 provide services outside of game play such as leaderboards, group formation, lobbies, chat rooms, inventory management, and account management. Game servers 1712 are the hardware (real or virtual) on which the games are run. Game servers 1712 may be real or virtual, and dedicated or not, and distributed or not. The exemplary architecture of this diagram shows dedicated, non-distributed game servers (which may still be either real machines or virtual machines). Each game server 1712 of this embodiment further comprises a brainwave entrainment manager 1717 with functionality similar to brainwave entrainment manager 200 of earlier-described embodiments. In this embodiment, however, brainwave entrainment manager 1717 manages brainwave entrainment routines for a plurality of users engaging in a shared virtual experience. In addition to receiving game data, frontend 1710 may be configured to receive confidential health-related data via a Health Information Patient Protection Act (HIPPA) compliant health data tunnel such as a virtual private network (VPN), which health-related data may be passed to healthcare diagnostics and treatment module 1800 via a HIPPA-compliant security gateway 1810. In an alternate configuration, healthcare diagnostics and treatment module 1800 receives health-related data direct from game clients 1730 through a HIPPA-compliant health data tunnel such as a VPN via HIPPA-compliant security gateway 1810. In either configuration, the health-related data is secured against receipt by third parties.

Backend services 1720 interface only with frontend services 1710 and are not directly accessible by game clients 1730. Backend services 1720 provide the storage and administrative functionality for the game and comprise an analytics stack 1721 and a game database 1722. Analytics stack 1721 allows for queries about game operations and statistics by gameplay programmers and designers, business managers, and customer service representatives. Game database 1722 stores all information about the game necessary for its operation including, but not limited to, locations, maps, activities of player characters and non-player characters, game states, and game events.

Game clients 1730 are software applications or web browsers operating on end-user computing devices which access cloud-based gaming platform 1700 to send and retrieve game-related data. Game clients 1700 may operate on any end-user device, three examples of which are smartphones 1731, personal computers (PCs) 1732, and gaming consoles or handheld devices 1733. Game clients 1730 access cloud-based gaming platform 1700 via a network connection (e.g., via the Internet or a local area network) exchange game-related data with frontend 1710 of cloud-based gaming platform 1700 and display the user's perspective of the game to the user of the device on which the game client is operating. Thus, each user sees a different perspective of the game from each other user. As will be further described below, in certain configurations this allows for a shared virtual experience or common activity along with a different gameplay feel or intensity and/or different brainwave entrainments for each user.

Healthcare diagnostics and treatment module 1800 comprises a HIPPA-compliant security gateway 1810, an artificial intelligence (AI) assisted healthcare diagnostics module 1820, and an alerts and treatments module 1830. In this embodiment, healthcare diagnostics and treatment module 1800 is shown as being located on a common platform. However, being a cloud-based system, a variety of network configurations may be used. The components of frontend 1710, backend 1720, and healthcare diagnostics and treatment module 1800 may be hosted on the same server, across a network of servers, or across a network of cloud-based services and microservices (Amazon Web Services (AWS)™ being one example of such a cloud-based service).

Healthcare diagnostics and treatment module 1800 receives a variety of health-related data such as dual-task data (data regarding physical and mental performance of a user while engaged in combinations of physical and mental activity), social game data (such as audio recordings or chat logs between players during gameplay), and certain types of game play data (including, for example, reaction times to events in the game). As will be described below, healthcare diagnostics and treatment module 1800 processes the received data through a variety of analyzers to make diagnostic predictions about the physical and mental health of the user. One or more trained machine learning algorithms may be used to identify patterns and correlations across disparate types of data to make predictions and diagnoses about the physical and mental health of the user.

FIG. 18 is a block diagram showing an exemplary architecture for an AI-assisted healthcare diagnostics module aspect of a cloud-based gaming platform with integrated healthcare diagnostics and treatment. AI-assisted healthcare diagnostics module 1820 of this embodiment comprises a patient database 1821, a physical function analysis module 1822, a neurological function analysis module 1823, a reaction time analysis module 1824, a mental health analysis module 1825, and one or more machine learning algorithms 1826.

AI-assisted healthcare diagnostics module 1820 receives and transmits data via a HIPPA-compliant security gateway 1810 which is configured to secure protected health information to, from, and within healthcare diagnostics and treatment module 1800 to prevent unauthorized access to protected health information of persons using the system. HIPPA-compliant security gateway 1810 uses information technology (IT) security best practices which include, but are not limited to, data encryption, access restrictions, permission controls, user authentications, and audit controls. HIPPA-compliant security gateway 1810 may use a HIPPA-compliant data health data tunnel 1702 which secures transmitted data end-to-end from game clients 1730 to healthcare diagnostics and treatment module 1800. HIPPA-compliant data health data tunnel 1702 may, as one example, use a virtual private network (VPN) established between game clients 1730 and healthcare diagnostics and treatment module 1800, which may, depending on configuration, run through frontend 1710. HIPPA-compliant data health data tunnel 1702 may be a separate connection from the connections between game clients 1730 and frontend 1710 through which game data 1710 is transmitted, in which case game data 1710 may not need to be encrypted. In some embodiments, HIPPA-compliant data health data tunnel 1702 and game data 1701 may be the same connection, but with HIPPA-compliant data health data encrypted or otherwise secured within the connection. For simplicity, HIPPA-compliant data health data tunnel 1702 and game data 1701 connections are shown as being singular connections, but in practice those connections will be made separately to each individual game client.

Patient database 1821 stores all incoming and outgoing patient data including, but not limited to, health-related data, game data, and healthcare diagnoses. Healthcare related data may include patient data such as medical records, medical evaluations, diagnoses, physical and mental evaluations, and dual-task data comprising physical and mental data acquired during dual-task testing. Game data may include patient data acquired during game play or related to game play such as types of games played, game scores, time spent playing, in-game performance data such as reaction times to certain events, trends in gameplay such as improvements or degradation over time, and social game data such as audio recordings or chat logs between players during gameplay. Diagnoses may include any sort of evaluation and recommendation regarding physical function or mental function including both high and low functionality or ability such as evaluations of cognition, speech, auditory processing, vision processing, motor skills, emotions, and memory. Diagnoses may include, but are not limited to, diagnoses of medical conditions, suspicions or indications of disease, suspicions or indications of chronic physical conditions, suspicions or indications of chronic mental or neurological conditions, and recommendations for treatment, rehabilitation, or therapy of any of the above.

Physical function analysis module 1822 receives and analyzes data associated with a physical task of a dual-task functional analysis. This will typically be the primary task of a dual-task functional analysis. Physical function analysis module 1822 may be configured to evaluate a variety of aspects of a patient's physical function including, but not limited to, range of motion, movement profiles, and gait analysis, each of which is described in more detail herein below. Analyses produced by physical function analysis module 1822 are output to machine learning algorithm 1826 as data for inclusion in determination of diagnoses by machine learning algorithm 1826. Physical function analysis module 1822 and neurological function analysis module 1823 may coordinate with one another to act as a dual-task functional analysis system as further described herein below.

Neurological function analysis module 1823 receives and analyzes data associated with mental task of a dual-task functional analysis. This will typically be the associative activity task of a dual-task functional analysis. Neurological function analysis module 1823 may be configured to evaluate a variety of aspects of a patient's mental or neurological function including both high and low functionality or ability such as evaluations of cognition, speech, auditory processing, vision processing, motor skills, emotions, and memory, each of which is described in more detail herein below. Analyses produced by physical function analysis module 1822 are output to machine learning algorithm 1826 as data for inclusion in determination of diagnoses by machine learning algorithm 1826. Physical function analysis module 1822 and neurological function analysis module 1823 may coordinate with one another to act as a dual-task functional analysis system as further described herein below.

In-game performance analysis module 1824 receives and analyzes data associated with game play including, but not limited to, in-game performance data. In-game performance data may be separate from associative activity task data received by neurological function analysis module 1823, although there may be some overlap, depending on the game or software in operation. As a general rule, in-game performance data will be ancillary game play data such as shots per kill (in first person shooter games), number of tiles removed (in tile-based games like Mahjong), track records and lap times (in racing games), time spent playing each game, and similar data. This data may be tracked over time to identify deviances from expectation that may indicate some physical or cognitive change. For example, if a player plays a certain game on a daily basis, the player's in-game performance data would be expected to improve over time. A decrease in performance despite continued play, especially a sudden or dramatic decrease, may suggest a physical or neurological deficiency. Analyses produced by in-game performance analysis module 1824 are output to machine learning algorithm 1826 as data for inclusion in determination of diagnoses by machine learning algorithm 1826.

Mental health analysis module 1825 receives and analyzes game-related social data such as chat sessions, audio from team or group gameplay, lobby interactions, game-joining or partnering preferences and trends, game-related group activities, and membership in game-related clubs, factions, or guilds. Game-related social data may be separate from associative activity task data received by neurological function analysis module 1823, although there may be some overlap, depending on the game or software in operation. This data may be analyzed to identify potential mental health issues such as depression, anxiety, anger, sadness, frustration, and the like. One method of analysis that may be used by mental health analysis module 1825 to identify potential mental health issues is use of a trained machine learning algorithm to recognize patterns of social interaction similar to those that have led to such issues in a larger group comprising the training data for the machine learning algorithm. For example, a trend in the player's social data toward the use of words and phrases like "tired," "exhausted," "lack of energy," in chats and audio with friends and teammates, combined with a withdrawal from or reduced activity in group activities, may suggest that the player is suffering from depression. A machine learning algorithm trained on a large database of similar social data and associated mental health issues would be able to recognize complex patterns in the social data suggestive of various mental health issues. Analyses produced by mental health analysis module 1825 are output to machine learning algorithm 1826 as data for inclusion in determination of diagnoses by machine learning algorithm 1826.

Machine learning algorithm 1826 is one or more machine learning algorithms configured to identify patterns in data.

Machine learning algorithm 1826 is configured to make health-related diagnoses by identifying patterns in complex data. Machine learning algorithm 1825 may receive either data input to the various modules 1822-1825, or the outputs of the various modules 1822-1825, or a combination of the two. Based on this complex data set comprising many factors associated with a person's physical function and mental function as described above for the various modules 1822-1825, machine learning algorithm 1826 makes one or more diagnoses regarding one or more aspects of the person's physical or mental function. Diagnoses may include any sort of evaluation and recommendation regarding physical function or mental function including both high and low functionality or ability such as evaluations of cognition, speech, auditory processing, vision processing, motor skills, emotions, and memory. Diagnoses may include, but are not limited to, diagnoses of medical conditions, suspicions or indications of disease, suspicions or indications of chronic physical conditions, suspicions or indications of chronic mental or neurological conditions, and recommendations for treatment, rehabilitation, or therapy of any of the above. Diagnoses may be combined into a composite functioning score spatial map showing ability in a plurality of functional areas, as further described below.

Machine learning algorithms excel at finding patterns in complex data or exploring the outcomes of large numbers of potential options. There are three primary categories of machine learning algorithms, supervised machine learning algorithms, unsupervised machine learning algorithms, and reinforcement machine learning algorithms. Supervised machine learning algorithms are trained to recognize patterns by training them with labeled training data. For example, a supervised machine learning algorithm may be fed pictures of oranges with the label "orange" and pictures of basketballs with the label basketball. The supervised machine learning algorithm will identify similarities (e.g., orange color, round shape, bumpy surface texture) and differences (e.g., black lines on basketball, regular dot pattern texture on basketball versus random texture on oranges) among the pictures to teach itself how to properly classify unlabeled pictures input after training. An unsupervised machine learning algorithm learns from the data itself by association, clustering, or dimensionality reduction, rather than having been pre-trained to discriminate between labeled input data. Unsupervised machine learning algorithms are ideal for identifying previously-unknown patterns within data. Reinforcement machine learning algorithms learn from repeated iterations of outcomes based on probabilities with successful outcomes being rewarded. Reinforcement machine learning algorithms are ideal for exploring large number of possible outcomes such as possible outcomes from different moves on a chess board. Within each primary category of machine learning algorithms, there are many different types or implementations of such algorithms (e.g., a non-exhaustive list of unsupervised machine learning algorithms includes k-means clustering algorithms, hierarchical clustering algorithms, anomaly detection algorithms, principle component analysis algorithms, and neural networks. The category and type of machine learning algorithm chosen will depend on many factors such as the type of problem to be solved (e.g., classification of objects versus exploration of possible outcomes), the need for insight into how the machine learning algorithm is making its decisions (most machine learning algorithms operate as black boxes wherein their decision-making is opaque to users), accuracy required of predictions, availability of labeled training data sets, and knowledge or lack of knowledge regarding patterns or expected patterns within the data.

FIG. 19 is a block diagram showing an exemplary architecture for an alerts and treatments module aspect of a cloud-based gaming platform with integrated healthcare diagnostics and treatment. Alerts and treatments module 1830 of this embodiment comprises a patient database 1821, a brainwave entrainment manager 1831, an alert generator 1832, a physical activity routine generator 1833, a mental activity routine generator 1834, and a treatment control signal generator 1835.

Alerts and treatments module 1830 receives and transmits data via a HIPPA-compliant security gateway 1810 which is configured to secure protected health information to, from, and within healthcare diagnostics and treatment module 1800 to prevent unauthorized access to protected health information of persons using the system. HIPPA-compliant security gateway 1810 uses information technology (IT) security best practices which include, but are not limited to, data encryption, access restrictions, permission controls, user authentications, and audit controls. HIPPA-compliant security gateway 1810 may use a HIPPA-compliant data health data tunnel 1702 which secures transmitted data end-to-end from game clients 1730 to healthcare diagnostics and treatment module 1800. HIPPA-compliant data health data tunnel 1702 may, as one example, use a virtual private network (VPN) established between game clients 1730 and healthcare diagnostics and treatment module 1800, which may, depending on configuration, run through frontend 1710. HIPPA-compliant data health data tunnel 1702 may be a separate connection from the connections between game clients 1730 and frontend 1710 through which game data 1710 is transmitted, in which case game data 1710 may not need to be encrypted. In some embodiments, HIPPA-compliant data health data tunnel 1702 and game data 1701 may be the same connection, but with HIPPA-compliant data health data encrypted or otherwise secured within the connection. For simplicity, HIPPA-compliant data health data tunnel 1702 and game data 1701 connections are shown as being singular connections, but in practice those connections will be made separately to each individual game client.

Patient database 1821 stores all incoming and outgoing patient data including, but not limited to, health-related data, game data, and healthcare diagnoses. Healthcare related data may include patient data such as medical records, medical evaluations, diagnoses, physical and mental evaluations, and dual-task data comprising physical and mental data acquired during dual-task testing. Game data may include patient data acquired during game play or related to game play such as types of games played, game scores, time spent playing, in-game performance data such as reaction times to certain events, trends in gameplay such as improvements or degradation over time, and social game data such as audio recordings or chat logs between players during gameplay. Diagnoses may include any sort of evaluation and recommendation regarding physical function or mental function including both high and low functionality or ability such as evaluations of cognition, speech, auditory processing, vision processing, motor skills, emotions, and memory. Diagnoses may include, but are not limited to, diagnoses of medical conditions, suspicions or indications of disease, suspicions or indications of chronic physical conditions, suspicions or indications of chronic mental or neurological conditions, and recommendations for treatment, rehabilitation, or therapy of any of the above.

Brainwave entrainment manager 1831 functions in a manner similar to brainwave entrainment manager of other embodiments previously described (e.g., brainwave entrainment manager 200, brainwave entrainment manager 1313). Upon receipt of one or more diagnoses for a person, brainwave entrainment manager 1831 selects an appropriate brainwave entrainment routine, and passes the selection on to a treatment control signal generator 1835, which generates the appropriate game instructions or controls to implement the brainwave entrainment routine selected within a current or future game.

Alert generator 1832 generates alerts for a player based on lists or databases of diagnoses and information relevant thereto. Upon receipt of one or more diagnoses for a person, alert generator retrieves relevant information about the diagnoses from one or more lists or databases, identifies issues of concern associated with each diagnosis, and generates alerts based on rule sets. The issues of concern may be things such as health warnings, side effect warnings, medication interaction warnings, physical exertion warnings, and the like. The issue of concern may include thresholds for action or generation of alerts such as warnings not to exceed a certain heartrate or time of exercise.

While not show in this diagram, alert generator 1832 may further generate alerts based on data such as that described above is being received by the various modules 1822-1825 of AI-assisted healthcare diagnostics module 1820 (dual-task data, in-game performance data, game-related social data). For example, alert generator 1832 may receive real-time data regarding a person's posture and balance and generate immediate in-game or on-screen warnings of an imminent fall. Such real-time warnings of falls are particularly useful in certain circumstances such as use of exercise machines my elderly persons who may be prone to falls or by persons wearing virtual reality (VR) headgear who are unable to visually perceive the real-world environment in which they are gaming.

Alerts may be in-game alerts such as pop-up windows or text on the screen or flashing of the screen or elements on the screen in a particular color or pattern (e.g., three flashes of the full screen in red to indicate serious alerts or in yellow to indicate moderate alerts). Alerts may be outside-of-game alerts such as via text or email, warning or advising of concerns identified while gaming. Outside-of-game alerts are appropriate where immediate action does not need to be taken, but the person should be advised of some information or concern.

Physical activity routine generator 1833 receives diagnoses and selects appropriate physical exercise routines for the person diagnosed to perform based on known or suspected associations between physical exercise and the diagnosis. For example, walking is considered to be an effective form of physical rehabilitation for patients with various chronic conditions such as low back pain, strokes, and peripheral artery disease. Walking can be prescribed at various speeds and lengths of time and can be adjusted based on feedback either from the patient or from analyses from a dual-task functional analysis system comprising an exercise device and sensors for providing feedback from physical activity. Likewise, cardiovascular exercise such as running and cycling can be an effective form of medical treatment for chronic diseases such as obesity, high blood pressure, heart disease, and diabetes. It can be used preventatively to reduce the risk of other diseases such as thrombosis. Studies have also shown that cardiovascular exercise may be an effective treatment for neurological diseases such as Alzheimer's disease, age-related memory loss, and age-related dementia. Strength training such as weight lifting resistance-based exercise machines can prevent and treat muscle loss and bone density loss, particularly in elderly patients. Using databases of medical knowledge comprising known and suspected uses of physical activity to prevent and/or treat diseases and medical conditions, physical activity routine generator 1833 generates a physical activity routine appropriate to the received diagnosis, and passes the selection on to a treatment control signal generator 1835, which generates the appropriate game instructions or controls to implement the brainwave entrainment routine selected within a current or future game. In some embodiments, physical activity routine generator 1833 may be the primary task generator for a dual-task functional analysis system.

Mental activity routine generator 1834 receives diagnoses and selects appropriate mental activity routines for the person diagnosed to perform based on known or suspected associations between mental exercise and the diagnosis. Brain-training games such as memory games, reasoning games, math-related games, puzzles, concept-association games, knowledge games, and the like, have been shown to be an effective form of mental rehabilitation and treatment for patients with neurological conditions such as age-related dementia and rehabilitation from brain injuries incurred from accidents and strokes. Different types of brain games encourage thinking and engage different portions of the brain, so different brain games can be prescribed as part of a mental activity routine for targeting treatment of different types of brain injuries, different brain locations, or different types of brain deficiencies. Using databases of medical knowledge comprising known and suspected uses of brain games to prevent and/or treat diseases and medical conditions, mental activity routine generator 1834 generates a mental activity routine appropriate to the received diagnosis, and passes the selection on to a treatment control signal generator 1835, which generates the appropriate game instructions or controls to implement the brainwave entrainment routine selected within a current or future game. In some embodiments, mental activity routine generator 1834 may be the associative activity task generator for a dual-task functional analysis system.

Detailed Description of Exemplary Aspects

Figure 3:
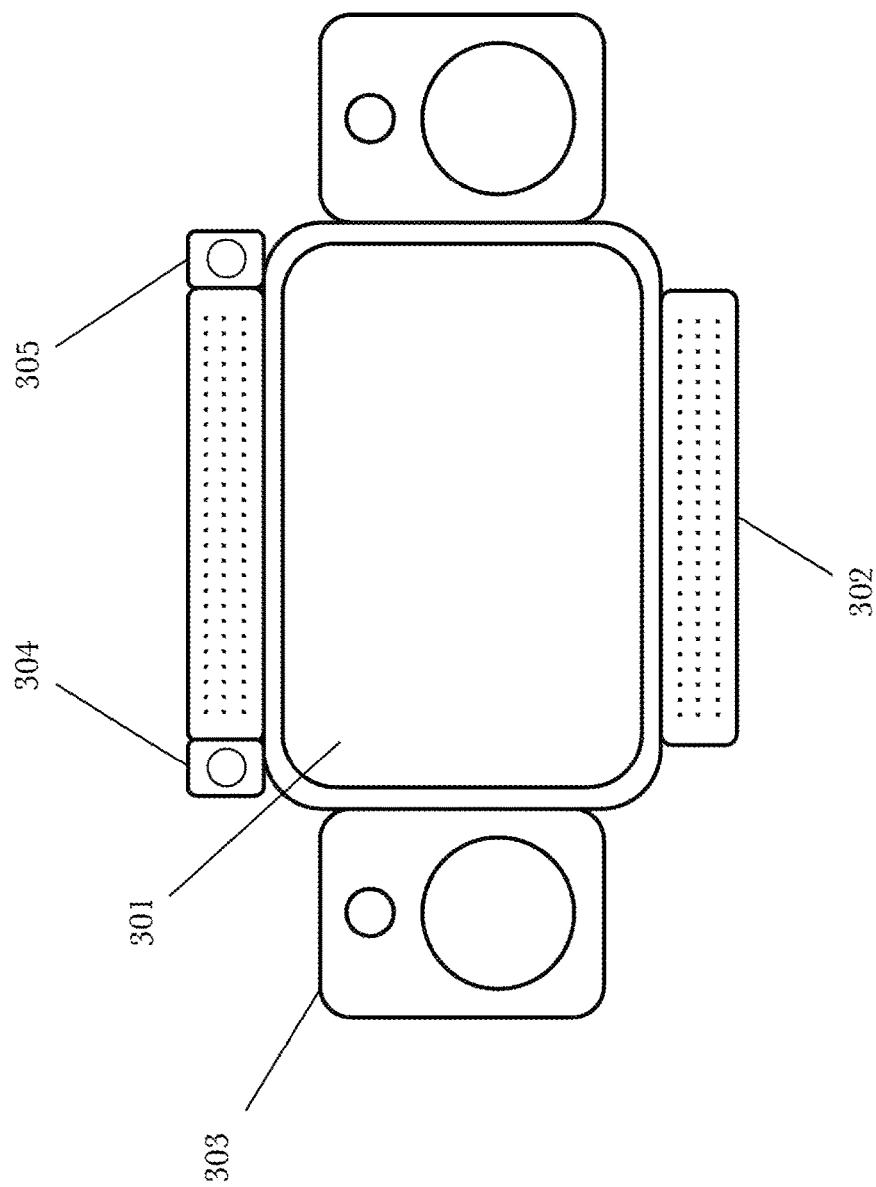
FIG. 3 is a diagram of an exemplary brainwave entrainment therapy device that can be attached to an exercise machine for targeted brainwave entrainment therapy with attention tracking and virtual objects.

FIG. 3 is a diagram of an exemplary brainwave entrainment therapy device that can be attached to an exercise machine for brainwave entrainment therapy with light and/or sound, including brainwave entrainment using virtual objects. In this embodiment, the brainwave entrainment device comprises a display 301, one or more lights 302, and one or more speakers or headphones 303. The display 301 is used for display of activities designed to engage the user in games or other activities while brainwave entrainment is applied using virtual objects on the display. The lights 302, shown here as light bars comprising multiple light-emitting diodes (LEDs) can be programmed to emit a supplemental visible stimulus (e.g., flashes, on/off cycles, etc.) at frequencies appropriate for brainwave entrainment. The speakers 303 can be programmed to emit a supplemental audible stimulus (e.g., rectangular wave sound pulses, sine wave sound oscillations, etc.) at frequencies appropriate for brainwave entrainment. In some configurations, both light and sound may be used as stimuli, separately or in conjunction with brainwave entrainment using virtual objects on the display 301. The stimuli need not be from the same source (e.g., two light sources each at 20 Hz could be synchronized to produce a 40 Hz stimulus) or from the same modality (e.g., a sound source at 15 Hz and a light source at 15 Hz could be synchronized to produce a 30 Hz stimulus)

The device of this embodiment is designed such that is can be mounted on an exercise machine (that may or may not be otherwise equipped for brainwave entrainment purposes), whereby it can be used to provide brainwave entrainment using virtual objects on the display 301, optionally with supplemental brainwave entrainment from the lights 302 and/or speakers 303. The use of virtual objects with brainwave entrainment allows for flexibility in applying brainwave entrainment. Brainwave entrainment using virtual objects provides essentially unlimited variability in terms of stimulator sizes, shapes, colors, movements, and allows for the use of multiple stimulators simultaneously, each with different characteristics. Further, gamification changes the brainwave stimulation from passive receipt of light therapy to active engagement with the visual stimulation objects, wherein the user's brain is actively stimulated during the activity, enhancing the effectiveness of the stimulation. Further, as the user is actively engaged with the virtual objects, stimulation can be applied based on where the user's attention is focused. Attention-based stimulation provides opportunities for both direct stimulation (e.g., flashing an object at which the user is looking) and indirect stimulation (e.g., flashing an object in the user's periphery of vision). For example, eye tracking technology can be used to determine where the user is looking on the screen at any given time, and objects at which the user is looking can be used to provide visual stimulation even if the user changes his or her attention to a different object on the screen. In this embodiment, an infrared emitter 304 emits an infrared light, which is reflected off the user's eye and cornea, and is received at an infrared-sensitive camera 305. The center of the eye is tracked in relation to a reflection from the cornea (the outer surface of the eye). The distance and direction of the difference between the center of the eye and the corneal reflection can be used to calculate the eye's position. Combined with a known distance to and size of the display 301 the location at which the user is looking can be determined. The user's attention to objects on the screen can be monitored over time to determine whether the user is remaining focused on the activity, or is getting tired and losing focus, and the determined level of user attention can be used to change the type, intensity, directness, and other characteristics of the stimulation.

Brainwave entrainment using virtual objects may be further enhanced by using multiple objects, each capable of providing complementary types of stimulation, and/or by intentionally directing the user's attention to objects providing certain types of stimulation. For example, if the user is playing a first person shooter (FPS) game that involves shooting attacking aliens, the user's attention will naturally be focused on finding attacking aliens, aiming at them, and shooting them. As each alien will be the focus of the user's attention sequentially, the alien at which the user is currently looking may be flashed at appropriate frequencies and in appropriate colors to provide appropriate brainwave stimulation. Simultaneously, other objects on the screen (or even the background) may be selected to provide a complementary visual stimulation in the periphery of the user's vision. Further, brainwave entrainment using virtual objects may be enhanced by selecting multiple treatment modalities (e.g., light, sound, vibration, electrical stimulation) applied either simultaneously or sequentially, by varying the frequency or frequencies of brainwave entrainment (e.g., from about 0.5 Hz to about 100 Hz), and by varying the intensity and/or scale of the treatment (e.g., from subtle, localized vibrational or electrical stimulation to area-wide, intense stimulation such as high-intensity room lighting and sound).

Application of brainwave entrainment using virtual objects and gamification allows for brainwave entrainment to target certain neurological functions by enhancing and concentrating the effect of the brainwave entrainment on the stimulated areas of the brain. As one example, a person with memory loss may be asked to play a memory-based card matching or tile matching game (mental activities which stimulate certain portions of the brain). While the person is engaged in the mental activity, brainwave entrainment is applied via the game objects on the display 301 and/or the lights 302 and/or speakers 303. As the neurological functions in the brain associated with memory are being stimulated, the neurons in the brain associated with those functions are in an already-stimulated state, and the brainwave entrainment's stimulation of oscillations in the electrochemical state of neurons in those already-stimulated areas will have a more pronounced effect than on other areas of the brain. In this way, the already-stimulated areas of the brain may experience a greater reduction in degenerative conditions (i.e., reductions in amyloid plaques and tau phosphorylation) and greater increases in synaptic density.

Figure 4:
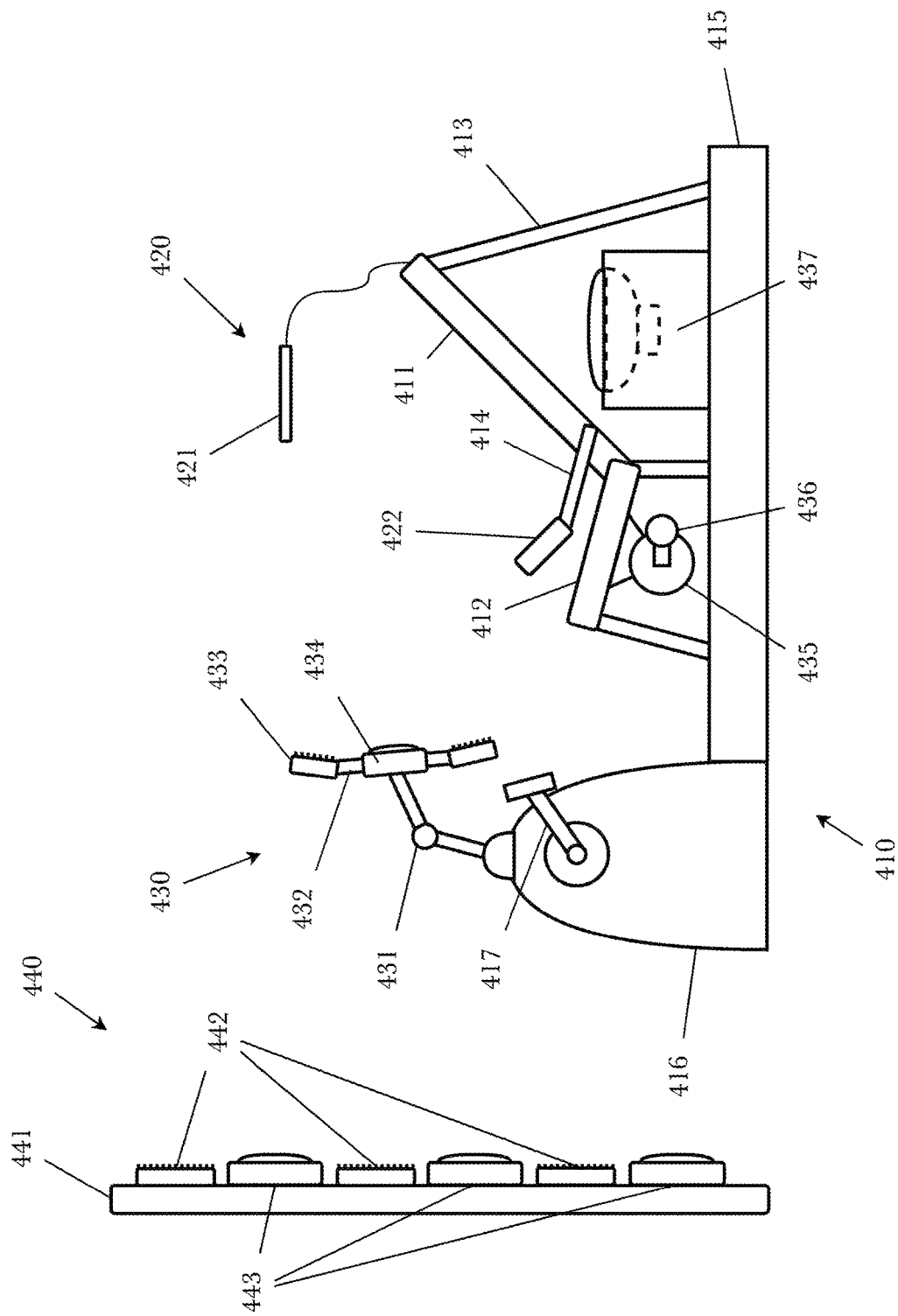
FIG. 4 is a diagram of an exemplary brainwave entrainment therapy system for brainwave entrainment therapy with attention tracking and virtual objects plus external stimulation transducers that allows for multi-modal, multi-intensity treatment.

FIG. 4 is a diagram of an exemplary brainwave entrainment therapy system for brainwave entrainment therapy that allows for multi-modal, multi-intensity therapies. The system 400 of this embodiment comprises a stationary recumbent bicycle 410, and three different scales of brainwave entrainment stimulators: localized and/or individual stimulation transducers 420, small area stimulation transducers 430, and large area stimulation transducers 440.

The stationary recumbent bicycle 410 comprises a base 415, a chair back 411, a seat 412, arm rests 414, a plurality of supports 413 connecting the chair back 411 and seat 412 to the base 415, a resistance mechanism 416 allowing for resistance to a pedaling motion of the user, and a pedal system 417 for the user to pedal in a cycling motion. The stationary recumbent bicycle 410 thus provides the means for the user to engage in a physical task in the case where dual task stimulation (and/or dual task assessment) is being applied.

The localized and/or individual stimulation transducers 420 of this embodiment are a headband 421 with vibratory stimulation and hand grips 422 which provide electrical stimulation. These provide localized stimulation which can only be perceived by the user, which also makes them individual stimulation transducers (as opposed to the other scales, which can be perceived by others, and which could be used to provide brainwave entrainment to more than one person using the same transducer(s)). The headband 421 may produce simple vibratory (i.e., tactile) stimulation to the head, or may be configured to produce vibrations at certain locations on the head and at certain intensities so as to be perceptible by the middle and inner ear, which causes the stimulation to be both tactile and auditory in nature. This double stimulation (tactile and auditory) amplifies the effect of a single type of transducer, increasing the efficiency of brainwave entrainment from applications of that transducer.

The small area stimulation transducers 430 of this embodiment are devices attached to the exercise machine 410, but not directly attached to or in contact with the user. For example, a console comprising a display 432, light bars 433, and speakers 434 similar to that of the device of FIG. 33 may be used. The console may be attached to the exercise machine using an adjustable arm 431 that allows for optimal positioning of the console for viewing and/or interaction by the user. Other small area stimulation transducers include a large electric motor 435 with an offset weight 436 attached to the seat 412 that allows for full-body vibratory stimulation to be applied, and a subwoofer 437 under the chair back 411 that allows for both audible (regular sound) and inaudible (infrasound) stimulation to be applied. Small area stimulation transducers are particularly useful in situations where direct contact with a user is not desirable, or when multiple users will be using the device sequentially, or when brainwave entrainment will be applied to a small number of users (e.g., those directly in front of the stimulation transducers). The display 432 may be used to provide brainwave entrainment using virtual objects in conjunction with gamification.

The large area stimulation transducers 440 of this embodiment are devices that can be used over a large area and potentially a large number of persons such as a room or auditorium. In this embodiment, The large area stimulation transducers are large LED light bars 442 and large speakers 443 attached to a wall 441 of the room in which the stimulation will be applied. The large area stimulators such as the LED light bars 442 and large speakers 443 on the wall 441 can be used to fully immerse the user in intense brainwave entrainment with large areas of bright light and loud, booming sounds. The immersion and intensity can be enhanced, for example, by surrounding the user with large area stimulators on walls on all sides (and possibly ceilings and floors) covering the user's entire visual area, so that the user receives visual stimulation no matter in which direction the user looks an auditory stimulation no matter where the user is located. Higher immersion and intensity may provide greater beneficial effects from brainwave entrainment.

It is important to note that any type of transducer can be applied at any scale. For example, light stimulation can be configured such that it is seen only by one person (e.g., in glasses or goggles), or is seen by a small number of persons (e.g., a single LED light bar), or is seen by many people (e.g. room lights, stadium lights, etc.). Further, the intensity of stimulation can be largely varied separately from the scale of stimulation. However, depending on the circumstances and application, brainwave entrainment at certain scales and/or intensities may be more useful or effective than at others.

The different scales of stimulation transducers allow for a choice of the level of immersion the user experiences with respect to the brainwave entrainment, and to some degree, the level of intensity of the brainwave entrainment. Immersion is the quality of being surrounded by or absorbed in an experience. Intensity is the magnitude of the experience. They are separate qualities (e.g., a localized electric stimulation can be intense, but not immersive), but there can be an increase in intensity with an increase in scale (for example, if light stimulation comes from all directions, it will tend to be both more immersive and more intense, although the intensity of the lights can be reduced to offset this tendency). For example, a localized, subtle electrical stimulation through electrically-conducting hand grips 422 provides minimal immersion of the user in the brainwave entrainment. This may be useful, for example, where intense concentration on the dual task stimulation is necessary. Small area stimulation transducers such as the LED light bars 433 on the screen console are useful for mid-level immersion and mid-level intensity of brainwave entrainment. The LED light bars 433 cover a small, but significant, area of the user's view, and the speakers 44 are large enough to provide a substantial auditory stimulus. The large area stimulators such as the LED light bars 442 and large speakers 443 on the wall 441 can be used to fully immerse the user in intense brainwave entrainment with large areas of bright light and loud, booming sounds. The immersion and intensity can be enhanced, for example, by surrounding the user with large area stimulators on walls on all sides (and possibly ceilings and floors) covering the user's entire visual area, so that the user receives visual stimulation no matter in which direction the user looks an auditory stimulation no matter where the user is located. Higher immersion and intensity may provide greater beneficial effects from brainwave entrainment.

Further, it is important to note that the modalities (types of stimulation), scales, and intensities allows for tremendous flexibility in selecting suitable therapies regimens for different situations. For high-immersion scenarios (e.g., maximum brainwave entrainment with fewer cognitive demands such as listening to music), multiple modalities, scales, and intensities may be used at the same time. For example, while a user is listening to classical music, localized electrical stimulation may be applied to the wrist, small area visual stimulation may be applied using a single LED light bar, and large area tactile stimulation may be applied using subwoofers which produce sounds (infrasounds) which are inaudible to the human ear but can be perceived through the sense of touch (e.g., as oscillating pressure on the torso).

Further, modalities can be chosen to either amplify certain tasks or activities or to supplement them. For amplification, treatment modalities are chosen to include those corresponding to a given task or activity in gamification. As an example, if a user is assigned a game activity wherein the user must follow a moving object on the display with his or her eyes, the object can be flashed at 40 Hz for gamma entrainment therapy. As the user is already focused on the object, the user is focusing more intensely on visual activities (and the brain areas and functions associated with visual activities are stimulated), enhancing the effect of the visual gamma entrainment modality. For supplementation, treatment modalities are chosen to exclude those corresponding to a gamification task. As an example, if game activity assigned to a user is identifying songbirds presented on the display, flashing the birds at 40 Hz (or otherwise changing their colors or visual appearance) may interfere with the identification process. In such circumstances, a non-conflicting modality may be chosen such as flashing of background objects or supplementation with audible entrainment.

Figure 5A:
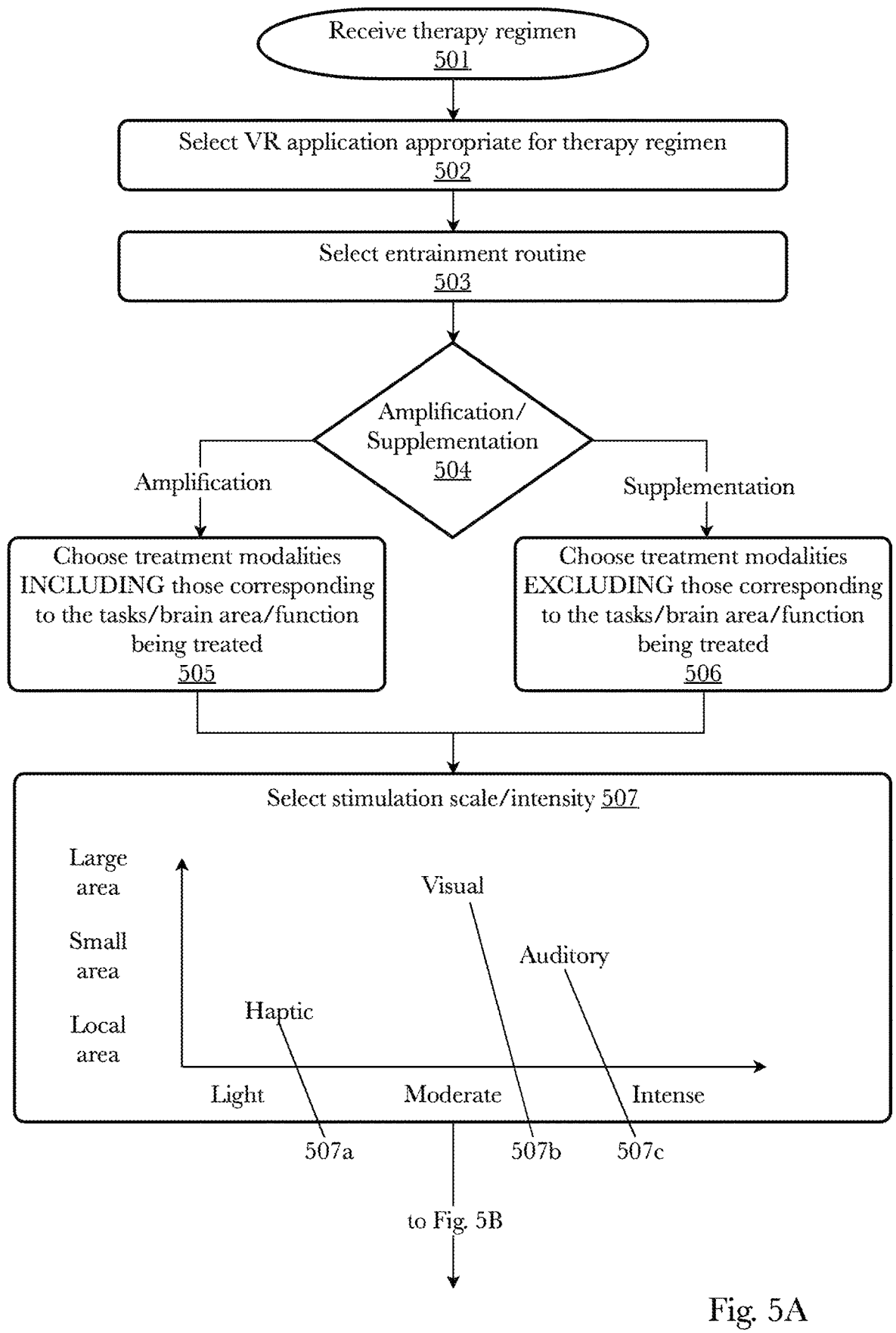
FIGS. 5A & 5B are a flow diagrams showing an algorithm for selection of modalities and routines for brainwave entrainment and application of brainwave entrainment using a virtual environment using eye tracking and biometric feedback to select virtual objects and entrainment routines.
Figure 5B:
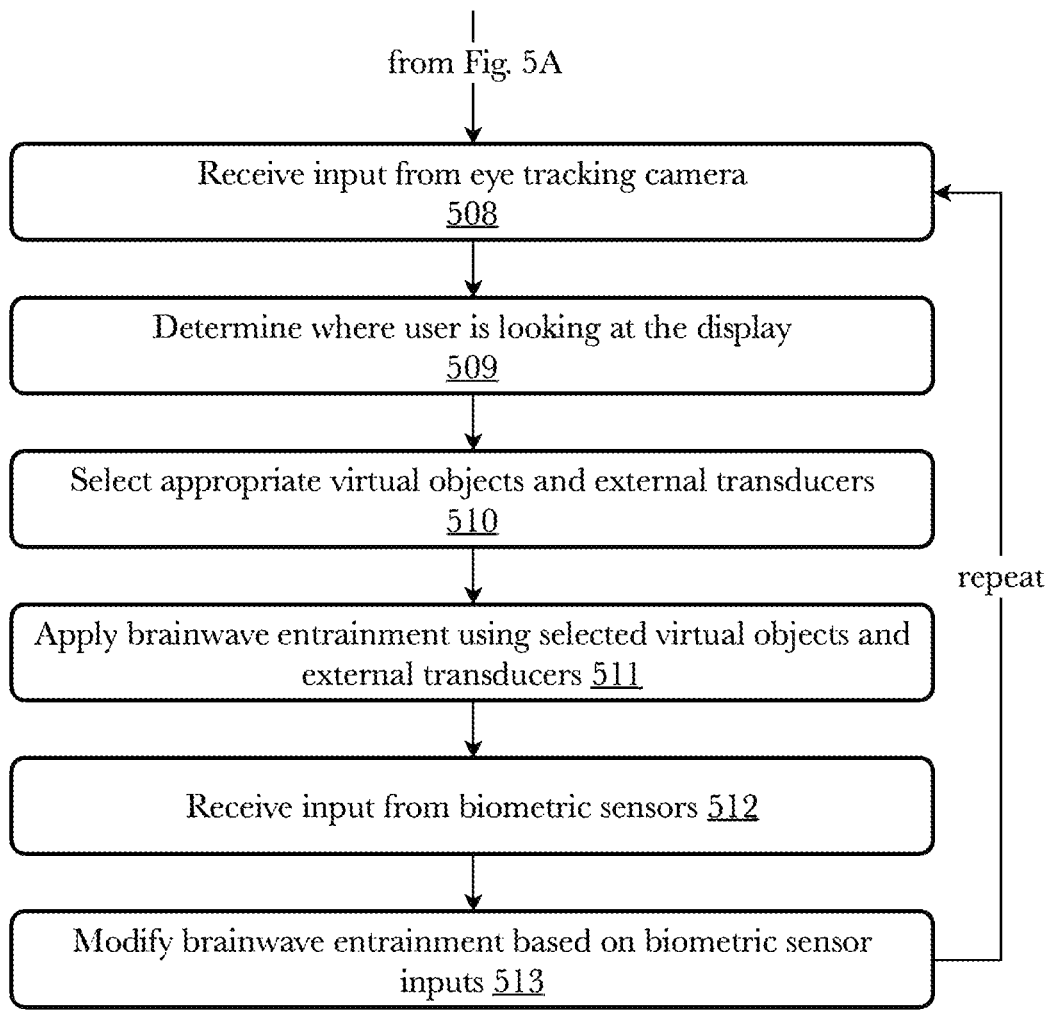

FIGS. 5A & 5B are a flow diagram showing an algorithm for selection of modalities and routines for brainwave entrainment and application of brainwave entrainment using a virtual environment using eye tracking and biometric feedback to select virtual objects and entrainment routines. As a first step, a therapy regimen is received 501 The therapy regimen may be received from any source providing instructions for brainwave entrainment, such as a database, an administrator (e.g., a physician, therapist, masseuse, or other service provider) for application to a user (who may be a patient, client, etc., of the administrator), or from the user himself or herself. An example therapy regimen would be a regimen for brainwave entrainment that emphasizes alpha wave stimulation to induce relaxation in an overstimulated user.

A suitable VR application or other gamification application is then chosen 502, which ideally should be consistent in content with the nature of the therapy regimen chosen. For example, if the therapy regimen is a regimen for brainwave entrainment that emphasizes alpha wave stimulation to induce relaxation in an overstimulated user, a VR application might be chosen that involves causal cycling along a forest path. If a more stimulating therapy regimen is chosen, for example something involving intense concentration and gamma wave therapy, a first person shooter might be chosen.

Based on the therapy regimen and VR application chosen, an entrainment routine is selected 503. For example, if the therapy regimen specifies that the overall brainwave entrainment goal is relaxation, the entrainment routine selected 503 may use alpha wave entrainment as the primary entrainment therapy, and may choose to apply alpha wave entrainment to a background virtual object (e.g., the sky or trees in the background of the casual cycling along the forest path), as flashing of background objects will be less intrusive (and possibly more relaxing) to the user than flashing of objects to which the user's attention is directed (e.g., the path or direction of the virtual bicycle). Selection of the entrainment routine 503 may further involve selecting amplification or supplementation 504 as appropriate for the circumstances, choosing appropriate treatment modalities (e.g., light therapy, sound therapy, vibrational therapy, electrical therapy, or combinations of such modalities) either for amplification 505 (treatments including those corresponding to the tasks, activities, or neurological function) or for supplementation 506 (treatments including those corresponding to the tasks, activities, or neurological function), and selecting a stimulation scale and intensity 507 for each modality appropriate for the treatment goals. In this example, three modalities are shown with different scales and intensities, localized haptic stimulation at a light intensity 507a, large area visual stimulation at a moderate intensity 507b, and small area auditory stimulation at a moderately intense intensity 507c. Brainwave entrainment is then applied using the chosen regimen, providing targeted treatment of particular areas of the brain and/or particular neurological functions via stimulation of those areas or functions using dual task stimulation.

At this point, a camera may be used to track the user's eye movements 508 to determine where the user is looking on the screen at a given moment 509. Based on the above inputs, appropriate virtual objects are chosen to apply brainwave entrainment by modifying virtual objects on the screen 510, which modification may take any number of forms (e.g., objects may be flashed at specific frequencies, the color of objects may be changed at specific frequencies, the size of objects may be changed at specific frequencies, objects may be rotated at specific frequencies, etc.). Any change to a virtual object that is perceptible to a user and can be applied at a repeating frequency (i.e., oscillating frequency) may be used to apply brainwave entrainment. Brainwave entrainment is applied using the virtual objects, optionally supplemented with entrainment from external transducers 511.

Input from biometric feedback (e.g., the user's heart rate) is received 512 and evaluated to determine whether the selected entrainment routine is having the desired effect (e.g., a lowering heart rate may be used to infer relaxation), and to change the entrainment routine, accordingly 513. For example, a lowering heart rate during alpha wave entrainment would likely indicate relaxation, in which case the entrainment routine would remain unmodified, but a rising heart rate would likely indicate irritation, in which case the entrainment routine might be modified by reducing the entrainment to theta wave entrainment to further induce relaxation. The process of tracking the user's attention and applying appropriate modifications to brainwave entrainment is repeated from step 508 until the therapy session ends.

Figure 6:
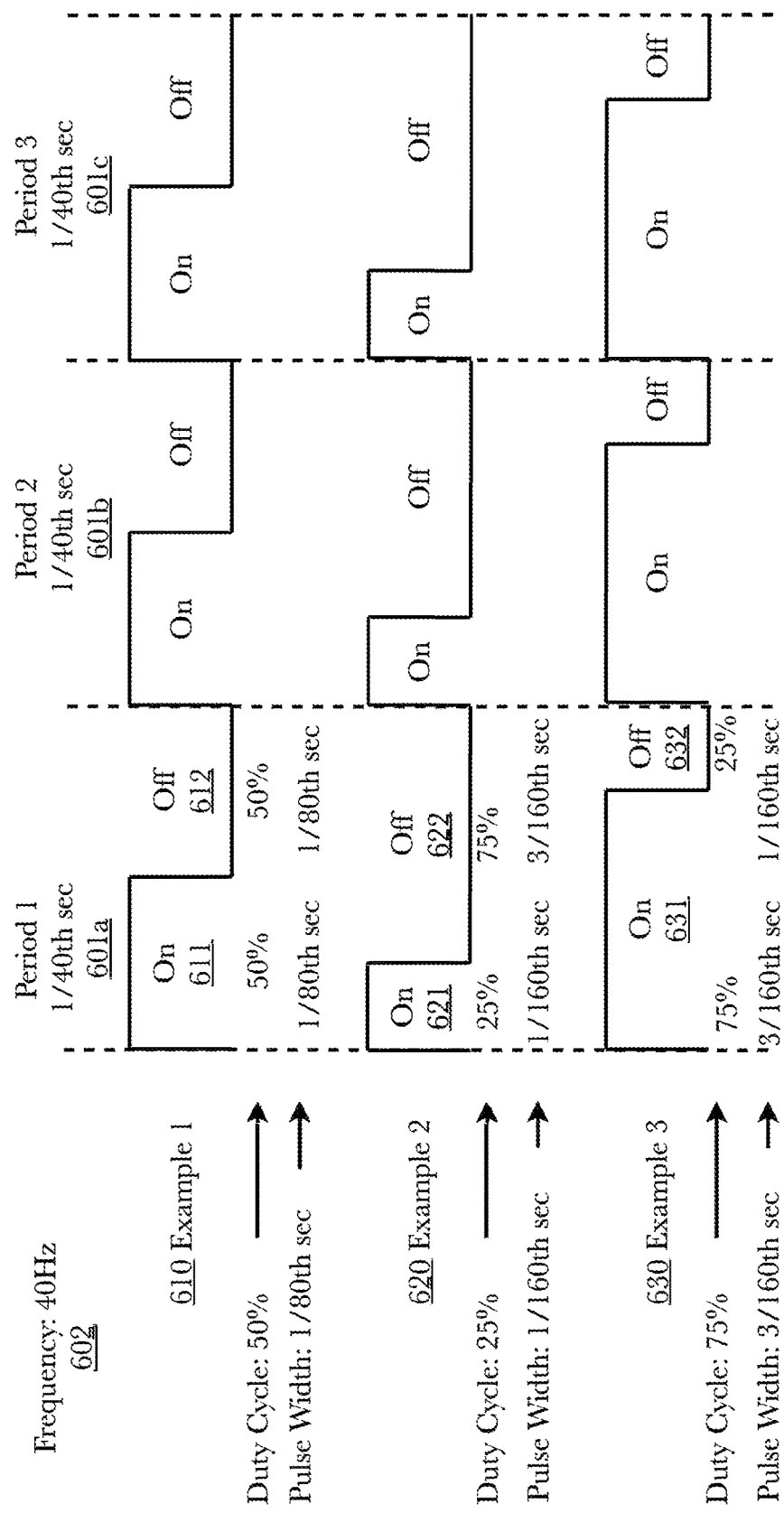
FIG. 6 is a diagram explaining the use of duty cycles and pulse width modulations in applying brainwave entrainment.

FIG. 6 is a diagram showing explaining the use of duty cycles and pulse width modulations in applying brainwave entrainment. Here, three examples 610, 620, and 630 of duty cycles/pulse width modulation are shown. The frequency of stimulation 602 in all three examples is 40 Hz (40 cycles per second), and the wave form of each example is a rectangular wave (i.e., instantaneous or near-instantaneous changes between on and off states). Three periods 601a-c of the stimulation at the 40 Hz frequency 602 are shown, each period corresponding to one full on/off cycle lasting $\frac{1}{40}^{th}$ of one second. In Example 1 610, a duty cycle of 50% is shown in which the stimulation is in an on state 611 for 50% of the period and in an off state 612 for 50% of the period. For a 40 Hz frequency as shown here, this corresponds to a pulse width of $\frac{1}{80}^{th}$ of a second, wherein the stimulation is in an on state 611 for $\frac{1}{80}^{th}$ of a second and in an off state 612 for $\frac{1}{80}^{th}$ of a second. In Example 2 620, a duty cycle of 25% is shown in which the stimulation is in an on state 621 for 25% of the period and in an off state 622 for 75% of the period. For a 40 Hz frequency as shown here, this corresponds to a pulse width of $\frac{1}{160}^{th}$ of a second, wherein the stimulation is in an on state 621 for $\frac{1}{160}^{th}$ of a second and in an off state 622 for $\frac{3}{160}^{th}$ of a second. In Example 3 630, a duty cycle of 75% is shown in which the stimulation is in an on state 631 for 75% of the period and in an off state 632 for 25% of the period. For a 40 Hz frequency as shown here, this corresponds to a pulse width of $\frac{3}{160}^{th}$ of a second, wherein the stimulation is in an on state 631 for $\frac{3}{160}^{th}$ of a second and in an off state 632 for $\frac{1}{160}^{th}$ of a second.

FIGS. 7-9 (PRIOR ART) explain the application of eye tracking technology as a means of determining where a user is looking. In one form of eye tracking technology, an infrared emitter 720 emits an infrared light 721, which is reflected off the user's eye 701 and cornea, and is received 731 at an infrared-sensitive camera 730. The image of the of the user's eye appears to the camera substantially as shown in FIG. 9, wherein the sclera (the white part of the eye) 901, the iris (the colored part of the eye) 902, and the pupil (the opening in the eye) 903 are visible. The center of the eye 910 is tracked, as shown by a first set of crosshairs 911, in relation to a reflection from the cornea (the outer surface of the eye) 920, as shown by a second set of crosshairs 921. The distance and direction of the difference between the center of the eye and the corneal reflection can be used to calculate the eye's position. Combined with a known distance to and size of a display, 740, the location at which the user is looking 702 can be determined. FIG. 8 shows the same application of eye tracking technology, but inside a VR headset 840. In FIG. 8, an infrared emitter 820 emits an infrared light 821, which is reflected off the user's eye 801 and cornea, and is received 832 at an infrared-sensitive camera 830. The distance and direction of the difference between the center of the eye and the corneal reflection can be used to calculate the eye's position. Combined with a known distance to and size of a display, 841, the location at which the user is looking 802 can be determined.

FIG. 10 is a diagram showing an embodiment in which on-screen virtual objects on a display are used to apply brainwave entrainment. In this example, brainwave entrainment is implemented using a display 1010, such as a television computer monitor, or tablet-based device, comprising a screen 1011 and in some configurations, built in speakers 1031a,b. In this embodiment, the screen 1011 is used to provide visual brainwave entrainment, either by flashing the background of the screen 1011 or one or more on-screen virtual objects 1020. This embodiment enables the provision of brainwave entrainment without the use of (or in addition to) external devices such as lights and speakers. In this example, five on-screen virtual objects 1020 are shown 1021-1025, each comprising a different shape and each moving independently on the screen 1011 as indicated by the dashed and dotted "movement shadows" associated with each on-screen virtual objects 1020. The on-screen virtual objects 1020 are generic shapes in this diagram, but may represent any type of on-screen element whether static or movable, permanent or transient. Depending on the configuration, the on-screen element may be any shape or color displayable on a screen, such as game elements, puzzle elements, background elements, regular or irregular portions of the screen. Many possible applications of this embodiment are possible. The built-in speakers, if any, may be used to provide auditory brainwave entrainment in addition to the visual on-screen brainwave entrainment.

For example, when paired with a camera and eye-tracking software, the on-screen virtual objects 1020 might represent an eye muscle strengthening exercise combined with brainwave entrainment, wherein the user is asked to find a target on-screen virtual object with a particular shape and follow the shape with his or her eyes. At the same time the target virtual object may flash a particular color at a selected brainwave entrainment frequency, with the color changing as the user's eyes either follow the target on-screen virtual object or stray from it. The target on-screen virtual object may, for example, be a pleasant light-blue color while the user's eyes are following it, and change to a bright red to re-attract the user if the user's eyes start following a different on-screen element.

In this embodiment, a clip-on eye-tracking unit 1040 may be attached to the display 1010 using plastic (or other material) clips 1044. The clip-on eye-tracking unit 1040 comprises a housing 1041, an infrared emitter 1042 which emits an infrared light that is reflected off the user's eye and cornea, and is received at an infrared-sensitive camera 1043, and clips 1044 which may be used to attach the clip-on eye-tracking unit 1040 to a display 1010. The center of the eye is tracked in relation to a reflection from the cornea (the outer surface of the eye). The distance and direction of the difference between the center of the eye and the corneal reflection can be used to calculate the eye's position. Combined with a known distance to and size of the display 1010 the location at which the user is looking can be determined.

In another use case, the on-screen virtual objects 1020 may represent a puzzle or game, and the brainwave entrainment may be provided by simply flashing the screen background 1012 at a selected brainwave entrainment frequency. This example may be extended to virtual reality applications, wherein brainwave entrainment is provided by flashing in-game elements within the virtual reality environment.

FIG. 11 is a diagram showing an exemplary virtual reality environment in which virtual objects may be used as visual stimulation transducers. The virtual reality environment show in this diagram depicts a quiet scene from a first person perspective, and would be suitable for brainwave entrainment related to theta or alpha wave entrainment (for example, to facilitate relaxation, creativity, exploration, and contemplation). The environment comprises a room with a floor 1110, a ceiling 1112, and three visible walls 1111*a-c*. In the ceiling are four recessed lights 1113. On the left wall 1111*a* is a flat-screen television 1123 showing an outdoor scene 1124 involving mountains, trees, and lightning. On the right wall hue is a door 1114. On the back wall is a window to the outside 1115 in which the sun can be seen 1130. In the corner of the room is a potted plant 1122, and next to the back wall 1111*b* is a table 1120 on which is standing a lamp 1121. Each and every virtual object named above can be used to provide brainwave entrainment. For example, any one or all of the virtual lighting objects, the lamp 1121, the television, 1124, the ceiling lights 1113, and the sun 1130 could be flashed or changed in intensity at the selected brainwave entrainment frequency. Even objects not associated with lighting, such as the walls 1111*a-c*, ceiling 1112, floor 1110, or door 1114, could be flashed or changed. If appropriate to the therapy regimen selected, exploration and curiosity could be encouraged by flashing certain objects (e.g., the television 1124, the potted plant 1122, the table 1120, the door 1114) as the user investigates or interacts with them. With some additions, a scene such as the one depicted here could be used to perform brainwave entrainment in a mystery or other storyline. Other modalities of brainwave entrainment such as sound and haptic feedback may be applied simultaneously with the visual stimulation. As more fully described above, these other modalities may be applied using either the same or different brainwave entrainment frequencies. As a non-limiting example, if a user in the virtual reality environment switches on the lamp 1121, not only might the lamp 1121 flash or change color at a brainwave entrainment frequency as a form of visual stimulation, an audible tone might be generated corresponding to the lamp flickering at the same entrainment frequency, and haptic feedback in the form of vibration of a game controller might also be applied. In some applications, for example in virtual environments comprising a darkened environment such as a room with the lights turned off, the visual stimulation may not be used, but the auditory and/or haptic stimulation modalities may continue to be applied.

FIG. 12 is a diagram showing exemplary gamification of brainwave entrainment in which in-game objects and elements are used as visual stimulation transducers in conjunction with gameplay activities. The gameplay example shown here depicts a first person shooter (FPS) involving shooting of attacking aliens, and would be suitable for brainwave entrainment related to beta or gamma wave entrainment (for example, to facilitate concentration, planning, or problem-solving). The environment comprises a laser gun 2120 controllable by the user, a spaceship 2112, a space background 2113 comprising stars 2110, and a plurality of attacking aliens 2111. The laser gun 2120 is shown here with a laser flash 2121, the resulting laser beam 2122, and its impact 2123 on one of the attacking aliens 2111. Each and every virtual object named above can be used to provide brainwave entrainment. For example, aliens 2111 may be flashed or changed as the user's attention focuses on them. The laser flash 2121, laser beam 2122, and impact 2123 can all be used to provide bright visual stimulation at an appropriate frequency during game play. Even the background 2113 and stars 2110 could be changed in color or brightness at an appropriate frequency.

In some embodiments, virtual reality environments and games could be used to provide entrainment opposite of the common expectation. For example, in the calm room shown in FIG. 11, gamma wave brainwave entrainment associated with concentration and planning could be applied to increase the user's awareness when in calm or innocuous-looking environments. Similarly, while playing an intense FPS such as that shown in FIG. 12, theta or alpha wave entrainment could be applied to calm the user during otherwise-intense game play. In a related use case where a user is addicted to the adrenalin received from intense game play, theta or alpha brainwave entrainment could be used to reduce the player's addition to games by calming the player during intense game play, reducing the adrenalin rush from playing highly-immersive, fast-action games with intense themes.

Other modalities of brainwave entrainment such as sound and haptic feedback may be applied simultaneously with the visual stimulation. As more fully described above, these other modalities may be applied using either the same or different brainwave entrainment frequencies. As a non-limiting example, when the user in the virtual reality environment shoots the alien 2111, not only might the impact 2123 provide visual brainwave entrainment, but an audible tone might be generated corresponding to the flashing or color changing of the impact 2123 at the same entrainment frequency, and haptic feedback in the form of vibration of a game controller might also be applied. In some applications, for example in virtual environments comprising a darkened environment, the visual stimulation may not be used, but the auditory and/or haptic stimulation modalities may continue to be applied.

FIG. 15 is a block diagram showing an exemplary modes of connectivity with for different users of a brainwave entrainment platform. Brainwave entrainment manager may be located centrally, accessible by multiple game clients, or may be located on end-user devices, accessible only by the game client on that device, or may be arranged in a distributed computing architecture across multiple computing devices and accessible by multiple game clients (this last configuration not shown), or any combination of the above. This diagram shows three possible modes of connectivity with a brainwave entrainment manager.

In a first exemplary configuration, game client D 1510 accesses cloud-based gaming platform 1300, receives game data and entrainment instructions from platform brainwave entrainment manager 1313. Client D 1510 converts the entrainment instructions to entrainment signals for display of virtual objects within the game world and displays them to user D as user D's perspective of the game world (or virtual experience). No feedback is provided, and it is simply assumed that user D is receiving the brainwave entrainment displayed.

In second exemplary configuration, game client E 1520 accesses cloud-based gaming platform 1300, receives game data and entrainment instructions from platform brainwave entrainment manager 1313. Client E 1520 converts the entrainment instructions to entrainment signals for display of virtual objects within the game world and displays them to user E 1521 as user E's 1521 perspective of the game world (or virtual experience). In this case, however, user E 1521 is wearing an electroencephalograph (EEG) device comprising a plurality of electrical sensors 1522 distributed about the head of user E 1521. The electrical sensors 1522 capture electrical signals produced by brain activity in certain locations of user E's 1521 brain, which act as a form of feedback as to the effect of brainwave entrainment on user E (i.e., brainwave entrainment is intended to impact certain brainwaves and (EEG signals are a direct measurement of electrical activity in the brain including brainwaves being produced by the brain). The EEG feedback is received by game client E 1520 which forwards it to platform brainwave entrainment manager 1313 for analysis and possible adjustment of brainwave entrainment instructions.

In third exemplary configuration, game client F 1530 accesses cloud-based gaming platform 1300, and receives game data only from cloud-based gaming platform 1300. Client E 1520 sends the game data to a client F brainwave entrainment manager 1533 operating on the same end-user device on which client F 1530 is operating. client F brainwave entrainment manager 1533 provides brainwave entrainment instructions to client F 1530, which converts the entrainment instructions to entrainment signals for display of virtual objects within the game world and displays them to user F 1531 as user F's 1531 perspective of the game world (or virtual experience). In this case, user F 1531 is wearing a heartrate monitor 1532 comprising a one or more electrical or optical sensors held in contact with the wrist or arm of user F 1531. The electrical sensors 1522 capture electrical signals produced by brain activity in certain locations of user E's 1521 brain, which act as a form of feedback as to the effect of brainwave entrainment on user E (heartrate signals are an indirect measurement the impact of brainwave entrainment on the user). The heartrate feedback is received by game client F 1530 which forwards it to on-board brainwave entrainment manager 1533 for analysis and possible adjustment of brainwave entrainment instructions.

Other configurations are possible, including combinations of the above configurations and different sensors and other means that may be used to obtain feedback such as blood pressure monitors, manual user feedback in the form of ratings of mood, etc.

FIG. 16 is are exemplary perspective diagrams showing shared experience gameplay with differential realities and brainwave entrainments. Typically in multiplayer online games, each player sees the same game world (i.e., in-game objects, characters, locations, and environmental details), but from different perspectives based on where the player's in-game character is located within the game world. However, for purposes of brainwave entrainment, displaying the same game world to different participants in a virtual experience may not be ideal. For example, where participants have different sensitivities, displaying of certain elements (e.g., depictions of blood) may hamper the intended effect of the brainwave entrainment for one or more of the participants (e.g., in cases where one of the players faints at the sight of blood) or may be inappropriate (e.g., where an adult is playing a computer game remotely with a child, it may be inappropriate to display depictions of scary, realistic monsters to the child). Further, participants may have different brainwave entrainment goals, even where they wish to engage in a shared experience or common activity. In such cases, differential versions of the game world and/or differential brainwave entrainment may be appropriate during the shared experiences.

In this example, two players are participating in the shared experience of a role-playing game, but have different sensitivities and brainwave entrainment goals. Player 1 wants a realistic experience, including depictions of realistic monsters, violence, and gore. Player 1 further wants excitement after a boring day at work, so is seeking brainwave entrainment that enhances his sense of danger. Thus, player 1's perspective 1610 shows a game world in which he is holding a realistically-rendered sword 1613, and facing a violent, realistically-rendered dragon 1612, with player 2 rendered in realistic armor 1611 to the dragon's right. The brainwave entrainment rendered in player 1's perspective 1610 may include pulsations, color changes, or movements of the dragon 1612 or other elements of the game world at frequencies intended to induce anxiety, stress, or danger.

Player 2 on the other hand is repelled by violence and gore, and uncomfortable with realistically rendered monsters. Player 2 wants to relax after a stressful day, and is seeking brainwave entrainment that instills a sense of calm. Player 2's perspective 1620, on the other hand, is a cartoonish rendering of the same scene, with the sword he is holding 1621 rendered in cartoon form, the dragon 1622 rendered as hapless and goofy, and player 1 rendered as a cartoon child 1623 to the dragon's left. The brainwave entrainment rendered in player 2's perspective 1610 may include pulsations, color changes, or movements of the dragon 1612 or other elements of the game world at frequencies intended to induce calm, relaxation, or contemplativeness.

This, while both players are engaging in a shared experience by playing the same role-playing game at the same time, the experience of each player will differ because of the differential rendering of the game world and differential brainwave entrainment of each player's perspective.

FIG. 20 is an exemplary diagram illustrating an exemplary application of machine learning to diagnose healthcare issues. In this example, a series of events leading to a health event are analyzed by a trained machine learning algorithm to identify and predict patterns that may lead to health issues, thereby allowing the machine learning algorithm to make diagnoses of similar health issues from similar patterns. In this example, a series of difficult-to-correlate events leads to a heart attack. Neural networks (a type of machine learning algorithm), trained on many, many similar events using back propagation, are able to connect and identify patterns of such events and build predictive models based on such training. Here, a traumatic health event occurs 2080, in this case a heart attack, and the system examines the previous events leading up to the heart attack through back propagation. In this example it sees several events occur for a user before the heart attack, including a heart irregularity identification event 2010 which can be an anomaly in the heartrate or pulse of a user, an exercise change event from running to cycling 2020, a group age identification event 2030 at which point the system identified the user as part of a new group of similar users due to current trends and user events, a training goal change event, indicating a goal to train for a cycling competition 2040, an individual age identification event 2050 which can occur due to an age change, or the user's age only now being input into the system, or may be the result of the system merely making note of the user's age in the back propagation even if the user's age did not change immediately prior to the heart attack, an exercise change event from cycling to rowing 2060, and an environmental change event, in this example a 10 degree shift in temperature of the surrounding environment 2070. Through examining similar series of events for large numbers of users and large amounts of data, the neural network is able to detect repeatable patterns in seemingly unrelated events which are predictive of health outcomes. Neural networks may be configured to detect such patterns within a single health-related factor. For example, a series of changes in a user's health profile that lead to a heart attack such as weight gain, followed by increased cholesterol levels, followed by high blood sugar levels. Neural networks may be used at a first stage to detect such patterns. More difficult to detect are patterns of health events across health factors. A neural network may be configured to analyze a confluence of factors to detect seemingly unrelated events that show a repeatable pattern of prediction of certain health outcomes. The example in this diagram shows, for example, a heart irregularity 2010 followed by a couple of age-related thresholds 2030 and 2050, combined with two type of exercise changes 2020 and 2060, a training goal change 2040, and a temperature change during exercise 2070. It is unlikely that these events would have been correlated with the heart attack by standard health prediction models, but neural networks excel at identifying such patterns and correlations over large sets of data.

FIG. 21 is a diagram of an additional exemplary exercise machine configured to capture physical and mental performance data for a cloud-based gaming platform with integrated healthcare diagnostics and treatment. According to the embodiment, a frame or structure 2120 surrounds or is directly attached to a treadmill device 2100 and has attachment points 2121a-n at varying heights for the previously disclosed torso and limbs harness 2110 or other wearable devices. The attachment points 2121a-n may be implemented as hooks, loops, or other connectors that allow the for accommodation of varying heights of users. The treadmill device 2100 comprising a curved form where the lowest point 2130 of the treadmill belt 2140 is behind the user and the highest point in front of the user 2131. As the user steps forward, towards the upwards curvature of the belt 2131, the user's foot strikes the belt, and gravity forces the belt back down towards the user returning to equilibrium.

Additionally, a non-powered electric motor 2150 is mounted internal to the treadmill 2100 and the treadmill belt 2140 is connected to the motor 2150 drive shaft. Pressure sensors 2160a-n mounted under the belt 2140 provide a computer system the users weight in which the computer uses to vary the electrical resistance of the motor 2150 such that the physical resistance and upwards curvature 2131 of the belt 2150 gives the user an experience of simulated forward motion indistinguishable from actual forward motion. The amount of electrical resistance between the leads of the motor 2150 may be adjusted to vary the resistance provided to the belt by the motor. Initially, the resistance between the leads of the electric motor can be set to keep the belt 2140 from moving too easily but allows the user to start moving the belt under the same friction and force as would naturally be required walking off of the treadmill 2100. Furthermore, the calculated electrical resistance used by the computer system may be used as a zeroing point, or baseline, so that the back-electromotive force created by the users motion on the belt 2140 can be used as a varying voltage input to a computer system. In some embodiments, a powered electric motor can be used to the same effect.

The pressure sensors 2160a-n may further be used to capture to position of the feet on the belt 2140 by calculating the transverse and sagittal axis force vectors relative to each sensor 2160a-n against the user's total weight. In the same fashion, shifting of the user's body may also be obtained. The pressure sensors 2160a-n capture vertical motion as the user walks, runs, bobs, jumps, or squats by considering the displacement and velocity measured on individual pressure sensors 2160a-n rather than relative to the others. Combining these measurements, the characteristics of a user's gait (e.g., step frequency, step impact, weight distribution, etc.) may also be obtained for use in computer applications.

According to this embodiment, the torso and limbs harness 2110 has sensors 2170a-n proximal to the user connected to tethers 2180a-n and may comprise flex sensors, strain gauges, or other force sensors. Additional embedded components within the torso and limbs harness 2110 comprise input sensors such as accelerometers, gyroscopes, magnetometers, motion, touch, smart health devices, MEMS (micro-electromechanical system) devices, and location sensors. The sensors 2171 may also be output sensors such as vibration motors, fans, actuators, piezoelectric discs, and other output devices designed to stimulate or alert the user.

The torso harness 2110 may be fastened by a plurality of tethers 2180a-n. In one embodiment, elastic tethers 2180a-n may be designed for a specific range of motion bound by maximum and minimum elasticity regarding all three planes of motion. The elasticity limits may be designed for physical safety (i.e., stumble, trip, or fall protection) while wearing a VR headset or by individuals suffering from diminished motor control such as physical rehabilitation, recent surgeries, or age-related decline. The range of motion may also be limited by sensors 2170a-n connected to the proximal (or distal) ends such as strain sensors with a limited sheer strength or axis sensors with multi-planar limits. It should be appreciated that the designed elasticity of the tethers 2180a-n may be a balance of both safety and physical limitations.

In this embodiment, the height of the tethers and belt may be adjusted by placing a loop on the distal end of each tether on one of a series of hooks. Other means of adjusting the height of the tethers and belt may be used, for example, telescoping poles, sliding hooks, or pulleys attached at a relatively high point from which the belt may be lowered by adjusting the length of the tether (either manually or via motors).

According to an additional embodiment, fixed length straps may be used or a combination of fixed and elastic tethers, or straps or belts connected to actuators or motors operated by a computer which controls the travel distance of each tether 2180a-n accordingly. Combination fixed and elastic tethers may use either separate non-elastic tethers or integrated non-elastic tether components to place a hard limit on the stretch length of each tether, which can provide additional load bearing capabilities to catch a user during a fall. Any number of embodiments may be imagined by those skilled in the art.

Affixed to the front of the treadmill is a motion sensing input device 2190. In this embodiment, the motion sensing input device comprises RGB cameras, infrared projectors and detectors that map depth, and a microphone array, along with artificial intelligence software to allow the device to perform real-time gesture recognition, skeletal detection, and fine and gross motor movement detection. In other embodiments, the motion sensing device may be simpler in operation, such as an ultrasonic distance sensor. Simpler versions of the motion sensing input device 2190 can be used to determine the user's body position front to back on the treadmill, whereas more complicated motion sensing input devices 2190 can be used to identify different parts of the body and their relative positions and directions (e.g., arms, legs, torso and limbs, head, etc.), as well as being combined with other sensors to confirm such actions as jumping and twisting motions. Another example is a sensor device that inserts into a user's shoe that can supplement additional details for gait analysis and a balance profile.

The treadmill 2100 comprising the self-propelled and variable-resistive belt 2140, motion sensing input device 2170, pressure sensors 2160a-n, tethers 2180a-n, and various torso and limbs harness embodiments described in FIGS. 1-4 provide the detailed tracking of both fine and gross motor skills covering the entire body. It should be appreciated that the dimensionality of input and body tracking and accuracy thereof provided by these embodiments allow for a broader range of control schemes and implementations than is available in the art. Besides the obvious implications for the VR/AR and gaming industry, this platform may assist in telehealth applications (i.e., remote health assessments and treatment) allowing doctors to diagnose and treat a range of ailments related to range of motion, physical therapy, balance, routine check-ups, geriatric care, and may be further extended by integrating heart rate monitors, blood-pressure monitors, electrocardiograms, and other smart wearable technology. Telehealth applications may be of particular use in sparsely populated areas or in other situations where in-person healthcare is limited, such as quarantines or where the patient is non-mobile.

FIG. 22 is a diagram illustrating exemplary physical data that can be captured by an exercise machine compatible with a cloud-based gaming platform with integrated healthcare diagnostics and treatment. According to this embodiment, pressure sensors under the treadmill belt may capture a user's gait 2210 by plotting the relative force between pressure sensors over time. Multiple datasets can be combined to improve the accuracy of the gait parameter calculations. For example, according to one embodiment, the first step of calculating the values of gait parameters is defining each gait cycle. One gait cycle can be defined as the period between successive maximum values on the front-right load sensor, indicating two successive ground contacts from the right foot. One gait cycle could also be defined as the period between successive ground contacts of the same foot using the camera body tracking data. Two sources of data for the same parameter provides for a more accurate analysis. The load sensor data could be integrated with the camera body tracking data to ensure that a gait cycle is not missed if the user fails to make contact with the front-right load sensor.

Accelerometers, gyroscopes, and/or magnetometers in the torso and limbs harness 2221 may be used to determine the harness's position by taking the second time derivative from the accelerometer readings. Twisting by the user in the harness 2221 may be measured and displayed 2222, 2223 by taking readings from the gyroscope and magnetometer, rotary encoders, or a combination of sensors given that linear velocity is equivalent to angular velocity multiplied by position. The amount of twist may be displayed by a gradient bar representing the typical limits of human contortion at the hips, or by any other metric desired by the user. In this example, the user has twisted to the left 2224 approximately one-quarter of the typical limit. Also, in this example, the user is forward and left from center 2225. In other embodiments, the camera 490 may be used in conjunction with markers on the torso and limbs harness to track movement (e.g., small colored balls could be attached to the harness and tracked by the camera 490).

Gross motor movements 2230 may be captured by a motion sensing device coupled with data from the sensors on the proximal and/or distal ends of the tethers and data from input sensors in the harness itself. A computer system may use the combination of data to position the user in a virtual environment, display the user's range of motion to a telehealth professional, or monitor the user's form during an exercise routine activating a vibrating motor if the user needs to correct their form.

Other positional data may be obtained and displayed via the plurality of sensors such as the harness's position 2241 relative to the resting or calibrated baseline position 2242. Data from the Y-Z harness position 2240 can detect jumps 2243 or squats 2244 by formulating thresholds of position and may further be verified or supplemented by the gross motor movements 2230 data and X-Y positional data 2220. In this example, the tilt of the harness is measured and displayed 2245 as the user squats meanwhile the harness position 2241 crosses the squat threshold 2244 indicating the user has in fact performed a squat.

FIG. 23 is an exemplary composite functioning score spatial map 2300 showing diagnostics of ability in several physical and mental functional measurement areas showing the relative ability of a user in several physical and mental functional measurement areas (also referred to herein as "composite functioning scores" or "composite functioning score groups") 2301-2307. The composite functioning score spatial map is a visual representation of a person's ability in several functional measurement areas 2301-2307. The center of the composite functioning score spatial map 2300 represents zero ability, while the inner circle 2310 of the composite functioning score spatial map 2300 represents full ability (i.e., maximum functionality of a healthy individual while not dual-tasking). Greater functionality in a given composite functioning score 2301-2307 is represented by a greater profile coverage area in the direction of that functional measurement area. The average profile area of a representative population of individuals (e.g., of the same age as the individual being tested) is shown as the solid line profile average 2311 of the composite functioning score spatial map 2300. The composite functioning score spatial map 2300 is a visual representation of data obtained from other components of the system and placed into a composite functioning score matrix or other data structure (not shown) which organizes the data relative to the various composite functioning scores.

In this example, there are seven groups of composite functioning scores, each representing either a physical ability, a mental ability, or a combined ability, and all of which together represent a picture of an individual's nervous system function. The memory 2301 and cognition 2302 composite functioning score groups represent purely mental activities, and present a picture of the individual's ability to think clearly. The speech 2303, auditory 2304, and vision 2305 composite functioning score groups represent combined physical/mental activities, as each represents some physical/mental interaction on the part of the individual. For example, speech requires the individual not only to mentally generate words and phrases on a mental level, but also to produce those words and phrases physically using the mouth and vocal cords. It is quite possible, for example, that the individual is able to think of the words, but not produce them, which represents one type of neurological condition. The speech 2303 composite functioning score group represents that combined ability, and the auditory 2304 and vision 2305 composite functioning score groups represent a similar combined ability. The motor skills 2306 composite functioning score group represents a mostly-physical ability to move, balance, touch, hold objects, or engage in other non-cognitive activities (recognizing, of course, that the nervous system controls those movements, but is not engaged in higher-level thinking). The emotional biomarker 2307 group represents the individual's emotional responses to certain stimuli during testing, as would be indicated by lack of empathetic responses to virtual reality characters in a story, responses indicating sadness or depression, etc.

From the data obtained from other components of the system, a profile of an individual's functional ability may be created and displayed on the composite functioning score spatial map. For example, a baseline profile 2308 may be established for an individual during the initial use or uses of the system (e.g., pre-treatment evaluation(s)), showing a certain level of ability for certain composite functioning scores. In the baseline profile 2308 example, all composite functioning scores indicate significant impairment relative to the population average 2311, but the composite functioning scores for cognition 2302 and auditory 2304 ability are relatively stronger than the composite functioning scores for memory 2301, speech 2303, vision 2305, and motor skills 2306, and the emotional biomarker group 2307 indicates substantial impairment relative to the population average 2311. Importantly, changes in the profile can show improvements or regressions in functionality, and changes over time in the profile can be tracked to show trends in improvement or regression. For example, a later profile 2309 for the same individual shows improvement in all biomarker groups, with substantial improvement in the cognition 2302, auditory 2304, motor skill 2306 biomarker groups, and dramatic improvement in the emotion 2307 composite functioning score groups, relative to the baseline profile 2308. The biomarker group for emotion 2307 in the later profile 2309 shows performance matching or nearly matching that of the population average 2311.

FIG. 24 is an exemplary system architecture diagram for a dual-task functional analysis system 2400 which may be used to capture and analyze physical and mental performance data for a cloud-based gaming platform with integrated healthcare diagnostics and treatment. In this example, the system comprises a data capture system 2500, a range of motion comparator 2600, a movement profile analyzer 2700, and a neurological functioning analyzer 2800. The data capture system 2500 captures data from sensors on the system such as motor speed sensors, angle sensors, accelerometers, gyroscopes, cameras, and other sensors which provide data about an individual's movement, balance, and strength, as well as information from software systems about tasks being performed by the individual while engaging in exercise. The range of motion comparator 2600 evaluates data from the data capture system 2500 to determine an individual's range of motion relative to the individual's personal history and relative to statistical norms, and to population averages. The movement profile analyzer 2700 evaluates data from the data capture system 2500 to generate a profile of the individual's physical function such as posture, balance, gait symmetry and stability, and consistency and strength of repetitive motion (e.g., walking or running pace and consistency, cycling cadence and consistency, etc.). The neurological functioning analyzer evaluates data from the data capture system 2500, the range of motion comparator 2600, and the movement profile analyzer 2700 to generate a profile of the user's nervous system function as indicated by composite functioning scores which indicate relative ability of an individual in one or more physical and mental functional measurement areas (also referred to herein as "composite functioning scores").

FIG. 25 is a system architecture diagram for a data capture system that may be used to capture data for a dual-task functional analyzer. In this embodiment, the data capture system 2500 comprises a physical activity data capture device 2510 designed to capture information about an individual's movements while the individual is engaged in a primary physical activity and a software application 2520 designed to assign primary tasks and associative activities, to engage the user in the physical tasks and associative activities, and track and store responses to tasks and activities, as well as a data integrator 2530 configured to convert, calibrate, and integrate data streams from the physical activity data capture device 2510 and software application 2520. The data capture system 2500 captures data from sensors 2511, 2512 on the physical activity data capture device 2510 such as motor speed sensors, angle sensors, accelerometers, gyroscopes, cameras, and other sensors which provide data about the speed, operation, direction and angle of motion of the equipment, and about an individual's movement, balance, and strength.

The physical activity data capture device 2510 may be any type of device that captures data regarding the physical movements and activity of a user. In some embodiments, the physical activity data capture device 2510 may be a stand-alone device not associated with the activity being performed (e.g. a camera, ultrasonic distance sensor, heat sensor, pedometer, or other device not integrated into exercise equipment). In other embodiments, the physical activity data capture device 2510 may be exercise equipment or peripherals that captures motion and activity information of a user engaged in physical activity while using the device. For example, the physical activity data capture device 2510 may be in the form of exercise equipment such as stand-on or ride-on exercise machines like treadmills, stair stepping machines, stationary bicycles, rowing machines, and weight-lifting or resistance devices, or may be other equipment wherein the user stands separately from the equipment and pulls or pushes on ropes, chains, resistance bands, bars, and levers. The physical activity data capture device 2510 may be in the form of computer peripherals (e.g., game controllers, virtual reality headsets, etc.) that capture data while the user is performing physical movements related to a game or virtual reality environment, or exercise equipment that engage the user in physical activity, such as barbells, free weights, etc., which are configured to provide location and/or motion information such an integrated motion sensors or external cameras configured to detect the peripheral. The physical activity data capture device 2510 may be in the form of exercise equipment or peripherals and may be referred to as an exercise device. Sensors in the physical activity data capture device 2510 may be either analog 2511 or digital 2512. Non-limiting examples of analog sensors 2511 are motor voltages and currents, resistors, potentiometers, thermistors, light sensors, and other devices that produce an analog voltages or currents. Most digital sensors are analog sensors 2511 with integrated analog-to-digital converters which output a digital signal, although some sensors are digital in the sense that they measure only discrete steps (e.g., an on/off switch). In most cases, signals from analog sensors 2511 will be converted to digital signals using an analog to digital converter 2501. For signals from digital sensors 2512, conversion is not necessary. In some cases, signals may need to be calibrated by a sensor calibrator, which corrects for sensor drift, out of range errors, etc., by comparing signals to known good values or to other devices.

The software application 2520 is any software designed to assign primary tasks and associative activities, to engage the user in the primary tasks and associative activities, and track and store data from primary tasks and responses to associative activities. The software application 2520 may have, or may use or access, a number of different software components such as a virtual reality game or environment generator 2521, an associative activity manager 2522 which designs, selects, and/or implements testing protocols based on the user's profile. Many different configurations of the software are possible. The software application 2520 may be configured to present tasks to the user independent of inputs from the physical activity data capture device 2510, such as performing playing games, performing math computations, remembering where certain symbols are located, visually following an object on a screen, or reading and speaking a given text. Alternatively, the software application 2520 may be configured to engage the user in mental or combined activities that correspond in some way to the inputs from the physical activity data capture device 2510. For example, the user might be running on a treadmill, and the speed of the treadmill might be used as an input to a virtual reality environment which shows the user virtually running at a rate corresponding to the rate of the real world treadmill speed. The software application 2520 is configured to record data regarding, or evaluate and assign scores or values to, the user's responses and reactions to the tasks presented by the software application 2520. For example, if the user is assigned the task of performing a mathematical calculation, the correctness of the user's response may be evaluated, scored, and recorded as data. As another example, the user may be presented with the task of speeding up or slowing down a running motion in response to a visual cue, and the speed of the user's reaction may be recorded as data. In such cases, a data integrator 2530 may be used to integrate the data from the physical activity data capture device 2510 with the data from the software application 2520. In some embodiments, the data from the physical activity data capture device 2510 may be used to change the operation of the software application 2520, and vice versa (i.e., the software application 2520 may also be used change the operation of the exercise equipment, for example, providing additional resistance or speeding up the operation of a treadmill). In some embodiments, the data integrator may not be a separate component, and its functionality may be incorporated into other components, such as the software application 2520.

In some embodiments, the software application 2520, another machine-learning based software application such as a task assignment software application (not shown), may be configured to assign physical tasks to the user to be performed in conjunction with the associative activities assigned. Rather than simply performing continuously performing physical activity and recording the impact on the primary task of performance of the associative activities, the user may be assigned discrete physical tasks to perform while a mental activity is being performed. For example, the user may be assigned the physical task of pointing to a fixed spot on a display screen while reading aloud a text, and the steadiness of the user's pointing may be measured before, during, and after the reading, thus indicating an impact on the user's physical activity of the mental effort. Such dual-task testing may allow for more precise measurement and evaluation of relative functioning as different combinations of primary and associative activities are evaluated together. In some embodiments, the associative activity may be a second physical task or activity assigned to be performed simultaneously with a primary physical task or activity. Note that the terms "task" and "activity" as used herein are interchangeable, although the phrases "primary task" and "associative activity" are often used for purposes of clarity and convenience.

FIG. 26 is a system architecture diagram for a range of motion analyzer aspect of a dual-task functional analysis system. The range of motion and performance comparator 2600 evaluates data from the data capture system 2700 to determine an individual's range of motion and performance for the given associative activity relative to the individual's personal history and relative to statistical norms. The range of motion and performance comparator 2600 comprises a current range analyzer 2601, a historical range comparator 2602, a statistical range comparator 2603, and a range of motion and performance profile generator 2604, as well as databases for user range of motion and performance historical data 2610 and demographic data 2620. The current range analyzer 2601 ingests data related to an individual's movement and performance, and calculates a range of motion and performance of that individual while performing versus not performing the given associative activity. For example, if an individual is given a primary physical task of standing in balance and an associative activity of popping a virtual balloon of a specific color as it appears randomly in the VR environment, the current range analyzer 2601 will start tracking the individual's balance while performing the associative activity and measure the accuracy and timing of balloon popping (for testing the individual's gross motor and executive functions). To conclude, the individual is instructed to start walking to warm up, and then repeat the same balloon popping activity while walking. The current range analyzer 2601 will finish capturing all the motion and performance data—the differences in the individual's accuracy and timing of balloon popping between standing and walking as well as the nuanced changes in the individual's walking movement during warmup and while balloon popping—and forwarding its analysis to the historical range comparator 2601. The historical range comparator 2602 retrieves historical data for the individual (if such exists) from a user range of motion and performance historical data database 2610, and compares the current data with historical data to determine trends in the individual's motion and performance over time. The statistical range comparator 2603 retrieves statistical range data for populations similar to the individual from a demographic data database 2620, and determines a range of motion and performance of the individual relative to similar individuals by sex, age, height, weight, health conditions, etc. The range of motion and performance profile generator 2604 takes the data from the prior components, and generates and stores a range of motion profile for the individual which integrates these analyses into a comprehensive picture of the individual's range of motion functionality.

FIG. 27 is a system architecture diagram for the movement profile analyzer aspect of a dual-task functional analysis system. The movement and performance profile analyzer 2700 evaluates data from the data capture system 2700 to generate a profile of the individual's physical function such as posture, balance, gait symmetry and stability, and consistency and strength of repetitive motion (e.g., walking or running pace and consistency, cycling cadence and consistency, etc.) and mental performance such as executive function, cognitive response, visual and auditory functions, emotional or empathetic reactions, etc. The movement and performance profile analyzer 2700 comprises a number of component analyzers 2701*a-n*, a historical movement and performance profile comparator 2702, a statistical movement and performance comparator 2703, and a movement and performance profile generator 2704, as well as a user movement and performance profile history data database 2710 and a demographic data database 2720.

Many different aspects of movement and performance may be analyzed by the movement and performance profile analyzer 2700 through one or more of its many component analyzers 2701*a-n* such as the gait analyzer, balance analyzer, gross motor analyzer, fine motor analyzer, depth perception analyzer, executive function analyzer, visual function analyzer, auditory function analyzer, memory function analyzer, emotional response analyzer, etc. For example, the gait analyzer of the component analyzers 2701 ingests sensor data related to an individual's ambulatory movements (walking or running) while performing the given associative activity, and calculates a step frequency, step symmetry, weight distribution, and other metrics related to an individual's gait. These calculations are then compared to expected calculations for an individual without performing the given the associative activity. If an individual exhibits a limp while performing the given associative activity (e.g., popping virtual balloons), the step frequency, step symmetry, and weight distribution will all be skewed with the impaired side showing a shorter step duration and less weight applied. The expected calculations may be determined from the full range of sensor values, per-exercise calibrations, statistical data, or other means appropriate to the specific application. The balance analyzer of the component analyzer 2701 performs a similar function with respect to an individual's balance. Wobbling, hesitation, or partial falls and recoveries while performing a range of associative activities can be calculated from the data. The historical movement and performance comparator 2702 retrieves historical data for the individual (if such exists) from a user movement and performance historical data database 2710, and compares the current movement and performance data with historical data to determine trends in the movements and performances over time. The statistical movement and performance comparator 2703 retrieves statistical range of motion and performance data for populations similar to the individual from a demographic data database 2720, and compares movements and performances of the individual to similar individuals by sex, age, height, weight, health conditions, etc. The movement and performance profile generator 2705 takes the data from the prior components, and generates and stores a movement and performance profile for the individual which integrates these analyses into a comprehensive picture of the individual's movement and performance functionality.

FIG. 28 is a system architecture diagram for a neurological function analyzer aspect of a dual-task functional analysis system. The neurological functioning analyzer 2800 evaluates data from the data capture system 2500, the range of motion and performance comparator 2600, and the movement and performance profile analyzer 2700 to generate a profile of the user's nervous system function as indicated by composite functioning scores which indicate relative ability of an individual in one or more physical and mental functional measurement areas (also referred to herein as "composite functioning scores"). The current composite functioning score analyzer 2801 ingests sensor data related to an individual's movement and performance, and calculates a set of current composite functioning scores for that individual based on the sensor data, the range of motion and performance profile, the movement and performance profile, and input from the software 2520 regarding associative activities associated with physical movement data. The historical composite functioning score comparator 2802 retrieves historical data for the individual (if such exists) from a user composite functioning score historical data database 2810, and compares the current composite functioning score data with historical data to determine trends in the individual's bio-makers over time. The statistical composite functioning score comparator 2803 retrieves statistical composite functioning score data for populations similar to the individual from a demographic data database 2820, and determines a range of composite functioning score functionality of the individual relative to similar individuals by sex, age, height, weight, health conditions, etc. The neurological functioning profile generator 2804 takes the data from the prior components, and generates and stores a neurological functioning profile for the individual which integrates these analyses into a comprehensive picture of the individual's composite functioning score functionality. In some embodiments, one or more of the composite functioning scores may be determined from dual-task testing, in which a physical task and a mental task are performed simultaneously to detect areas of abnormal nervous system function, and/or identify which areas of the nervous system may be affected. For example, while performing mathematical tasks, an individual slows down significantly in his/her walk compared to the population data. It will indicate that the individual's composite functioning score for logical and mathematic functions is worse than his/her population cohort (by sex, age, height, weight, health conditions, etc.). The neurological functioning profile may include a composite functioning score spatial map as described above. In some embodiments, the neurological functioning analyzer may receive data directly from the data capture system 2500 and may perform independent neurological analyses without inputs from the range of motion and performance comparator 2600 or the movement and performance profile analyzer 2700, or may incorporate some or all of the functionality of those components.

FIG. 29 is a diagram showing exemplary health data collection devices usable for collection of health data. Here, a variety of devices that could be used to collect health-related data are shown, including a treadmill with integrated sensors 2910, various wearable devices 2920, an external camera 2930, devices operated by another person 2940, and healthcare or medical records storage device 2950. Each of these devices may be capable of wireless connectivity with other devices, in the manner shown at 2960. Since, health-related information captured and transferred from these devices will likely contain HIPPA-protected health data, connection to, and transfer of, records from these devices should be done through HIPPA-compliant health data tunnel 1702 or its equivalent.

Treadmill with integrated sensors 2910 described herein should be considered complementary to that described in FIG. 21 above. Treadmill with integrated sensors 2910 has a frame supporting a rigid running platform 2912 across which the top portion of a treadmill belt 2911 slides while in operation. Running platform 2912 may have one or more pressure sensors (also known as force sensors, load sensors, and strain gauges) integrated into it 2913 and configured to provide data regarding the times, durations, and amounts of force each sensor receives. The pressure sensors 2913 may further be used to capture to position, weight, and timing of the feet on the belt 2911 by calculating vertical, transverse, and sagittal force vectors relative to each sensor 2913 against the user's total weight. In the same fashion, shifting of the user's body may also be obtained. Motions such as walking, running, jumping, shifting, and squatting may be calculated by applying appropriate algorithms to the vertical, transverse, and sagittal force vectors calculated. Combining these measurements, the characteristics of a user's gait (e.g., step frequency, step impact, weight distribution, etc.) may also be obtained as health-related data. In some embodiments, pressure sensors 2915 may be integrated into legs or supports 2914 of the treadmill in addition to, or in substitution of, pressure sensors 2913 integrated into running platform 2912. This configuration of pressure sensors 2915 allows for pressure sensors 2915 to be added to treadmills not manufactured with such sensor capability simply by mounting the entire treadmill on external legs or supports having such pressure sensors 2915. Treadmill with integrated sensors 2910 may have a computer 2916 comprising a display and wireless networking, capable of transmitting data to and from other devices.

Wearable devices 2920 usable for capturing health-related data include, but are not limited to, virtual reality headsets 2921, respiration masks and sensors 2922, chest-mounted sensors 2923, waist belts 2924, arm mounted sensors 2925, wrist-mounted sensors, and pressure sensors 2927 integrated into the soles of shoes.

Virtual reality headset 2921 may capture health-related data related to head and neck movements by using integrated magnetometers, accelerometers, and gyroscopes to determine head pitch, yaw, and roll motions of virtual reality headset 2921. Health-related data related to head and neck movements may be used to determine range of motion issues and to test balance and coordination issues. To capture head and neck movement data, users may be encouraged by games or tasks requiring the user to look up, down, left, and right at various virtual objects or follow various virtual objects in certain directions as far as the user's head and neck allow. Such testing can be performed as part of dual-task testing by assigning head and neck movements as a primary task (e.g., a physical task designed to determine range of motion of the head and neck) or as an associative task (e.g., to test balance or coordination as an associative task while performing a primary task such as walking or running) of dual-task testing. This head and neck range of motion data can be used to detect physical ailments such as limited range of motion (e.g., as a consequence of a neck injury) or can be used to detect parasympathetic nervous system issues such as balance problems or motion sickness. In some embodiments, virtual reality headset 2921 may comprise electro-encephalography (EEG) sensors for capturing electrical signals from brain activity. EEG data is health-related data that may be used to Respiration masks and sensors 2922 may be used to capture health-related data such as oxygen consumption during exercise. For example, one indicator of physical fitness is called a maximum volume of oxygen (VO2 Max) measurement, which measures the maximum volume of oxygen processed by the body during exercise (typically in milliliters of oxygen per kilogram of body weight). A higher VO2 Max measurement indicates a higher level of cardiovascular fitness.

Pressure sensors integrated into the soles of shoes 2927 can act like pressure sensors 2913, 2915 in a treadmill as described above, and can capture the same or similar data, allowing for capture and calculation of health-related data such as gait analysis as described for treadmill with integrated sensors 2910 above. Pressure sensors integrated into the soles of shoes 2927 may be used to capture to weight and timing of the feet as they strike a ground surface by calculating vertical, transverse, and sagittal force vectors relative to each sensor 2913 against the user's total weight and, combined with a global positioning sensor (either integrated into the shoes or as an external device such as a GPS running watch), can be used to calculate position of the user. Shifting of the user's body and motion such as walking, running, jumping, shifting, and squatting may be calculated by applying appropriate algorithms to the vertical, transverse, and sagittal force vectors calculated. Combining these measurements, the characteristics of a user's gait (e.g., step frequency, step impact, weight distribution, etc.) may be obtained as health-related data.

Chest-mounted sensors 2923, waist belts 2924, arm-mounted sensors 2925, and wrist-mounted sensors may be fitted with a variety of sensors that can capture health-related data. Each of these devices may comprise a network adapter, a processor, and a memory, such that the sensor data may be processed and the device may transmit the health-related data to and from other computing devices such as smartphones. Sensors fitted into such devices capable of capturing health-related data include, but are not limited to, optical and electrical heart rate monitors for capturing heart rate, electromyography (EMG) sensors for capturing electrical activity in muscles and the nerve cells that control the muscles, plethysmographs for detecting blood pressure, optical pulse oximeters for measuring blood-oxygen saturation, and temperature sensors for measuring body temperature.

External camera 2930 may be used to capture visible health-related data such as facial images, body position, and perspiration. Facial recognition software can be applied to captured facial images to determine facial expressions indicating emotions or indications of physical conditions such as pain or discomfort. Facial expressions indicating emotions can be used as health-related data associated with mental health, and facial expressions indicating physical conditions can be used as health-related data regarding fitness, physical ailments or disabilities, and the like. Body position can be used to identify (or confirm) problems with gait or posture, which may be associated with various physical and/or neurological conditions. In certain circumstances, perspiration may be an indicator of various conditions such as heat exhaustion or lack of fitness.

Devices operated by another person 2940 may be used to capture health-related data wherein another person such as a healthcare professional or coach (e.g., doctor, nurse, psychiatrist, etc.) 2942 uses a data entry device 2941 to enter health-related data about a person. For example, a healthcare professional 2942 may take notes or enter data on data entry device 2941 while a person is engaged in physical exercise or dual-task testing, or during the course of an interview with the person about his or her health. Health-related data entered on data entry device 2941 may include, but is not limited to, patient subjective descriptions of health, doctor or nurse notes about perceptions of the patient's health, data from medical testing such as blood testing, direct observations of patient conditions such as mood (happy, sad, depressed, etc.), speech patterns (normal, slurred, stuttering, etc.), cognitive function (normal, age-related memory loss, mild to severe dementia, etc.), pain or injury, and the like.

Healthcare or medical records storage device 2950 may be accessed to retrieve previously-obtained and stored health-related information such as patient records, previous medical testing, previous diagnoses, and the like. Healthcare or medical records storage devices 2950 will comprise some form of healthcare/medical databases 2952 which may be accessed via a healthcare computer 2951, for example an administrative computer or server at a doctor's office or other medical facility. Since, health-related information stored on healthcare or medical records storage devices 2950 will likely contain HIPPA-protected health data, connection to, and transfer of, records from healthcare or medical records storage devices 2950 should be done through HIPPA-compliant health data tunnel 1702 or its equivalent.

FIG. 30 is a diagram showing exemplary health-related social data collection. Health-related social data may be useful in diagnosing both physical conditions and mental conditions. Health-related comprises data from one or more of several interconnected individuals and groups, each of which provides a different perspective of a person's overall social behaviors, thus making the available data on any given issue richer and deepening the analyses that may be performed. For example, the individual may self-report no issues of depression and his or her gaming group may report no depression because of their limited interactions, but a decrease in game performance combined with evidence of distance from family and non-gaming friends may suggest some form of depression. Health-related social data may include, but is not limited to, localized information or information from close-knit social groups such as self-reporting 3010, information from gaming groups 3020 with which a person is associated, information from non-gaming social groups 3030, information from the family of the person 3040, and may further include, but is not limited to, information from broader or more remote social groups and associations such as regional, national, and international societies and organizations 3050 such as online competitions 3051 and other gaming groups 3052.

Self-reporting 3010 comprises information a person reports about himself or herself such as survey answers, statements made in in-game chats and messaging, and statements made to healthcare professionals, coaches, trainers, or other non-gaming-related persons.

Information from gaming groups 3020 with which a person is associated comprises information that may be obtained from individuals in a person's gaming group or team such as in-game chats, in-game performance, system logs, and group reporting. For example, a person's in-game performance may decline, prompting other group members to chat amongst themselves that the person "seems depressed," and system logs may show that the person's gaming logins have reduced significantly in recent days or weeks, all of which may suggest that the person is depressed or has some other mental health or cognitive condition.

Information from non-gaming social groups 3030 comprises information from other social groups outside of the person's gaming life, such as hobby or special-interest groups, data about which may be captured from social media feeds, chats, messaging, and other such sources. Such data may be used in the same way as for information from gaming groups 3020 above. Comparisons between information from gaming groups 3020 and social groups 3030 such as health trend comparisons may be used to yield additional health-related insights about the person.

Information from the family of the person 3040 comprises information from the person's family, which may be captured from social media feeds, chats, messaging, and other such sources. Such data may be used in the same way as for information from gaming groups 3020 above. Comparisons between information from gaming groups 3020 and family 3040 such as health trend comparisons may be used to yield additional health-related insights about the person.

Information from broader or more remote social groups and associations such as regional, national, and international societies and organizations 3050 comprises information larger, more remote, or less closely-affiliated social groups, such as regional, national, and international societies and organizations, hobby or special-interest groups, and competitions 3051 (wherein gamers or competitors may meet one another periodically but may not have regular social interactions) and other gaming groups (for example team games where the teams may meet regularly to play cooperatively or competitively). Data from societies and organizations 3050 may be captured from social media feeds, chats, messaging, news feeds, web logs (also known as blogs), and other such sources. For competitions 3051, data may further comprise performance trends, leader boards, and similar competitive data. For other gaming groups 3052, data may further comprise inter-group chats, group health trend comparisons, as well as data similar to gaming group 3020 data such as in-game chats, in-game performance, system logs, and group reporting. All such data may be used in the same way as for information from gaming groups 3020 above. Comparisons (such as health trend comparisons) between information from localized information or information from close-knit social groups such as gaming groups 3020 and social groups 3030 and information from broader or more remote social groups and associations such as societies and organizations 3050 may be used to yield additional health-related insights about the person.

FIG. 31 is diagram showing exemplary methods for in-game data collection. This diagram shows an exemplary screenshot 3110 of a first-person (player) perspective of a three-dimensional game during game play and a corresponding map 3120 representing available pathways during gameplay. In this embodiment, map 3120 represents an internal logical of the game and is not visible to player. Pathways within map 3120 are represented visually to player as roads 3111 in screenshot 3110. Screenshot 3110 further shows terrain comprising hills 3112, a series of signposts 3130 located at road 3111 intersections containing (in this embodiment) mathematical equations to be solved by player. Screenshot 3110 further shows obstacles 3140 which in this embodiment are two tanks 3141, 3142 advancing toward player.

A variety of health-related data may be captured from this exemplary game during game play. A first non-limiting type of health-related data that may be captured is data related to player's ability to remember pathways. As map 3120 is not visible to the player, player must remember which series of turns and pathways will lead player from the beginning to the end of map. Correct turns may be rewarded and wrong turns may be penalized (e.g., with points or scores) or the total time to complete map 3120 from beginning to end may be used as the scoring or measurement variable. Time to complete map may be tracked from one play to another (or alternately, player map be shown map 3120 for a period of time at the beginning of game play, and instructed to remember the pathway from beginning to end). Thus, memory is one cognitive function for which health-related data may be captured as in-game data.

Another non-limiting type of health-related data that may be captured as in-game data is cognitive function associated with problem-solving. Player may be instructed to solve the brief mathematical equations on signposts 3130 during game play, whereby solving an equation correctly provides an indication as to the proper path to take at each intersection. The number of problems correctly solved is a measurement of a particular type of problem-solving cognitive function. Alternately, or in addition, the faster such problems are solved by player, the faster player's completion of map 3120 will be, and time to completion of map 3120 may also be used an a measurement of problem-solving ability. While mathematical equations are shown on signposts 3130 in this embodiment, any type of problem, puzzle, brain-teaser, or cognitive task may be used to measure aspects of cognitive function. In some embodiments, physical tasks such as touching the screen (e.g., to pop on-screen virtual bubbles) or pressing an indicated button within a defined period of time may be used to test reflexes and recognition of certain objects, wherein performance of the physical task within the defined period of time results in rewards and/or higher scoring.

A third non-limiting type of health-related data that may be captured as in-game data is reaction time or cognitive processing time to an in-game event. For example, tanks 3141, 3142 may fire projectiles at player which player must perceive and dodge (or knock down with counter-fire) before being struck by them. The time from firing of each projectile to player's reaction to it may be tracked, providing health-related data as to player's reaction time or cognitive processing time to an in-game event. Player's success rate in dealing with projectiles may also be tracked (for example, as a modifier to player's reaction time or cognitive processing time). Projectiles may be of a plurality of types (e.g., green, representing powerups or red, representing damage), forcing player to further distinguish cognitively between projectiles.

Each of the types of activities described above may be assigned as associative activities for dual-task testing. For example, player may be assigned a primary task of running on a real-world treadmill 2910 while playing the game indicated in screenshot 3110 through a virtual reality headset 2921. Player's running speed on the real-world treadmill 2910 may drive player along roads 3111 from beginning to end of map 3120. Physical health-related data for player may be captured during game play (i.e., while player is running on the real-world treadmill 2910) such as player's gait, running speed, heart rate, blood pressure, respiratory rate, and VO2 Max, all of which may be captured by health-related data capture devices such as those described in FIG. 29. Simultaneously, player may be assigned one or more associative tasks during game play such as the activities described for the three non-limiting types of health-related data capture above. Thus, both physical function health-related data (typically associated with a primary task) and mental function health-related data (typically associated with an associative task) may be captured simultaneously, allowing for the influence of primary tasks on associative activities to be determined, and vice-versa. For example, increases in stress associated with faster running are likely to result in decreases in cognitive performance tasks, and the changes can be tracked and compared to both player and statistical norms to diagnose a variety of physical function and mental function conditions. Aspects of mental function may be measured by in-game activities in areas such as language, memory, cognition, attention, abstraction, and perception. Aspects of physical function may be measured by both in-game and extra-game (i.e., running on a treadmill) activities in areas such as balance, coordination, range of motion, fitness, reaction times, and gross and fine motor function (i.e., activity that results from stimulation of motor neurons).

FIG. 32 is diagram showing exemplary data from in-game data collection. This diagram shows an exemplary screenshot 3200 containing exemplary data reports 3210, 3220, 3230 of health-related data captured while playing the exemplary game shown in FIG. 31. In the first column 3210, in-game performance data from player's third game play attempt is shown comprising an overall time to finish (i.e., overall performance) score of 2 minutes 34 seconds 3211, scores associated with cognitive tasks 3212 showing 5 correct turn choices out of 8 (62.5%) and three out of eight (37.5%) math problems correctly solves, scores associated with a physical task (in this example, running on treadmill 2910 during game play) showing a gait rhythm regularity of 85 out of 100 (85%) and a gait left/right balance of 37 left/63 right (suggesting a substantial favoring of the right leg), and reaction time performance data 3214 showing 5/9 (55.5%) of tank projectiles dodges and an average reaction time from firing of each projectile of 0.25 seconds.

Each of the above scores may be compared with player's performance history or one or more statistical data sets. Here, two such exemplary statistical data sets are shown, a performance versus age cohort data set 3220 and a performance versus age cohort with a known Condition X associated with a particular type of cognitive impairment 3230, with score values of player's third attempt 3210 shown by slider bars indicating performance of player for that score relative to the indicated cohort. In 3220, player's time to finish score 3211 and reaction time scores 3214 are about average for the cohort data set 3220, suggesting normal or expected performance. However, player's cognitive function scores 3212 are substantially lower than would be expected for player's age cohort 3221, suggesting some cognitive impairment. The cognitive function scores of players of the same age cohort but with Condition X 3230 are higher than for player, suggesting that player's cognitive impairment is not related to Condition X. Similar comparisons may be made for the other scores among player's data 3210, age cohort data 3220, and age cohort data with Condition X. Similar analyses may be performed using health-related in-game performance data using other data sets or other means of analysis such as those described for healthcare diagnostics & treatment module 1800 above.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the embodiments disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific embodiments, at least some of the features or functionalities of the various embodiments disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some embodiments, at least some of the features or functionalities of the various embodiments disclosed herein may be implemented in one or more virtualized computing environments (e.g., network computing clouds, virtual machines hosted on one or more physical computing machines, or other appropriate virtual environments).

Referring now to FIG. 33, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one embodiment, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one embodiment, a computing device 10 may be configured or designed to function as a server system utilizing CPU 12, local memory 11 and/or remote memory 16, and interface(s) 15. In at least one embodiment, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some embodiments, processors 13 may include specially designed hardware such as application-specific integrated circuits (ASIC s), electrically erasable programmable read-only memories (EEPROMs), field-programmable gate arrays (FPGAs), and so forth, for controlling operations of computing device 10. In a specific embodiment, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one embodiment, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 33 illustrates one specific architecture for a computing device 10 for implementing one or more of the inventions described herein, it is by no means the only device architecture on which at least a portion of the features and techniques described herein may be implemented. For example, architectures having one or any number of processors 13 may be used, and such processors 13 may be present in a single device or distributed among any number of devices. In one embodiment, a single processor 13 handles communications as well as routing computations, while in other embodiments a separate dedicated communications processor may be provided. In various embodiments, different types of features or functionalities may be implemented in a system according to the invention that includes a client device (such as a tablet device or smartphone running client software) and server systems (such as a server system described in more detail below).

Regardless of network device configuration, the system of the present invention may employ one or more memories or memory modules (such as, for example, remote memory block 16 and local memory 11) configured to store data, program instructions for the general-purpose network operations, or other information relating to the functionality of the embodiments described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

In some embodiments, systems according to the present invention may be implemented on a standalone computing system. Referring now to FIG. 34, there is shown a block diagram depicting a typical exemplary architecture of one or more embodiments or components thereof on a standalone computing system. Computing device 20 includes processors 21 that may run software that carry out one or more functions or applications of embodiments of the invention, such as for example a client application 24. Processors 21 may carry out computing instructions under control of an operating system 22 such as, for example, a version of MICROSOFT WINDOWS™ operating system, APPLE MACOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 33). Examples of storage devices 26 include flash memory, magnetic hard drive, CD-ROM, and/or the like.

In some embodiments, systems of the present invention may be implemented on a distributed computing network, such as one having any number of clients and/or servers. Referring now to FIG. 35, there is shown a block diagram depicting an exemplary architecture 30 for implementing at least a portion of a system according to an embodiment of the invention on a distributed computing network. According to the embodiment, any number of clients 33 may be provided. Each client 33 may run software for implementing client-side portions of the present invention; clients may comprise a system 20 such as that illustrated in FIG. 34. In addition, any number of servers 32 may be provided for handling requests received from one or more clients 33. Clients 33 and servers 32 may communicate with one another via one or more electronic networks 31, which may be in various embodiments any of the Internet, a wide area network, a mobile telephony network (such as CDMA or GSM cellular networks), a wireless network (such as WiFi, WiMAX, LTE, and so forth), or a local area network (or indeed any network topology known in the art; the invention does not prefer any one network topology over any other). Networks 31 may be implemented using any known network protocols, including for example wired and/or wireless protocols.

In addition, in some embodiments, servers 32 may call external services 37 when needed to obtain additional information, or to refer to additional data concerning a particular call. Communications with external services 37 may take place, for example, via one or more networks 31. In various embodiments, external services 37 may comprise web-enabled services or functionality related to or installed on the hardware device itself. For example, in an embodiment where client applications 24 are implemented on a smartphone or other electronic device, client applications 24 may obtain information stored in a server system 32 in the cloud or on an external service 37 deployed on one or more of a particular enterprise's or user's premises.

In some embodiments of the invention, clients 33 or servers 32 (or both) may make use of one or more specialized services or appliances that may be deployed locally or remotely across one or more networks 31. For example, one or more databases 34 may be used or referred to by one or more embodiments of the invention. It should be understood by one having ordinary skill in the art that databases 34 may be arranged in a wide variety of architectures and using a wide variety of data access and manipulation means. For example, in various embodiments one or more databases 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some embodiments, variant database architectures such as column-oriented databases, in-memory databases, clustered databases, distributed databases, or even flat file data repositories may be used according to the invention. It will be appreciated by one having ordinary skill in the art that any combination of known or future database technologies may be used as appropriate, unless a specific database technology or a specific arrangement of components is specified for a particular embodiment herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, most embodiments of the invention may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments of the invention without limitation, unless a specific security 36 or configuration system 35 or approach is specifically required by the description of any specific embodiment.

FIG. 36 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to keyboard 49, pointing device 50, hard disk 52, and real-time clock 51. NIC 53 connects to network 54, which may be the Internet or a local network, which local network may or may not have connections to the Internet. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various embodiments, functionality for implementing systems or methods of the present invention may be distributed among any number of client and/or server components. For example, various software modules may be implemented for performing various functions in connection with the present invention, and such modules may be variously implemented to run on server and/or client components.

The skilled person will be aware of a range of possible modifications of the various embodiments described above. Accordingly, the present invention is defined by the claims and their equivalents.

What is claimed is:

1. A health-related data collection system for healthcare diagnostics and treatment platforms, comprising:
    a piece of exercise equipment comprising a sensor configured to provide a first set of health-related data about a physiological aspect of a person using the exercise equipment while engaged in a virtual reality environment;
    a network-connected computing device comprising a memory and a processor;
    a frontend service comprising a first plurality of programming instructions stored in the memory which, when operating on the processor, causes the network-connected computing device to:
        receive a network connection from a game client, the game client operating on a remote computing device associated with the person and configured to transmit health-related information about the person to the frontend service;
        operate the virtual reality environment for engagement by the person while exercising on the exercise equipment, wherein the virtual reality environment is configured to capture a second set of health-related data about the person via in-game activities performed by the person while engaged in the virtual reality environment;
        transmit virtual reality environment data to the game client, the virtual reality environment data comprising data for rendering of the virtual reality environment on the remote computing device on which the game client is operating; and
    a HIPPA-compliant security gateway comprising a second plurality of programming instructions stored in the memory which, when operating on the processor, causes the network-connected computing device to:
        establish a HIPPA-compliant health data tunnel with the game client;
        direct the game client to send the first and second sets of health-related data to the HIPPA-compliant security gateway via that HIPPA-compliant health data tunnel; and
        store the health-related data in a patient database.

2. The system of claim 1, wherein the physiological aspect is selected from the list of step location, step pressure, and step timing, heart rate, blood pressure, blood-oxygen saturation, volume of oxygen maximum (VO2 Max), body temperature, and electrical activity in muscles and nerve cells that control the muscles.

3. The system of claim 2, further comprising a physical function evaluator comprising a third plurality of programming instructions stored in the memory which, when operating on the processor, causes the network-connected computing device to calculate a physical function from the physiological aspect, wherein the physical function is selected from the list of gait symmetry, gait rhythm, balance, coordination, range of motion, fitness, reaction times, gross motor function, and fine motor function.

4. The system of claim 1, wherein the in-game activities are configured to measure an aspect of mental function of the person, and the second set of health-related data about the person comprises data about the measurement of the mental function.

5. The system of claim 4, wherein the aspect of mental function is selected from the list of language, memory, cognition, attention, abstraction, and perception.

6. The system of claim 1, wherein the frontend service further receives a third set of health-related data comprising social data, the social data comprising the person's interactions with other persons relevant to the person's physical function or mental function.

7. The system of claim 6, wherein the social data is derived from in-game interactions with other players of the game.

8. The system of claim 6, wherein the social data is derived from extra-game interactions with persons not associated with the game.

9. A method for operating a health-related data collection system for healthcare diagnostics and treatment platforms, comprising:
- collecting a first set of health-related data using a piece of exercise equipment comprising a sensor configured to provide the first set of health-related data about a physiological aspect of a person using the exercise equipment while engaged in a virtual reality environment;
- using a frontend service operating on a network-connected computing device comprising a memory and a processor to:
  - receive a network connection from a game client, the game client operating on a remote computing device associated with the person and configured to transmit health-related information about the person to the frontend service;
  - operate the virtual reality environment for engagement by the person while exercising on the exercise equipment, wherein the virtual reality environment is configured to capture a second set of health-related data about the person via in-game activities performed by the person while engaged in the virtual reality environment;
  - transmit virtual reality environment data to the game client, the virtual reality environment data comprising data for rendering of the virtual reality environment on the remote computing device on which the game client is operating; and
  - using a HIPPA-compliant security gateway operating on the network-connected computing device to:
    - establish a HIPPA-compliant health data tunnel with the game client;
    - direct the game client to send the first and second sets of health-related data to the HIPPA-compliant security gateway via that HIPPA-compliant health data tunnel; and
    - store the health-related data in a patient database.

10. The method of claim 9, wherein the physiological aspect is selected from the list of step location, step pressure, and step timing, heart rate, blood pressure, blood-oxygen saturation, volume of oxygen maximum (VO2 Max), body temperature, and electrical activity in muscles and nerve cells that control the muscles.

11. The method of claim 10, further comprising a physical function evaluator comprising a third plurality of programming instructions stored in the memory which, when operating on the processor, causes the network-connected computing device to calculate a physical function from the physiological aspect, wherein the physical function is selected from the list of gait symmetry, gait rhythm, balance, coordination, range of motion, fitness, reaction times, gross motor function, and fine motor function.

12. The method of claim 9, wherein the in-game activities are configured to measure an aspect of mental function of the person, and the second set of health-related data about the person comprises data about the measurement of the mental function.

13. The method of claim 12, wherein the aspect of mental function is selected from the list of language, memory, cognition, attention, abstraction, and perception.

14. The method of claim 9, wherein the frontend service further receives a third set of health-related data comprising social data, the social data comprising the person's interactions with other persons relevant to the person's physical function or mental function.

15. The method of claim 14, wherein the social data is derived from in-game interactions with other players of the game.

16. The method of claim 14, wherein the social data is derived from extra-game interactions with persons not associated with the game.

* * * * *